(12) United States Patent
Hanuka et al.

(10) Patent No.: US 9,987,160 B2
(45) Date of Patent: Jun. 5, 2018

(54) OSTOMY PORT

(71) Applicant: B. Braun Medical SAS, Boulogne-Billancourt (FR)

(72) Inventors: David Hanuka, Ramat-Yishai (IL); Meir Or, Kfar Eshchar (IL)

(73) Assignee: B. Braun Medical SAS, Boulogne-Billancourt (FR)

( * ) Notice: Subject to any disclaimer, the term of this patent is extended or adjusted under 35 U.S.C. 154(b) by 0 days. days.

(21) Appl. No.: 14/499,289

(22) Filed: Sep. 29, 2014

(65) Prior Publication Data

US 2015/0057626 A1    Feb. 26, 2015

Related U.S. Application Data

(63) Continuation of application No. 13/666,178, filed on Nov. 1, 2012, now Pat. No. 8,845,607, which is a
(Continued)

(51) Int. Cl.
| | |
|---|---|
| *A61F 5/441* | (2006.01) |
| *A61F 5/445* | (2006.01) |
| *A61F 5/44* | (2006.01) |
| *A61F 5/443* | (2006.01) |
| *A61F 5/442* | (2006.01) |
| *A61F 5/449* | (2006.01) |

(52) U.S. Cl.
CPC .............. *A61F 5/4407* (2013.01); *A61F 5/44* (2013.01); *A61F 5/441* (2013.01); *A61F 5/442* (2013.01); *A61F 5/443* (2013.01); *A61F 5/4404* (2013.01); *A61F 5/4405* (2013.01); *A61F 5/445* (2013.01); *A61F 5/449* (2013.01); *A61F 2005/4402* (2013.01); *A61F 2005/4455* (2013.01)

(58) Field of Classification Search
CPC combination set(s) only.
See application file for complete search history.

(56) References Cited

U.S. PATENT DOCUMENTS

| | | |
|---|---|---|
| 2,243,529 A | 5/1941 | Grossman et al. |
| 2,341,984 A | 2/1944 | Graves |
| | (Continued) | |

FOREIGN PATENT DOCUMENTS

| | | |
|---|---|---|
| CN | 1694661 | 11/2005 |
| DE | 19921555 | 2/2000 |
| | (Continued) | |

OTHER PUBLICATIONS

Communication Pursuant to Article 94(3) EPC dated Nov. 5, 2014 From the European Patent Office Re. Application No. 11724783.3.
(Continued)

*Primary Examiner* — Todd J Scherbel
*Assistant Examiner* — Guy K Townsend
(74) *Attorney, Agent, or Firm* — Clark & Elbing LLP

(57) ABSTRACT

A stomal insert for conducting waste content from an intestinal portion in an abdominal cavity through a stoma in an abdominal wall comprising; a cover for covering the stoma; a fixation element for anchoring the stomal insert to a visceral side of the abdominal wall; and a pliable, axially elastic tube interconnecting said cover and said fixation element and sized to apply a tensile force to said cover and to said fixation element.

31 Claims, 31 Drawing Sheets

Related U.S. Application Data continuation of application No. PCT/IB2011/051933, filed on May 2, 2011, which is a continuation-in-part of application No. PCT/IL2010/000565, filed on Jul. 14, 2010.

(60) Provisional application No. 61/431,084, filed on Jan. 10, 2011, provisional application No. 61/330,359, filed on May 2, 2010, provisional application No. 61/225,546, filed on Jul. 14, 2009.

(56) References Cited

U.S. PATENT DOCUMENTS

| | | | |
|---|---|---|---|
| 2,510,766 A | 6/1950 | Surface | |
| 2,544,579 A | 3/1951 | Ardner | |
| 2,639,710 A | 5/1953 | Fazio | |
| 2,667,167 A | 1/1954 | Raiche | |
| 2,971,510 A | 2/1961 | Berger | |
| 3,398,744 A | 8/1968 | Hooper | |
| 3,447,533 A | 6/1969 | Spicer | |
| 3,718,141 A | 2/1973 | Goetz | |
| 3,976,076 A | 8/1976 | Beach | |
| 4,030,500 A | 6/1977 | Ronnquist | |
| 4,121,589 A | 8/1978 | McDonnell | |
| 4,170,231 A | 10/1979 | Collins | |
| 4,183,357 A | 1/1980 | Bentley et al. | |
| 4,209,010 A | 6/1980 | Ward et al. | |
| 4,210,131 A | 7/1980 | Perlin | |
| 4,211,224 A | 7/1980 | Kubach et al. | |
| 4,232,672 A | 11/1980 | Steer et al. | |
| 4,265,244 A | 5/1981 | Hill | |
| 4,338,937 A | 7/1982 | Lerman | |
| 4,344,434 A | 8/1982 | Robertson | |
| 4,351,322 A | 9/1982 | Prager | |
| 4,381,765 A | 5/1983 | Burton | |
| 4,399,809 A | 8/1983 | Baro et al. | |
| 4,421,124 A | 12/1983 | Marshall | |
| 4,460,363 A | 7/1984 | Steer et al. | |
| 4,462,510 A * | 7/1984 | Steer | A61M 1/0019 137/218 |
| 4,516,974 A | 5/1985 | Davis | |
| 4,534,761 A | 8/1985 | Raible | |
| 4,634,421 A | 1/1987 | Hegemann | |
| 4,642,107 A | 2/1987 | Arnone et al. | |
| 4,662,890 A | 5/1987 | Burton et al. | |
| 4,721,508 A | 1/1988 | Burton | |
| 4,786,283 A | 11/1988 | Andersson | |
| 4,804,375 A | 2/1989 | Robertson | |
| 4,810,250 A | 3/1989 | Ellenberg et al. | |
| 4,854,316 A | 8/1989 | Davis | |
| 4,863,447 A * | 9/1989 | Smith | A61F 5/441 251/323 |
| 4,941,869 A | 7/1990 | D'Amico | |
| 4,950,223 A | 8/1990 | Silvanov | |
| 4,981,465 A | 1/1991 | Ballan et al. | |
| 5,004,464 A | 4/1991 | Leise, Jr. | |
| 5,026,360 A | 6/1991 | Johnson et al. | |
| 5,045,052 A | 9/1991 | Sans | |
| 5,108,430 A | 4/1992 | Ravo | |
| 5,125,916 A | 6/1992 | Panebianco et al. | |
| 5,135,519 A | 8/1992 | Helmer | |
| 5,163,897 A | 11/1992 | Persky | |
| 5,163,930 A | 11/1992 | Blum | |
| 5,261,898 A | 11/1993 | Polin et al. | |
| 5,269,774 A | 12/1993 | Gray | |
| 5,372,594 A * | 12/1994 | Colacello | A61F 5/441 55/385.4 |
| 5,401,264 A * | 3/1995 | Leise, Jr. | A61F 5/441 604/333 |
| 5,501,678 A | 3/1996 | Olsen | |
| 5,549,588 A | 8/1996 | Johnson | |
| 5,569,216 A | 10/1996 | Kim | |
| 5,658,266 A | 8/1997 | Colacello et al. | |
| 5,658,267 A | 8/1997 | Colacello et al. | |
| 5,683,372 A | 11/1997 | Colacello et al. | |
| 5,771,590 A | 6/1998 | Colacello et al. | |
| 5,785,677 A | 7/1998 | Auweiler | |
| 5,785,695 A | 7/1998 | Sato et al. | |
| 5,947,942 A | 9/1999 | Galjour | |
| 6,033,390 A | 3/2000 | Von Dyck | |
| 6,050,982 A | 4/2000 | Wheeler | |
| 6,329,465 B1 | 12/2001 | Takahashi et al. | |
| 6,350,255 B1 | 2/2002 | Von Dyck | |
| 6,357,445 B1 | 5/2002 | Shaw | |
| 6,481,589 B2 | 11/2002 | Blomdahl et al. | |
| 6,485,476 B1 | 11/2002 | Von Dyck et al. | |
| 6,595,971 B1 | 7/2003 | Von Dyck et al. | |
| 6,659,988 B1 | 12/2003 | Steer et al. | |
| 6,689,111 B2 | 2/2004 | Mulhauser et al. | |
| 6,695,825 B2 | 2/2004 | Castles | |
| 6,723,079 B2 | 4/2004 | Cline | |
| 6,963,772 B2 | 11/2005 | Bloom et al. | |
| 7,001,367 B2 | 2/2006 | Arkinstall | |
| 7,083,569 B2 | 8/2006 | Boulanger et al. | |
| 7,087,041 B2 | 8/2006 | Von Dyck et al. | |
| 7,250,040 B2 | 7/2007 | Andersen | |
| 7,314,443 B2 | 1/2008 | Jordan et al. | |
| 7,582,072 B2 | 9/2009 | McMichael | |
| 7,670,289 B1 | 3/2010 | McCall | |
| 7,857,796 B2 | 12/2010 | Cline et al. | |
| 8,070,737 B2 | 12/2011 | Cline et al. | |
| 8,092,437 B2 | 1/2012 | Cline | |
| 8,100,875 B2 | 1/2012 | Cline et al. | |
| 8,142,406 B2 | 3/2012 | Blum | |
| 8,388,586 B2 | 3/2013 | Weig | |
| 8,460,259 B2 | 6/2013 | Tsai | |
| 8,821,464 B2 | 9/2014 | Hanuka et al. | |
| 8,821,465 B2 | 9/2014 | Hanuka et al. | |
| 8,845,607 B2 | 9/2014 | Hanuka et al. | |
| 8,858,519 B2 | 10/2014 | Hanuka et al. | |
| 8,864,729 B2 | 10/2014 | Hanuka et al. | |
| 8,900,116 B2 | 12/2014 | Hanuka et al. | |
| 8,998,862 B2 | 4/2015 | Hanuka et al. | |
| D739,012 S | 9/2015 | Hanuka et al. | |
| D739,525 S | 9/2015 | Hanuka et al. | |
| 9,314,365 B2 | 4/2016 | Hanuka et al. | |
| 9,345,612 B2 | 5/2016 | Hanuka et al. | |
| 9,517,157 B2 | 12/2016 | Hanuka et al. | |
| D783,814 S | 4/2017 | Hanuka et al. | |
| D796,029 S | 8/2017 | Hanuka et al. | |
| 2003/0150050 A1 | 8/2003 | Tanaka et al. | |
| 2003/0199783 A1 | 10/2003 | Bloom et al. | |
| 2003/0220621 A1 | 11/2003 | Arkinstall | |
| 2004/0029467 A1 | 2/2004 | Lacroix | |
| 2004/0073179 A1 | 4/2004 | Andersen | |
| 2004/0122527 A1 | 6/2004 | Imran | |
| 2004/0167376 A1 | 8/2004 | Peters et al. | |
| 2004/0171999 A1 | 9/2004 | Andersen et al. | |
| 2004/0181197 A1 | 9/2004 | Cline | |
| 2005/0027159 A1 | 2/2005 | Feng et al. | |
| 2005/0054996 A1 | 3/2005 | Gregory | |
| 2005/0065488 A1 | 3/2005 | Elliott | |
| 2005/0104457 A1 | 5/2005 | Jordan et al. | |
| 2006/0048283 A1 | 3/2006 | Sorensen | |
| 2006/0106354 A1 | 5/2006 | Vantroostenberghe | |
| 2006/0206069 A1 | 9/2006 | Cline | |
| 2006/0229596 A1 | 10/2006 | Weiser et al. | |
| 2007/0049878 A1 | 3/2007 | Kim et al. | |
| 2007/0088300 A1 | 4/2007 | Cline et al. | |
| 2007/0129695 A1 | 6/2007 | Blum | |
| 2007/0142780 A1 | 6/2007 | Van Lue | |
| 2007/0191794 A1 | 8/2007 | Cline et al. | |
| 2007/0219532 A1 | 9/2007 | Karpowicz et al. | |
| 2007/0260206 A1 | 11/2007 | Mullejans et al. | |
| 2007/0276346 A1 | 11/2007 | Poulsen et al. | |
| 2008/0004580 A1 | 1/2008 | Mullejans et al. | |
| 2008/0033380 A1 | 2/2008 | Andersen | |
| 2008/0091154 A1 | 4/2008 | Botten | |
| 2008/0108862 A1 | 5/2008 | Jordan et al. | |
| 2008/0135044 A1 | 6/2008 | Freitag et al. | |
| 2008/0269698 A1 | 10/2008 | Alexander et al. | |
| 2008/0275410 A1 | 11/2008 | Burt | |
| 2009/0043151 A1 | 2/2009 | Gobel | |

(56) References Cited

U.S. PATENT DOCUMENTS

| | | | |
|---|---|---|---|
| 2009/0216206 | A1 | 8/2009 | Nishtala et al. |
| 2009/0247969 | A1 | 10/2009 | Nishtala et al. |
| 2010/0069859 | A1 | 3/2010 | Weig |
| 2010/0174253 | A1 | 7/2010 | Cline et al. |
| 2011/0015475 | A1 | 1/2011 | Hanuka et al. |
| 2011/0040231 | A1 | 2/2011 | Gregory |
| 2011/0106032 | A1 | 5/2011 | Kratky |
| 2012/0136324 | A1 | 5/2012 | Hanuka et al. |
| 2013/0053803 | A1 | 2/2013 | Willoughby et al. |
| 2013/0060212 | A1 | 3/2013 | Hanuka et al. |
| 2013/0060213 | A1 | 3/2013 | Hanuka et al. |
| 2013/0060214 | A1 | 3/2013 | Willoughby et al. |
| 2013/0079736 | A1 | 3/2013 | Hanuka et al. |
| 2013/0079737 | A1 | 3/2013 | Hanuka et al. |
| 2013/0079738 | A1 | 3/2013 | Hanuka et al. |
| 2013/0116642 | A1 | 5/2013 | Hanuka et al. |
| 2013/0304008 | A1 | 11/2013 | Hanuka et al. |
| 2015/0025488 | A1 | 1/2015 | Hanuka et al. |
| 2015/0057626 | A1 | 2/2015 | Hanuka et al. |
| 2015/0141944 | A1 | 5/2015 | Hanuka et al. |
| 2015/0305916 | A1 | 10/2015 | Hanuka et al. |
| 2016/0113810 | A1 | 4/2016 | Hanuka et al. |
| 2016/0166424 | A1 | 6/2016 | Hanuka et al. |

FOREIGN PATENT DOCUMENTS

| | | |
|---|---|---|
| DE | 102004001631 | 8/2004 |
| DE | 102007062133 | 7/2009 |
| EP | 1795157 | 6/2007 |
| EP | 2027835 | 2/2009 |
| FR | 2870112 | 11/2005 |
| GB | 2094153 | 9/1982 |
| JP | 2006-314479 | 11/2006 |
| JP | 2008-507308 | 3/2008 |
| WO | WO 87/03192 | 6/1987 |
| WO | WO 90/07311 | 7/1990 |
| WO | WO 96/32904 | 10/1996 |
| WO | WO 99/43277 | 9/1999 |
| WO | WO 01/49224 | 7/2001 |
| WO | WO 02/058603 | 8/2002 |
| WO | WO 03/065945 | 8/2003 |
| WO | WO 03/071997 | 9/2003 |
| WO | WO 2006/010556 | 2/2006 |
| WO | WO 2007/030703 | 3/2007 |
| WO | WO 2008/048856 | 4/2008 |
| WO | WO 2008/103789 | 8/2008 |
| WO | WO 2008/141180 | 11/2008 |
| WO | WO 2009/083183 | 7/2009 |
| WO | WO 2009/155537 | 12/2009 |
| WO | WO 2011/007355 | 1/2011 |
| WO | WO 2011/013872 | 2/2011 |
| WO | WO 2011/039517 | 4/2011 |
| WO | WO 2011/057635 | 5/2011 |
| WO | WO 2011/138727 | 11/2011 |
| WO | WO 2011/138728 | 11/2011 |
| WO | WO 2011/138731 | 11/2011 |
| WO | WO 2013/022487 | 2/2013 |
| WO | WO 2013/168165 | 11/2013 |
| WO | WO 2014/081889 | 5/2014 |
| WO | WO 2014/181338 | 11/2014 |
| WO | WO 2014/181339 | 11/2014 |

OTHER PUBLICATIONS

Restriction Official Action dated Mar. 20, 2015 From the US Patent and Trademark Office Re. U.S. Appl. No. 13/890,433.
Advisory Action Before the Filing of an Appeal Brief dated Feb. 4, 2014 From the US Patent and Trademark Office Re. U.S. Appl. No. 12/835,838.
Advisory Action Before the Filing of an Appeal Brief dated Mar. 31, 2014 From the US Patent and Trademark Office Re. U.S. Appl. No. 13/384,343.
Applicant-Initiated Interview Summary dated Dec. 13, 2013 From the US Patent and Trademark Office Re. U.S. Appl. No. 13/666,244.
Applicant-Initiated Interview Summary dated Dec. 13, 2013 From the US Patent and Trademark Office Re. U.S. Appl. No. 13/666,513.
Applicant-Initiated Interview Summary dated Apr. 14, 2014 From the US Patent and Trademark Office Re. U.S. Appl. No. 13/384,343.
Applicant-Initiated Interview Summary dated Jul. 25, 2013 From the US Patent and Trademark Office Re. U.S. Appl. No. 13/680,161.
Applicant-Initiated Interview Summary dated Jul. 26, 2013 From the US Patent and Trademark Office Re. U.S. Appl. No. 13/666,513.
Applicant-Initiated Interview Summary dated Jul. 26, 2013 From the US Patent and Trademark Office Re. U.S. Appl. No. 13/680,169.
Applicant-Initiated Interview Summary dated Jan. 27, 2014 From the US Patent and Trademark Office Re. U.S. Appl. No. 13/384,343.
Communication Pursuant to Article 94(3) EPC dated Feb. 11, 2013 From the European Patent Office Re. Application No. 10747085.5.
Communication Pursuant to Article 94(3) EPC dated Dec. 17, 2013 From the European Patent Office Re. Application No. 11723672.9.
Communication Pursuant to Article 94(3) EPC dated Dec. 19, 2013 From the European Patent Office Re. Application No. 11723674.5.
Communication Pursuant to Article 94(3) EPC dated Dec. 19, 2013 From the European Patent Office Re. Application No. 11724783.3.
Communication Relating to the Results of the Partial International Search dated Aug. 12, 2011 From the International Searching Authority Re. Application No. PCT/IB2011/051932.
Communication Relating to the Results of the Partial International Search dated Aug. 16, 2011 From the International Searching Authority Re. Application No. PCT/IB2011/051933.
Communication Relating to the Results of the Partial International Search dated Sep. 16, 2013 From the International Searching Authority Re. Application No. PCT/IL2013/050401.
Communication Relating to the Results of the Partial International Search dated Nov. 17, 2010 From the International Searching Authority Re. Application No. PCT/IL2010/000565.
Communication Relating to the Results of the Partial International Search dated Aug. 18, 2011 From the International Searching Authority Re: Application No. PCT/IB2011/051938.
Communication Under Rule 71(3) EPC dated May 19, 2014 From the European Patent Office Re. Application No. 10747082.5.
Corrected Notice of Allowability dated Jul. 8, 2014 From the US Patent and Trademark Office Re. U.S. Appl. No. 13/666,461.
Corrected Notice of Allowability dated Jul. 22, 2014 From the US Patent and Trademark Office Re. U.S. Appl. No. 13/666,513.
International Preliminary Report on Patentability dated Jun. 1, 2012 From the International Preliminary Examining Authority Re. Application No. PCT/IB2011/051933.
International Preliminary Report on Patentability dated Jun. 5, 2012 From the International Preliminary Examining Authority Re. Application No. PCT/IB2011/051932.
International Preliminary Report on Patentability dated Sep. 6, 2012 From the International Preliminary Examining Authority Re. Application No. PCT/IB2011/051938.
International Preliminary Report on Patentability dated Nov. 15, 2012 From the International Bureau of WIPO Re. Application No. PCT/IB2011/051936.
International Preliminary Report on Patentability dated Oct. 31, 2011 From the International Preliminary Examining Authority Re. Application No. PCT/IL2010/000565.
International Search Report and the Written Opinion dated Oct. 14, 2011 From the International Searching Authority Re. Application No. PCT/IB2011/051933.
International Search Report and the Written Opinion dated Oct. 17, 2011 From the International Searching Authority Re. Application No. PCT/IB2011/051932.
International Search Report and the Written Opinion dated Aug. 18, 2011 From the International Searching Authority Re. Application No. PCT/IB2011/051936.
International Search Report and the Written Opinion dated Oct. 19, 2011 From the International Searching Authority Re: Application No. PCT/IB2011/051938.
International Search Report and the Written Opinion dated Dec. 20, 2013 From the International Searching Authority Re. Application No. PCT/IL2013/050401.

(56) References Cited

OTHER PUBLICATIONS

International Search Report and the Written Opinion dated Feb. 28, 2011 From the International Searching Authority Re. Application No. PCT/IL2010/000565.
Invitation to Pay Additional Fees dated Oct. 7, 2011 From the International Preliminary Examining Authority Re. Application No. PCT/IL2010/000565.
Notice of Allowance dated Jun. 2, 2014 From the US Patent and Trademark Office Re. U.S. Appl. No. 13/666,178.
Notice of Allowance dated Apr. 4, 2014 From the US Patent and Trademark Office Re. U.S. Appl. No. 13/680,169.
Notice of Allowance dated May 8, 2014 From the US Patent and Trademark Office Re. U.S. Appl. No. 13/666,461.
Notice of Allowance dated Feb. 18, 2014 From the US Patent and Trademark Office Re. U.S. Appl. No. 13/666,513.
Notice of Allowance dated Mar. 18, 2014 From the US Patent and Trademark Office Re. U.S. Appl. No. 13/666,178.
Notice of Allowance dated Apr. 29, 2014 From the US Patent and Trademark Office Re. U.S. Appl. No. 13/680,161.
Notice of Reason for Rejection dated Apr. 15, 2014 From the Japanese Patent Office Re. Application No. 2012-520149 and its Translation Into English.
Notification Concerning Informal Communications With the Applicant dated May 3, 2012 From International Searching Authority Re: Application No. PCT/IB2011/051938.
Notification Concerning Informal Communications With the Applicant dated May 4, 2012 From the International Searching Authority Re: Application No. PCT/IB2011/051933.
Notification Concerning Informal Communications With the Applicant dated May 18, 2012 From the International Searching Authority Re: Application No. PCT/IB2011/051932.
Notification of Office Action dated May 6, 2014 From The State intellectual Property Office of the People's Republic of China Re. Application No. 2011800331827 and its Translation Into English.
Notification of Office Action dated Apr. 18, 2014 From the State Intellectual Property Office of the People's Republic of China Re. Application No. 201080032032.X and its Translation Into English.
Notification of Office Action dated May 27, 2014 From The State Intellectual Property Office of the People's Republic of China Re. Application No. 201180033162.X.
Official Action dated Jul. 1, 2013 From the US Patent and Trademark Office Re. U.S. Appl. No. 13/384,343.
Official Action dated Mar. 5, 2013 From the US Patent and Trademark Office Re. U.S. Appl. No. 13/666,513.
Official Action dated Nov. 7, 2013 From the US Patent and Trademark Office Re. U.S. Appl. No. 13/666,178.
Official Action dated Nov. 7, 2013 From the US Patent and Trademark Office Re. U.S. Appl. No. 13/680,169.
Official Action dated May 9, 2013 From the US Patent and Trademark Office Re. U.S. Appl. No. 13/666,461.
Official Action dated Jul. 10, 2013 From the US Patent and Trademark Office Re. U.S. Appl. No. 13/680,169.
Official Action dated Jul. 11, 2013 From the US Patent and Trademark Office Re. U.S. Appl. No. 13/680,161.
Official Action dated Nov. 13, 2013 From the US Patent and Trademark Office Re. U.S. Appl. No. 13/666,461.
Official Action dated Jan. 14, 2014 From the US Patent and Trademark Office Re. U.S. Appl. No. 13/680,161.
Official Action dated Oct. 16, 2013 From the US Patent and Trademark Office Re. U.S. Appl. No. 13/666,244.
Official Action dated Oct. 16, 2013 From the US Patent and Trademark Office Re. U.S. Appl. No. 13/666,513.
Official Action dated Oct. 18, 2013 From the US Patent and Trademark Office Re. U.S. Appl. No. 13/384,343.
Official Action dated Mar. 25, 2013 From the US Patent and Trademark Office Re. U.S. Appl. No. 13/666,178.
Official Action dated Jun. 26, 2014 From the US Patent and Trademark Office Re. U.S. Appl. No. 13/384,343.
Official Action dated Aug. 29, 2013 From the US Patent and Trademark Office Re. U.S. Appl. No. 12/835,838.
Official Action dated Jul. 29, 2014 From the US Patent and Trademark Office Re. U.S. Appl. No. 13/666,244.
Official Action dated Jan. 30, 2013 From the US Patent and Trademark Office Re. U.S. Appl. No. 12/835,838.
Response Dated May 30, 2011 to the Written Opinion dated Feb. 28, 2011 From the International Searching Authority Re. Application No. PCT/IL2010/000565.
Restriction Official Action dated Oct. 15, 2012 From the US Patent and Trademark Office Re. U.S. Appl. No. 12/835,838.
Search Report dated May 6, 2014 From the State Intellectual Property Office of the People's Republic of China Re. Application No. 2011800331827 and its Translation Into English.
Search Report dated Apr. 18, 2014 From the State Intellectual Property Office of the People's Republic of China Re. Application No. 201080032032.X and its Translation Into English.
Summons to Attend Oral Proceedings Pursuant to Rule 115(1) EPC dated Nov. 22, 2013 From the European Patent Office Re. Application No. 10747082.5.
Supplemental Notice of Allowability dated Sep. 16, 2014 From the US Patent and Trademark Office Re. U.S. Appl. No. 13/666,461.
Supplemental Notice of Allowability dated Sep. 16, 2014 From the US Patent and Trademark Office Re. U.S. Appl. No. 13/680,161.
Supplemental Notice of Allowability dated May 21, 2014 From the US Patent and Trademark Office Re. U.S. Appl. No. 13/666,513.
Supplemental Notice of Allowability dated Jul. 22, 2014 From the US Patent and Trademark Office Re. U.S. Appl. No. 13/680,169.
Supplemental Notice of Allowability dated Jul. 23, 2014 From the US Patent and Trademark Office Re. U.S. Appl. No. 13/666,461.
Supplemental Notice of Allowability dated Jun. 23, 2014 From the US Patent and Trademark Office Re. U.S. Appl. No. 13/666,513.
Supplemental Notice of Allowability dated Jun. 23, 2014 From the US Patent and Trademark Office Re. U.S. Appl. No. 13/680,161.
Supplemental Notice of Allowability dated Jul. 25, 2014 From the US Patent and Trademark Office Re. U.S. Appl. No. 13/680,161.
Supplemental Notice of Allowability dated Jun. 27, 2014 From the US Patent and Trademark Office Re. U.S. Appl. No. 13/680,169.
Translation of Notification of Office Action dated Jul. 30, 2013 From the State Intellectual Property Office of the People's Republic of China Re. Application No. 201080032032.X.
Written Opinion dated Jun. 1, 2012 From the International Preliminary Examining Authority Re. Application No. PCT/IB2011/051938.
Zhang et al. "Occlusion Effect Comparison of Artificial Silicone Rubber Closure Devices With Different Diameters", Chinese Journal of Tissue Engineering Research, 16(8): 1496-1500, Feb. 19, 2012. Abstract in English.
International Preliminary Report on Patentability dated Nov. 20, 2014 From the International Bureau of WIPO Re. Application No. PCT/IL2013/050401.
Notice of Allowance dated Nov. 28, 2014 From the US Patent and Trademark Office Re. U.S. Appl. No. 13/384,343.
International Search Report and the Written Opinion dated Dec. 19, 2014 From the International Searching Authority Re. Application No. PCT/IL2014/050416.
International Search Report and the Written Opinion dated Dec. 19, 2014 From the International Searching Authority Re. Application No. PCT/IL2014/050417.
Communication Relating to the Results of the Partial International Search dated Sep. 16, 2014 From the International Searching Authority Re. Application No. PCT/IL2014/050416.
Notice of Allowance dated Oct. 1, 2014 From the US Patent and Trademark Office Re. U.S. Appl. No. 12/835,838.
Communication Relating to the Results of the Partial International Search dated Sep. 16, 2014 From the International Searching Authority Re. Application No. PCT/IL2014/050417.
Notification of Office Action and Search Report dated Oct. 20, 2014 From the State Intellectual Property Office of the People's Republic of China Re. Application No. 201080032032.X and its Translation Into English.
Notification of Office Action dated Dec. 2, 2014 From The State Intellectual Property Office of the People's Republic of China Re. Application No. 2011800331827.

(56) References Cited

OTHER PUBLICATIONS

Official Action dated Jan. 26, 2015 From the US Patent and Trademark Office Re. U.S. Appl. No. 13/666,244.
Translation Dated Dec. 15, 2014 of Notification of Office Action dated Dec. 2, 2014 From the State Intellectual Property Office of the People's Republic of China Re. Application No. 2011800331827.

* cited by examiner

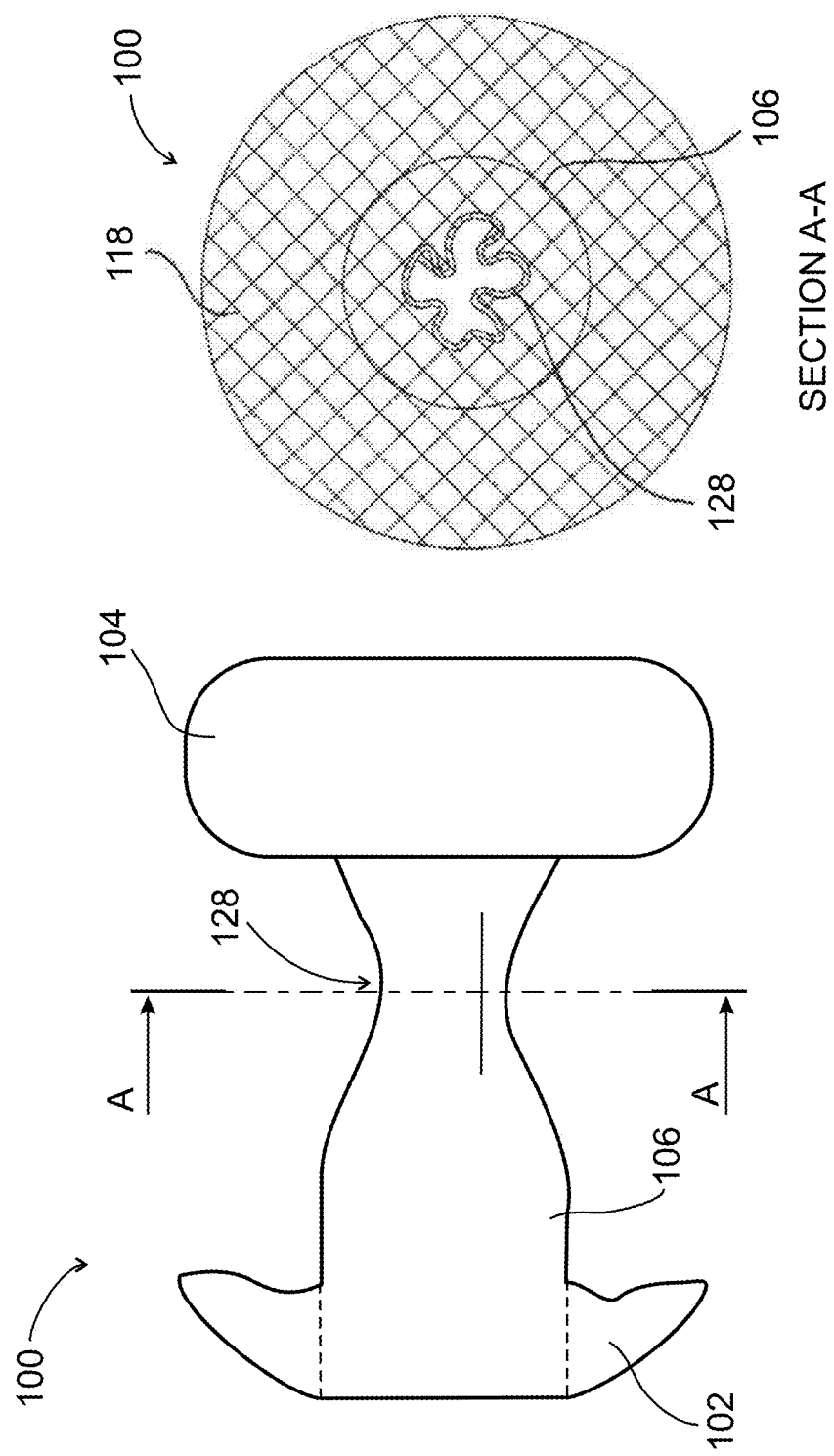

DETAIL B

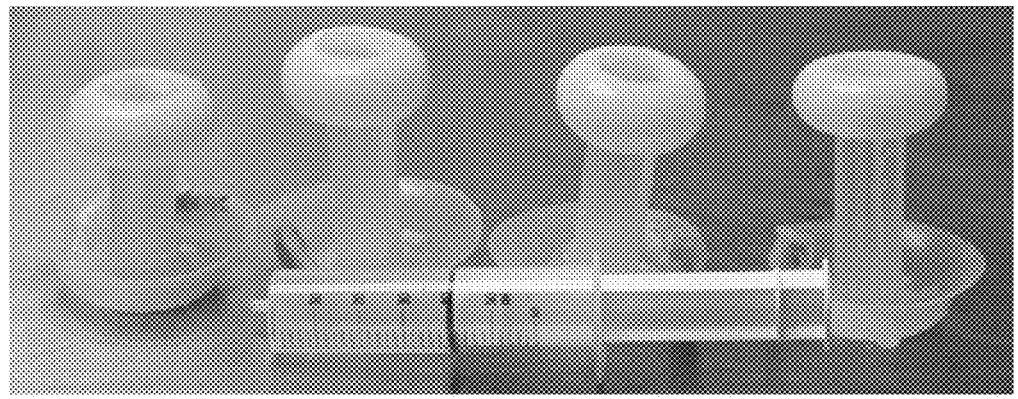
The Ostomy Port
Figure 23
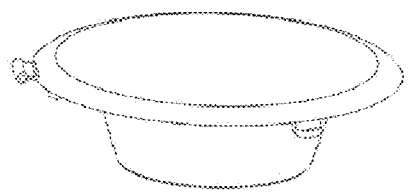
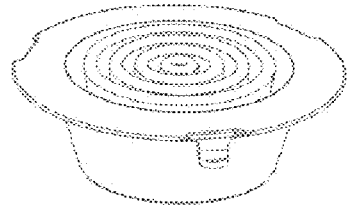
Schematic view of the CapsuleCap™ with the aesthetic cover on
Schematic view of the CapsuleCap™ with the cover removed – revealing the furled collection bag
Figure 24A
Figure 24B Abdominal wall piercing Exposure of subcutaneous layer Creation of a cecal ostomy A complete stoma Distribution of device usage days between full day insertions, partial day insertions and day of no insertions Retaining test arrangement: the device is inserted into the stoma and then pulled outwards with an electronic force gauge.

Sealing test arrangement: 500ml tap water injected into the device through a dedicated inlet valve The device full of water mixed with waste matter. Note the dryness of the skin around the device.

Body weight of the animals along study duration

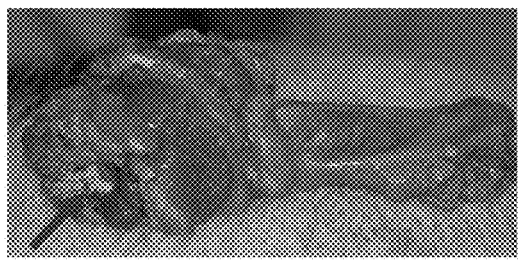
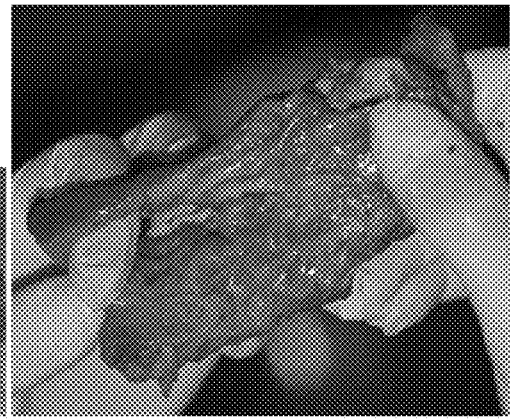

Example of macro pathological evaluation (animal 9); a portion of the abdominal wall and the intestine. The stoma is indicated by an arrow.

Figure 30A

Example of macro pathological evaluation (animal 12); the mucosal layer of the intestinal portion around the device's tube.

Figure 30B

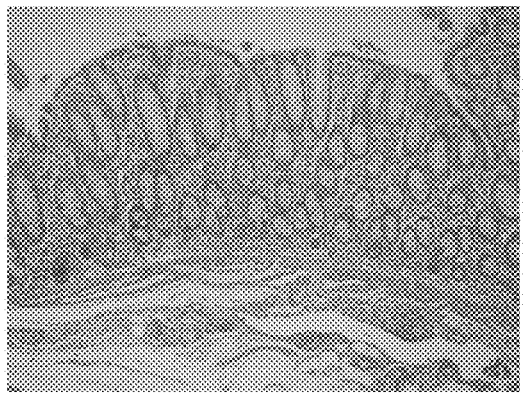
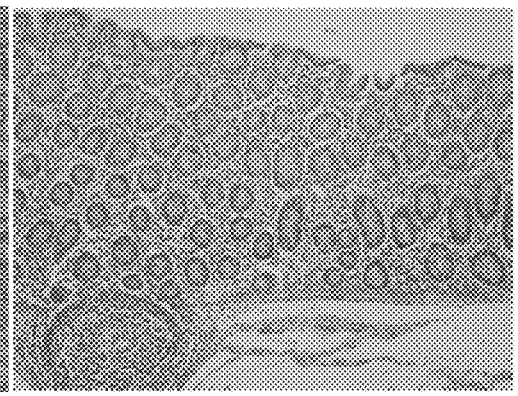

Example of pathological evaluation (animal 9); functional intestine (in contact with the retention balloon).

Figure 31A

Example of pathological evaluation (animal 9); control intestine (no contact with the device).

Figure 31B

Days from study initiation

Distribution of device unintended ejections along usage duration. (a) Animal #9; usage duration = 97 days. (b) Animal #10; usage duration =63 days. (c) Animal #12; usage duration =35 days. (d) Animal 13; usage duration =29 days.

Fecal matter fills the device and pushes its silicone sealing outwards

Average volume of excrement discharged from the stoma upon removal of the device. Error bars indicate one standard deviation.

Possible contributions to device ejection: Location of the device relative to the animal's abdomen Device being rubbed against the stall's floor during animal's crouching. Arrow indicates device location.

Sample of a device destroyed by a study animal

Sample of a device destroyed by a study animal

OSTOMY PORT

RELATED APPLICATIONS

This application is a Continuation of U.S. patent application Ser. No. 13/666,178 filed on Nov. 1, 2012, which is a Continuation of PCT Patent Application No. PCT/IB2011/051933 having International filing date of May 2, 2011, which claims the benefit of priority under 35 USC 119(e) of U.S. Provisional Patent Application Nos. 61/431,084 filed on Jan. 10, 2011 and 61/330,359 filed on May 2, 2010. PCT Patent Application No. PCT/IB2011/051933 is also a Continuation-In-Part (CIP) of PCT Patent Application No. PCT/IL2010/000565 filed on Jul. 14, 2010, which claims the benefit of priority under 35 USC 119(e) of U.S. Provisional Patent Application Nos. 61/330,359 filed on May 2, 2010 and 61/225,546 filed on Jul. 14, 2009. The contents of the above applications are all incorporated herein by reference as if fully set forth in their entirety.

PCT Patent Application No. PCT/IB2011/051933 is also related to PCT Patent Application Nos. PCT/IB2011/051938, PCT/IB2011/051932 and PCT/IB2011/051936, which were all filed by, inter alia, Applicant Stimatix GI Ltd., concurrently with PCT Patent Application No. PCT/IB2011/051933, the disclosures of which are incorporated herein by reference.

FIELD AND BACKGROUND OF THE INVENTION

The present invention, in some embodiments thereof, relates to the field of prosthetic implants, and more particularly, to an Ostomy port for use following Ostomy cases such as Colostomy, Ileostomy or Urostomy, or for fecal incontinence.

An Ostomy is a surgical procedure wherein an opening (stoma) is created in the body, for example, for the discharge of body wastes. When performing an ostomy, the physician will generally form a stoma in the abdominal wall and attach an end or a side of a healthy portion of the intestine (large or small intestine, depending on the type of ostomy) to the stoma from the visceral side of the abdominal wall or, alternatively, pass the intestinal portion through the stoma and attach it to the outside of the abdominal wall. The stoma may be permanently left in a patient suffering from a condition for when it is no longer possible for the intestinal content to pass out via the anus, for example, due to colon cancer, diverticulitis, trauma, or inflammatory bowel disease), or may be temporary, as may be the case following an operation on a section of the bowel (small intestine and/or large intestine) requiring a healing period.

Following a stoma operation, a stomal insert may be inserted through the stoma into the intestine and may serve as an ostomy port for preventing the body wastes from coming in contact with the external abdominal wall as they are expelled through the stoma. The ostomy port may form part of an ostomy containment system which may serve to control the flow of the body wastes out the stoma.

U.S. Patent Publication No. 2007/0049878 A1, "Bowel Management System", discloses "a bowel management system includes a waste collection catheter having at least two distinct sections. The first section is patient proximal when disposed in the patient's rectum and has durometer hardness in the range of about 50 A to about 90 A. The second catheter section is connected to the first section and has durometer hardness in the range of about 5 A to about 49 A. A selectively collapsible, substantially spherical retention balloon is attached coaxially and exterior of the first catheter section such that the proximal-most end of the retention balloon is coincident to the proximal-most end of the first section of the waste collection catheter, the substantially spherical retention balloon having an inflated size so as to be sufficiently large enough to retain the patient proximal end of the catheter in the patient's rectum without being so large as to trigger a defecatory response in the patient."

U.S. Patent Publication No. 2005/0054996 A1, "Fecal Management Appliance And Method And Apparatus For Introducing Same", discloses "the end of the elongated tubular element of the appliance that is designed to be inserted into a body cavity or vessel is formed entirely of soft, compliant material. That end carries an inflatable balloon formed in its fully inflated shape. The balloon is inflated to a predetermined low pressure level to prevent pressure necrosis in the adjacent tissue. A method and apparatus for introducing the soft end of the appliance into the body cavity are also provided. The introducer apparatus includes rigid core surrounded by a soft, compliant sleeve. The sleeve extends beyond the rigid core to form an invertable section. The soft end of the appliance is situated adjacent the apparatus, the balloon is wrapped around the apparatus, and the sleeve section is inverted over the appliance, compressing the balloon and forming a soft, rounded insertion tip. The unit is then introduced into the body cavity. After the appliance is separated from the apparatus, the apparatus is withdrawn."

U.S. Patent Publication No. 2009/0247969 A1, "Waste Management System", discloses "a waste management system includes a waste transport device, a waste collection device, and an insertion device. The waste transport device includes a collection member with a distal end opening having a first cross-sectional area and a proximal end opening having a second cross-sectional area less than the first cross-sectional area, and a retention cuff disposed about an outer surface of the collection member. The insertion device is positioned about the collection member and retention cuff to retain the collection member and retention cuff in a collapsed configuration."

WO 2009/155537 A1, "Ostomy Appliances For Directing Effluent Output", describes "a stoma extender includes a first end for insertion into a stoma for diverting stomal effluent into the stoma extender before the effluent exits the stoma; a second end for remaining external of the stoma, for providing a discharge exit for stomal effluent; and a conduit portion coupled between the first and second ends for communicating stomal effluent through the stoma extender, wherein the length of the conduit portion is adjustable stably, to permit adaptation of the stoma extender to an individual's stoma."

U.S. Pat. No. 5,569,216 to Kim describes "a multipurpose colostomy device for fixing in the stoma or rectum of a human body, includes an internal balloon, a ring configured external balloon surrounding the internal balloon, a connecting tube disposed under the both internal and external balloons, a joint tube operatively connected to a drainage hose and disposed under connecting tube, a supporting plate disposed between the connecting and joint tubes for fixing the colostomy to the abdominal wall, and an L-shaped supply tube containing a pair of air passages, a washing fluid passage and an enema fluid passage."

WO 96/32904, "Prosthesis For Bowel Evacuation Control-Colostomy Tube", describes "the problem which is solved by a prosthesis for bowel evacuation control at the incontinence of an artificial or natural anus in accordance with the invention is how to provide simple, safe and reliable control of bowel evacuation in artificial or natural incontinence, where under artificial incontinence colostomy, i.e. a surgically formed opening in the large intestine through the abdominal wall is understood, and under natural incontinence the incontinence of the anal sphincter is understood. The illustrated prosthesis inserted in a colostomy, i.e. a bowel (1) extended through the abdominal wall (2), consists of an inner ring (3) which continues into a pellicular tube (4) and this into a faceplate (5), and of a cover (8). In this embodiment the inner ring (3) is carried out as a ring made of pliable, organism-friendly material with a built-in reinforcement (9) providing a sufficient force for reexpansion of the ring (3) and preventing its deformation when being inserted into the bowel lumen. The inner ring (3) continues along its entire circumference into the tube (4) whose thin walls are made of a material with similar characteristics as the inner ring (3). The diameter of an unstretched tube (4) is a little smaller than the diameter of the inner ring (3). The length of the tube (4) in this embodiment is a little smaller than the thickness of the abdominal wall (2). At the end lying opposite to the inner ring (3) the tube (4) continues into a faceplate (5) which is preferably of circular form and made of firm material or dimensioned so that it is firm yet pliable. The plate (5) has an opening in the centre in which the cover (8) is inserted which prevents the faeces from escaping."

Additional background art includes U.S. Pat. No. 6,033,390 (to von Dyck), U.S. Pat. No. 4,338,937A (to Lerman Sheldon), U.S. Pat. No. 4,534,761A (to Raible Donald), and EP 2027835A1 (to Axelsson el al).

SUMMARY OF THE INVENTION

According to an aspect of some embodiments of the present invention, there is provided a stomal insert for conducting waste content from an intestinal portion in an abdominal cavity through a stoma in an abdominal wall comprising; a cover for covering the stoma; a fixation element for anchoring the stomal insert to a visceral side of the abdominal wall; and a pliable, axially elastic tube interconnecting the cover and the fixation element and sized to apply a tensile force to the cover and to the fixation element.

According to some embodiments, a tension in the elastic tube ranges between approximately 1 gram to 400 grams.

According to some embodiments, a tension in the elastic tube ranges between approximately 1 gram to 200 grams.

According to some embodiments, a tension in the elastic tube ranges between approximately 3 grams to 50 grams.

According to some embodiments, the stomal insert further comprises a cap for sealing an opening to the elastic tube.

According to some embodiments, the cap includes a shell for accommodating a waste content collection bag. According to some embodiments, the cap includes a tab for removing the cap from the opening.

According to some embodiments, the elastic tube includes a material of durometer ranging from 5 to 50 shore A for providing the axial elasticity. According to some embodiments, the elastic tube comprises a material of durometer ranging from 20-30 shore A.

According to some embodiments, a portion of the elastic tube is adapted to bend for allowing relative motion between the cover and the fixation element.

According to some embodiments, the elastic tube is collapsible for allowing peristaltic propelling of waste content.

According to some embodiments, the fixation element includes a material of a durometer ranging from 5 to 50 Shore A.

According to some embodiments, the fixation element is a balloon.

According to some embodiments, the balloon includes a toroidal shape.

According to some embodiments, the toroidal shape includes a ring with a non-circular cross-section.

According to some embodiments, the balloon includes a material of a durometer ranging from 3 to 7 Shore A.

According to some embodiments, the balloon includes a seamless exterior surface.

According to some embodiments, the fixation element is deformable in an axial direction when pressed against the abdominal wall for maintaining a pressure on the abdominal wall.

According to some embodiments, the pressure ranges from 1 to 200 mmHg.

According to some embodiments, the pressure ranges from 20 to 150 grams.

According to some embodiments, the pressure ranges from 20 to 100 grams.

According to some embodiments, the cover includes an elastic material of a durometer ranging from 5 to 50 Shore A.

According to some embodiments, the cover includes an elastic material of a durometer ranging from 20 to 40 Shore A.

According to some embodiments, the cover is adapted to elastically press against the abdominal wall.

According to some embodiments, the cover is deformable by 5 mm in an axial direction.

According to some embodiments, the cover is substantially mushroom-shaped.

According to some embodiments, the cover includes a shape which is adjustable to geometrical variations in abdominal wall thickness.

According to some embodiments, the stomal insert comprises an inflation port for administering an expansion fluid for inflating the inflatable balloon.

According to some embodiments, the stomal insert an inflation lumen for connecting the inflation port with the balloon.

According to some embodiments, the elastic tube includes an attachment mechanism for attaching a waste content collection bag.

According to some embodiments, the attachment mechanism includes a snap-and-fit arrangement for securing the waste content collection bag to the elastic tube.

According to an aspect of some embodiments of the present invention, there is provided an active gas filter mechanism for filtering gases in a stomal insert, the stomal insert comprising a cover for covering the stoma, a fixation element for anchoring the stomal insert to a visceral side of the abdominal wall, and a pliable, axially elastic tube interconnecting the cover and the fixation element and sized to apply a tensile force to the cover and to the fixation element.

According to some embodiments, the active gas filter mechanism includes a valve.

According to an aspect of some embodiments of the present invention, there is provided a method for preventing leakage from a stoma comprising inserting in a stoma a stomal insert comprising a cover, a fixation element, and an axially elastic tube interconnecting the cover and the fixation element and sized for pressing the cover and the fixation element to an abdominal wall; and sealing an opening into the elastic tube with a cap.

According to some embodiments, the method includes administering through an inflation port an expansion fluid for inflating the fixation element.

According to an aspect of some embodiments of the present invention, there is provided a stomal insert for conducting waste content from an intestinal portion in an abdominal cavity out a stoma in an abdominal wall consisting essentially of a cover for covering the stoma, a fixation element for anchoring the stomal insert to a visceral side of the abdominal wall, an axially elastic tube interconnecting the cover and the fixation element and sized to apply a tensile force to the cover and to the fixation element, and a cap for sealing an opening in the elastic tube.

According to an aspect of some embodiments of the present invention, there is provided an Ostomy port kit comprising a stomal insert comprising a cover for covering the stoma, a fixation element for anchoring the stomal insert to a visceral side of the abdominal wall, and a pliable, axially elastic tube interconnecting the cover and the fixation element and sized to apply a tensile force to the cover and to the fixation element.

According to some embodiments, the Ostomy port kit includes a cap for attaching to the cover, which is optionally elastic, for sealing an opening into the elastic tube.

According to some embodiments, the Ostomy port kit includes a fluid injector for attaching to an inflation port on the stomal insert for administering an expansion fluid to the fixation element, for example, a balloon.

According to some embodiments, the Ostomy port kit includes at least one waste collection bag.

According to some embodiments, the elastic tube, the cover, and the fixation element are integrally formed in the stomal insert.

According to some embodiments, further comprises an integral waste collection bag.

According to an aspect of some embodiments of the present invention, there is provided a method for preventing leakage from a stoma on an abdominal wall comprising applying tension to a cover and a fixation element on opposing sides of the stoma with a collapsible pliable tube.

According to an aspect of some embodiments of the present invention, there is provided a stomal insert cap comprising a shell and a waste content collection bag fittedly accommodated in the shell wherein the waste content collection bag is deployable from the shell upon sensing of an intra-colonic pressure of approximately 100 mmHg or greater.

According to some embodiments, the waste collection bag is deployed through a removable cover.

According to an aspect of some embodiments of the present invention, there is provided A stomal insert cap comprising a deformable cover for providing a visual indication of an intra-colonic pressure of approximately 100 mmHg or greater.

According to an aspect of some embodiments of the present invention, there is provided a single-component stomal insert comprising a cover for covering the stoma; a fixation element for anchoring the stomal insert to a visceral side of the abdominal wall; and a pliable, axially elastic tube interconnecting the cover and the fixation element and sized to apply a tensile force to the cover and to the fixation element; wherein the cover, the fixation element, and the elastic tube are integrally formed together from a same material.

According to some embodiments, the single-component stomal insert further comprises an integrally formed waste content collection bag.

According to an aspect of some embodiments of the present invention, there is provided a method of pre-forming a balloon for use with a stomal insert comprising forming a balloon in a mold having a cavity shaped to a desired geometry of the balloon, removing the balloon from the mold, and turning the balloon inside-out for concealing a parting line in the balloon.

According to an aspect of some embodiments of the present invention, there is provided a method of seamlessly joining a balloon to and an elastic tube for producing a stomal insert comprising wrapping the elastic tube over a rigid mandrel, pressing an edge of the balloon against an external surface of the elastic tube, and joining the edge against the external surface.

According to some embodiments, joining includes bonding.

According to some embodiments, joining includes welding.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In general, similar numbers are used for similar elements in different figures.

In the drawings:

Figure 1:
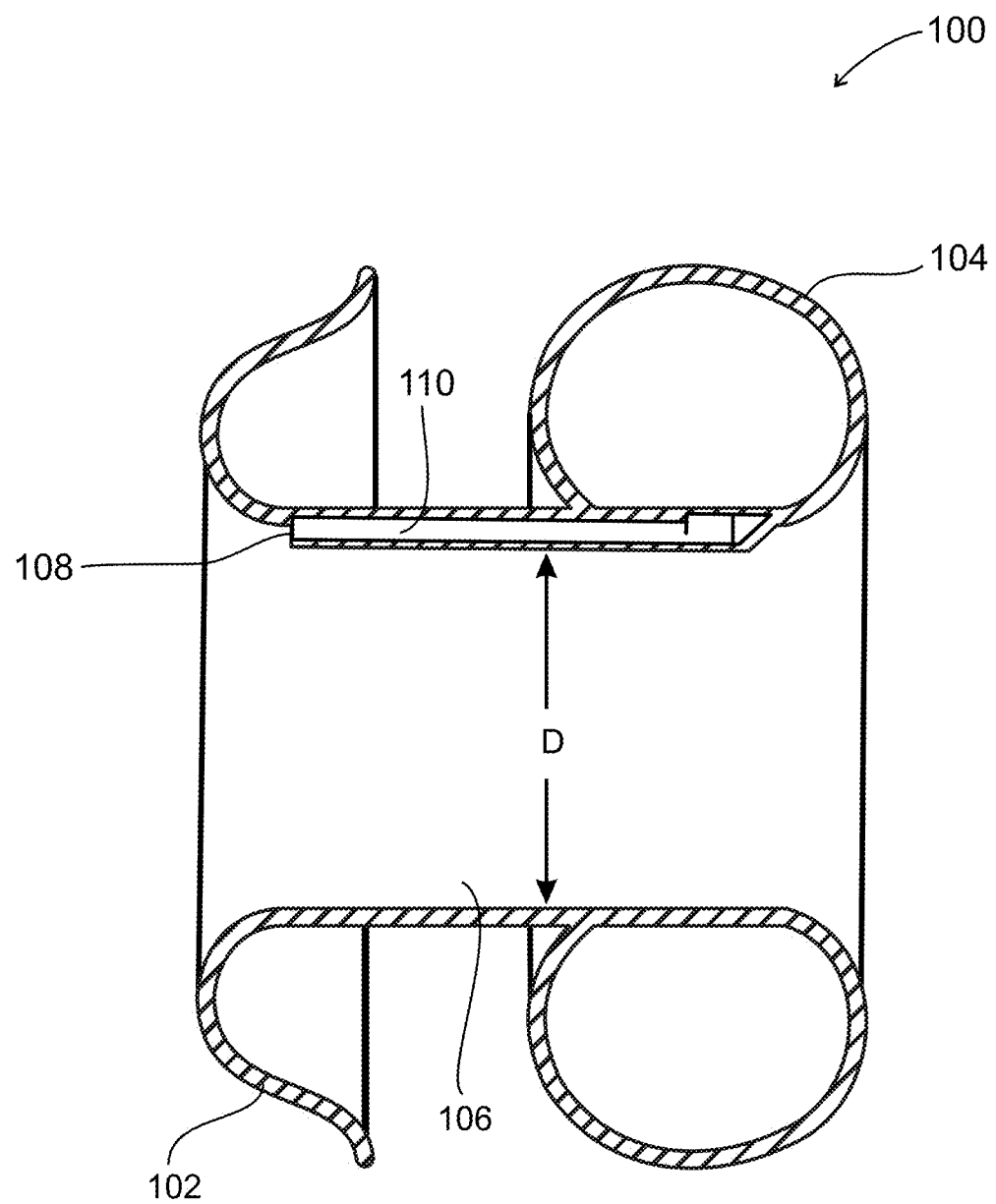
Figure 2A:
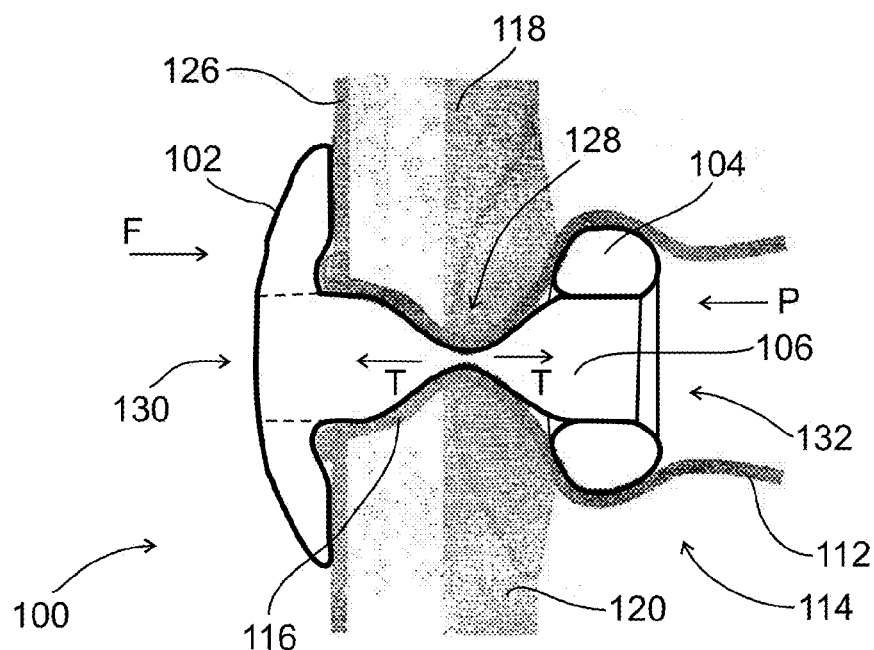
Figure 2B:
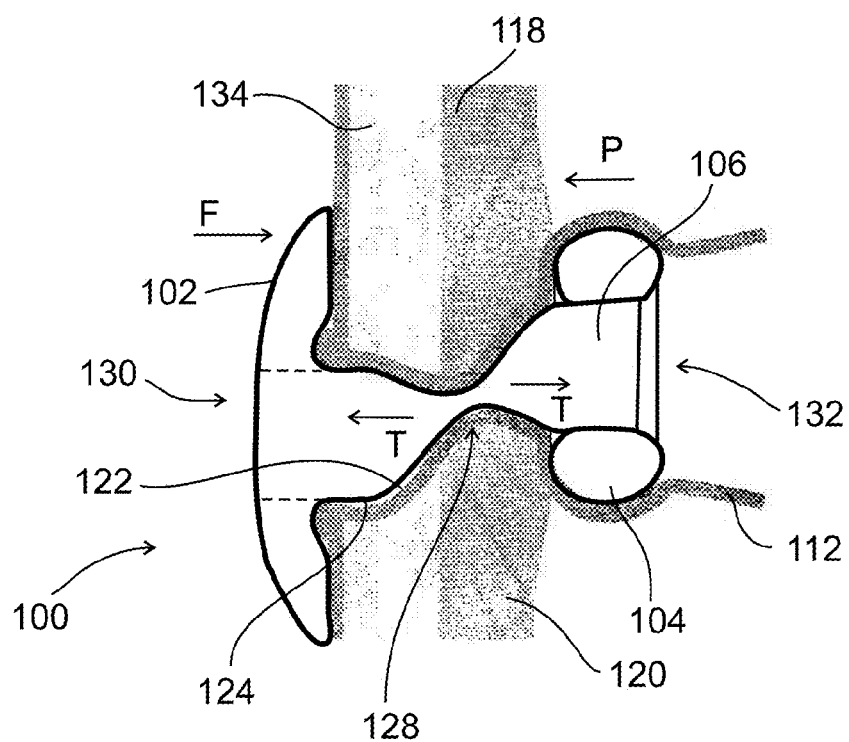
Figure 2C:
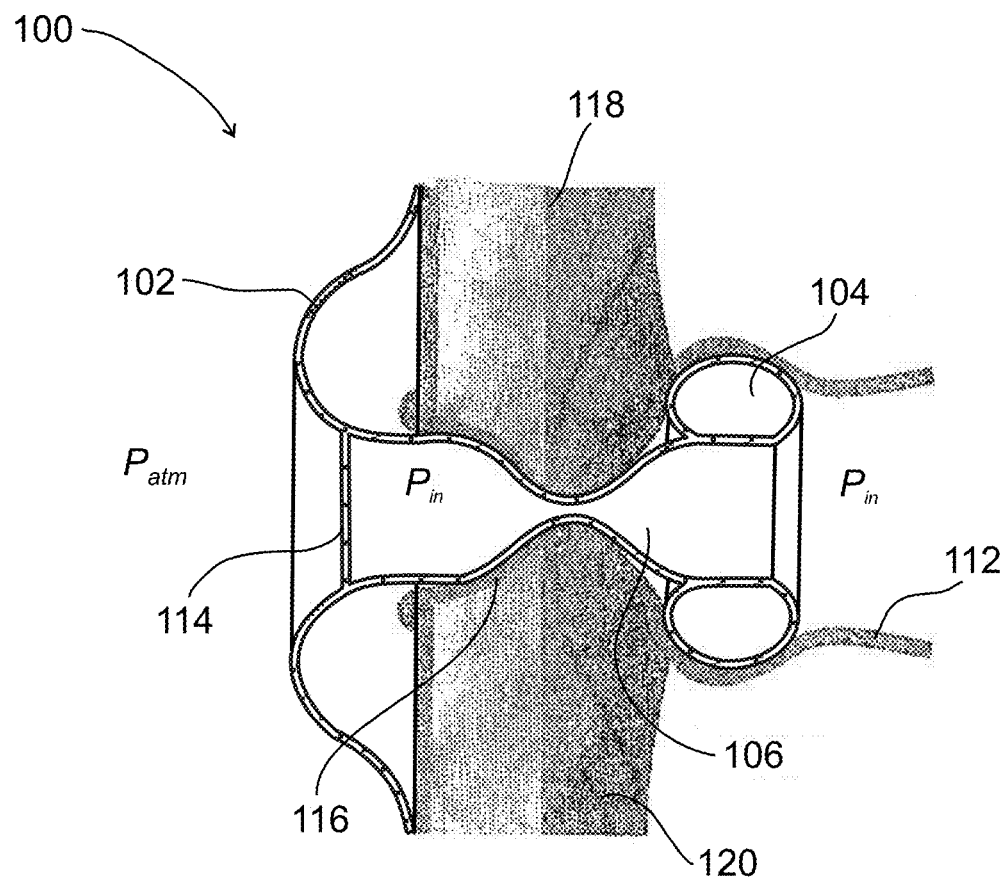
Figure 4A:
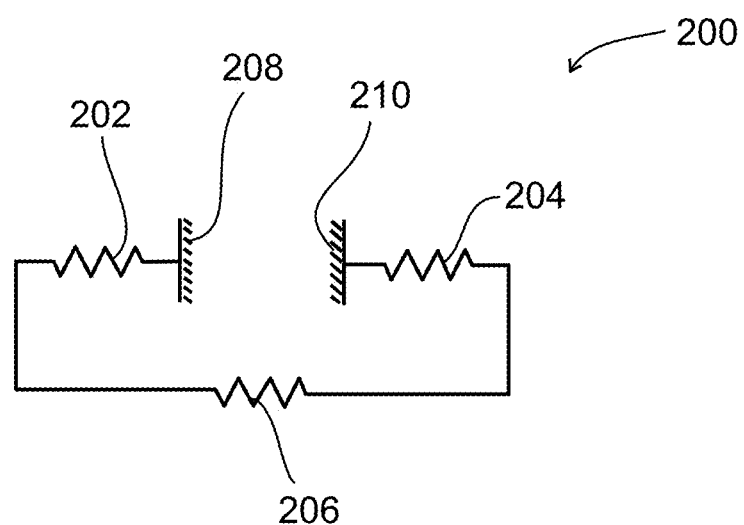
Figure 4B:
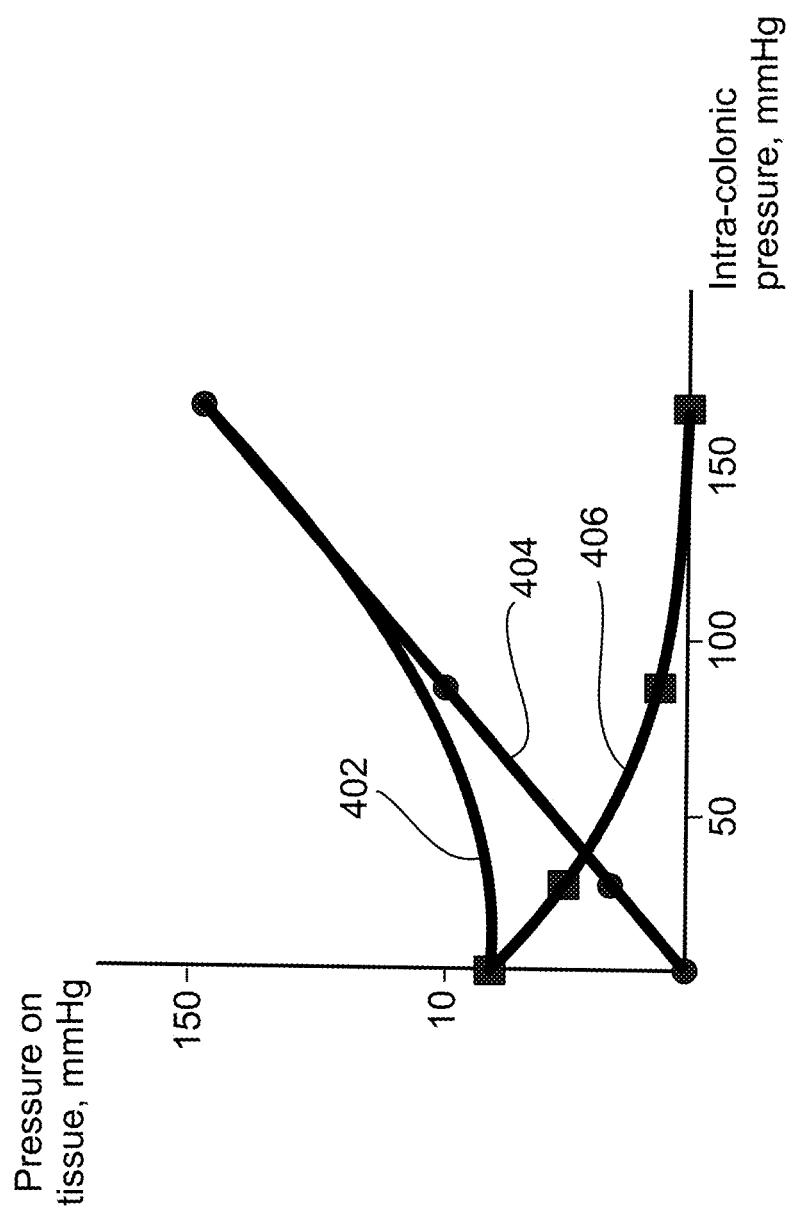
Figure 5B:
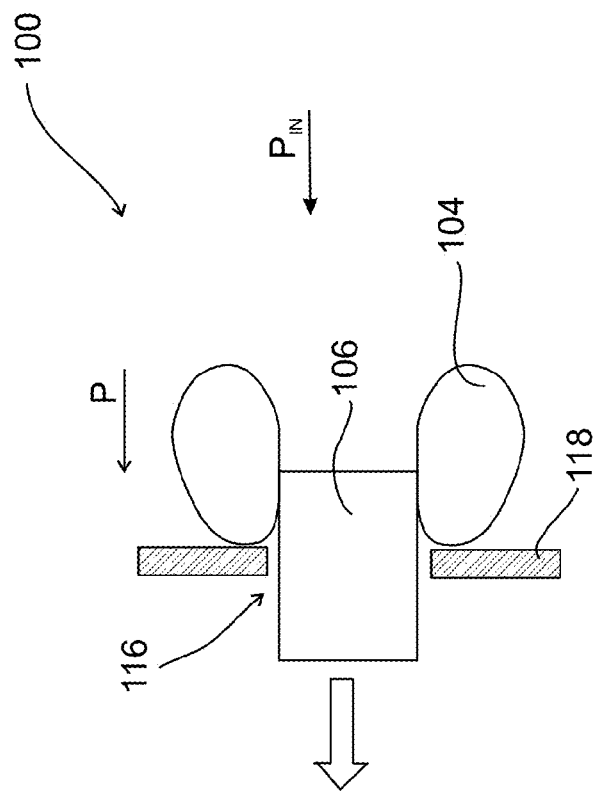
Figure 5A:
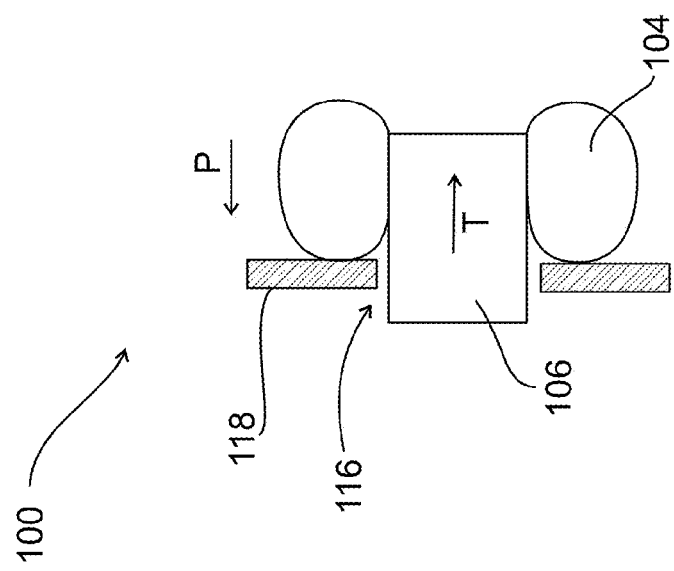
Figure 6A:
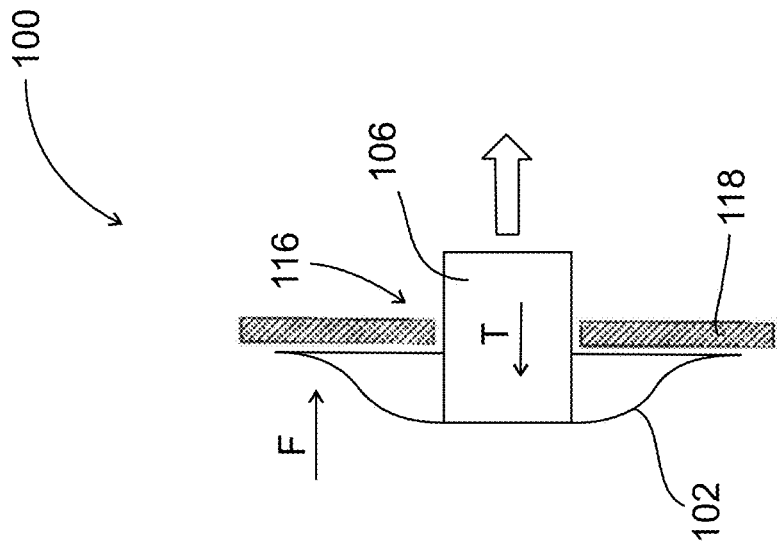
Figure 6B:
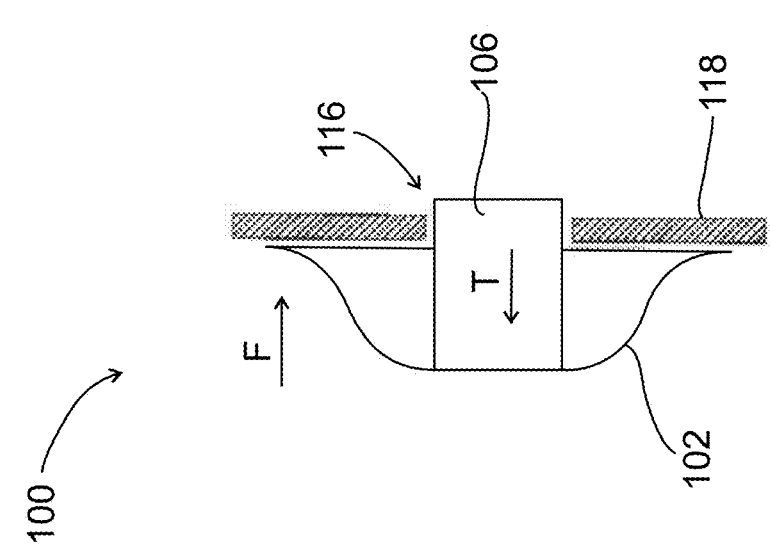
Figure 7A:
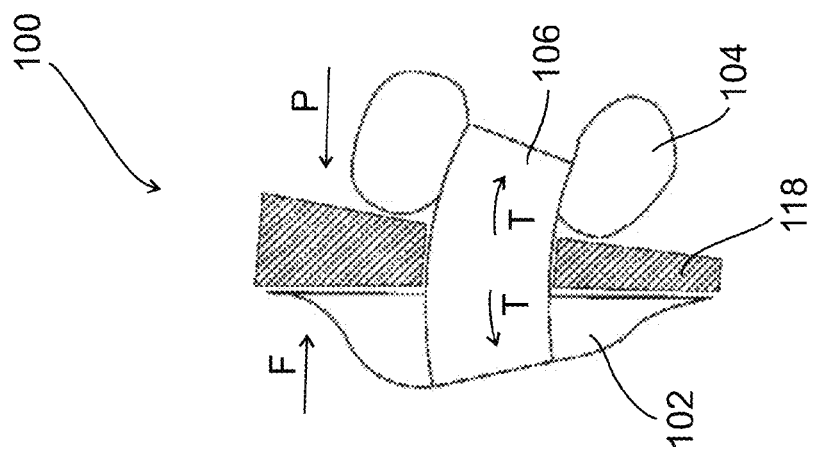
Figure 7B:
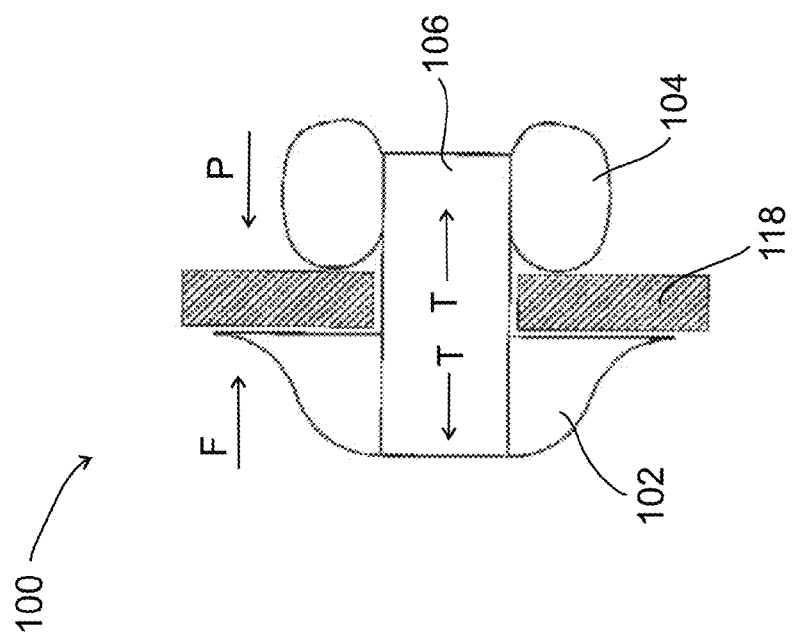
Figure 8:
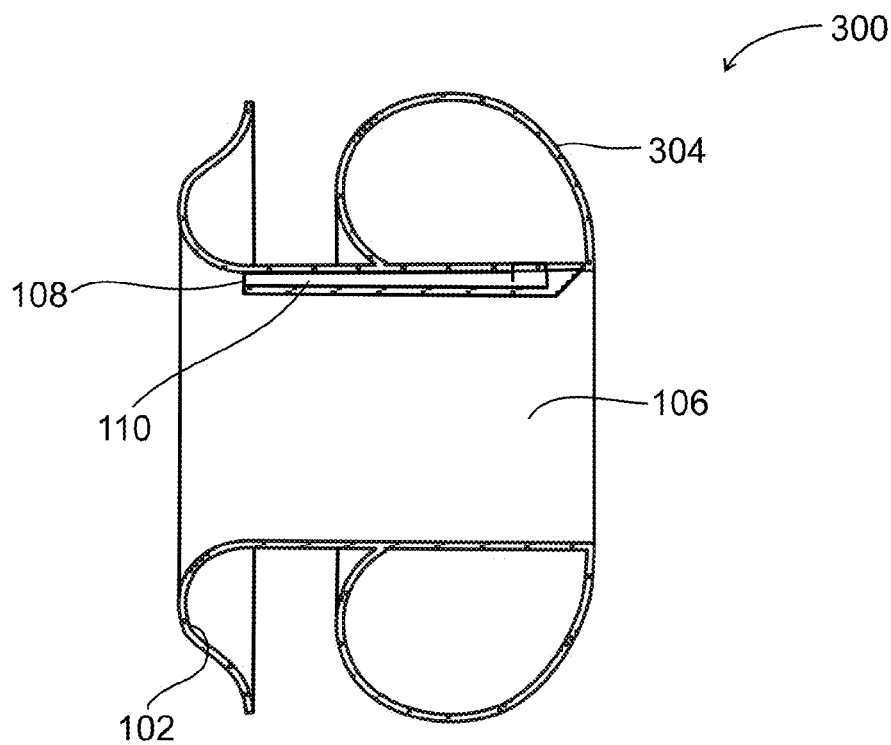
Figure 9:
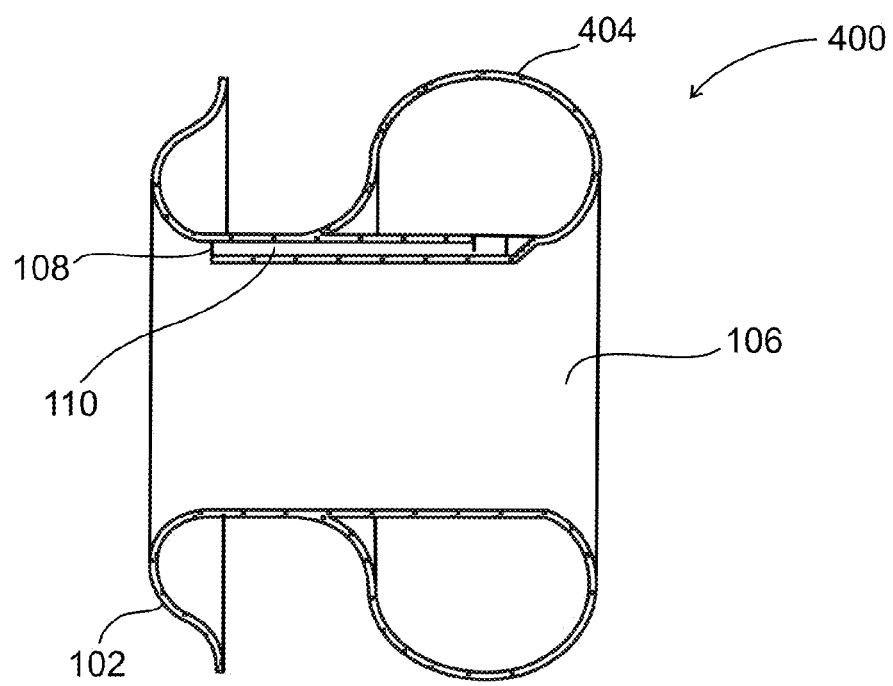
Figure 10A:
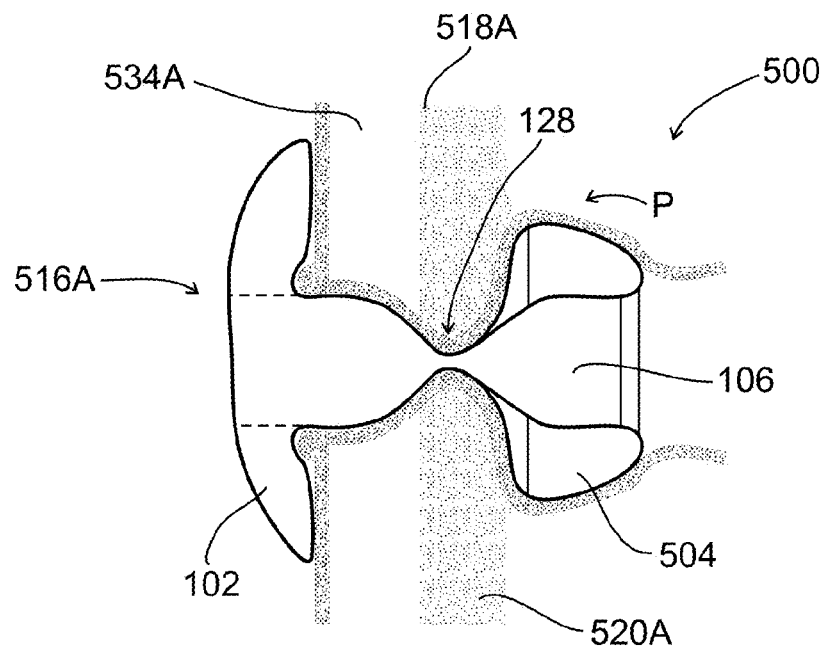
Figure 10B:
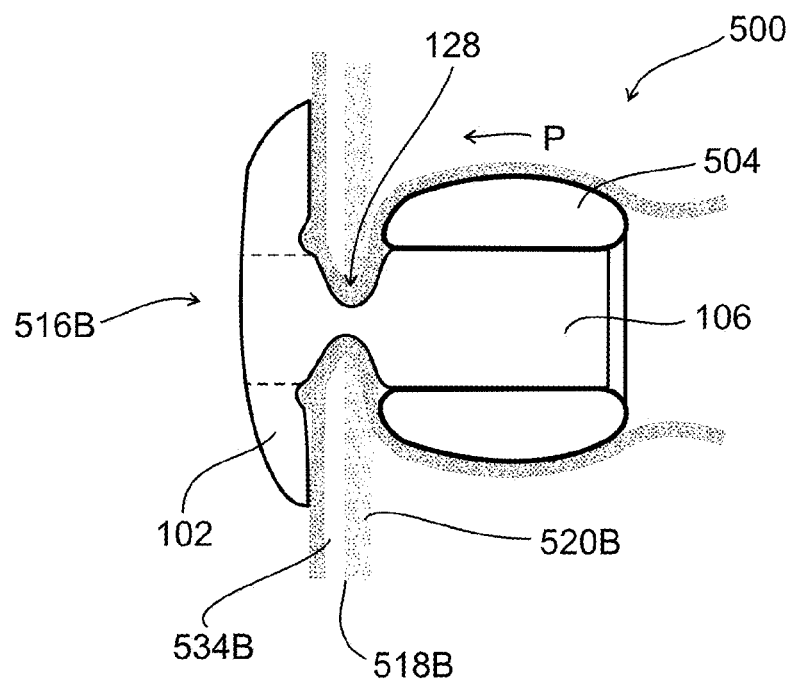
Figures 11A, 11B, 11C:
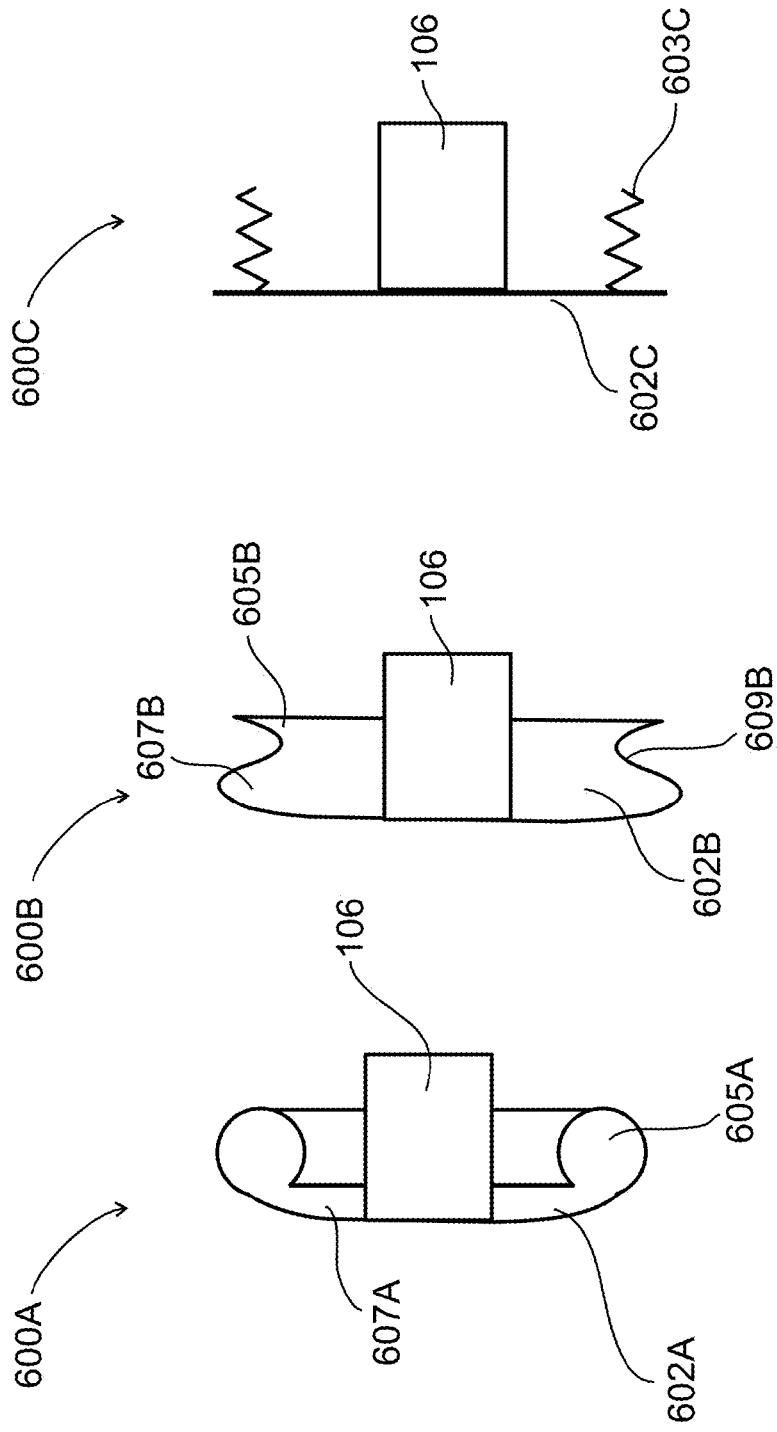
Figure 12A:
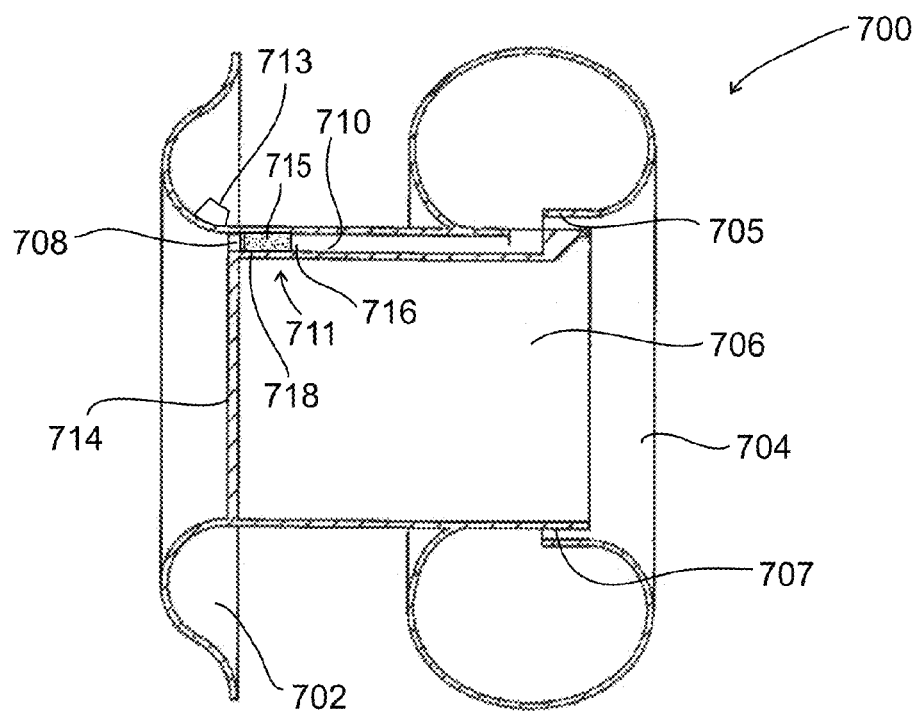
Figure 13:
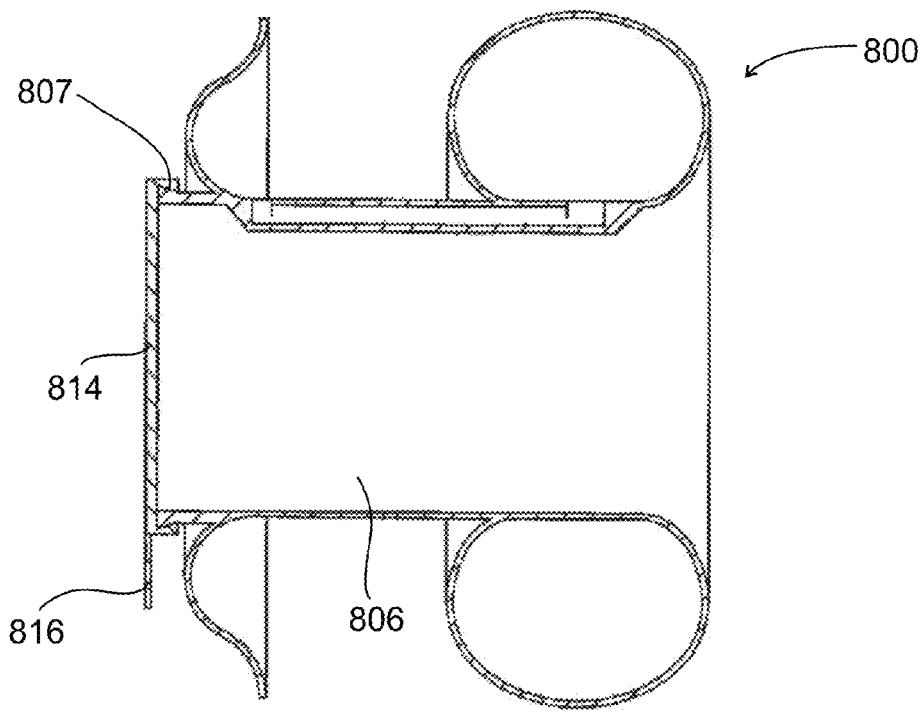
Figure 12B:
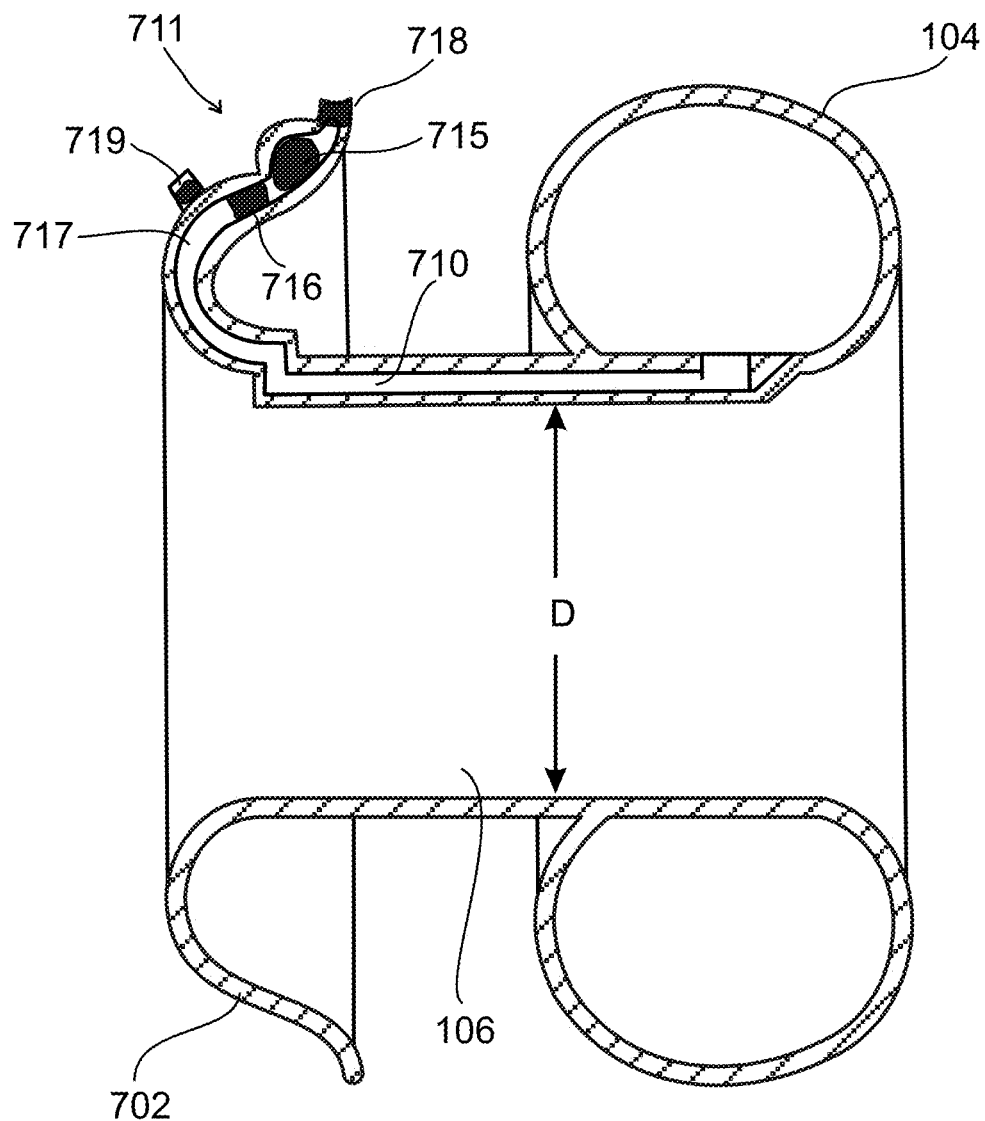
Figure 12C:
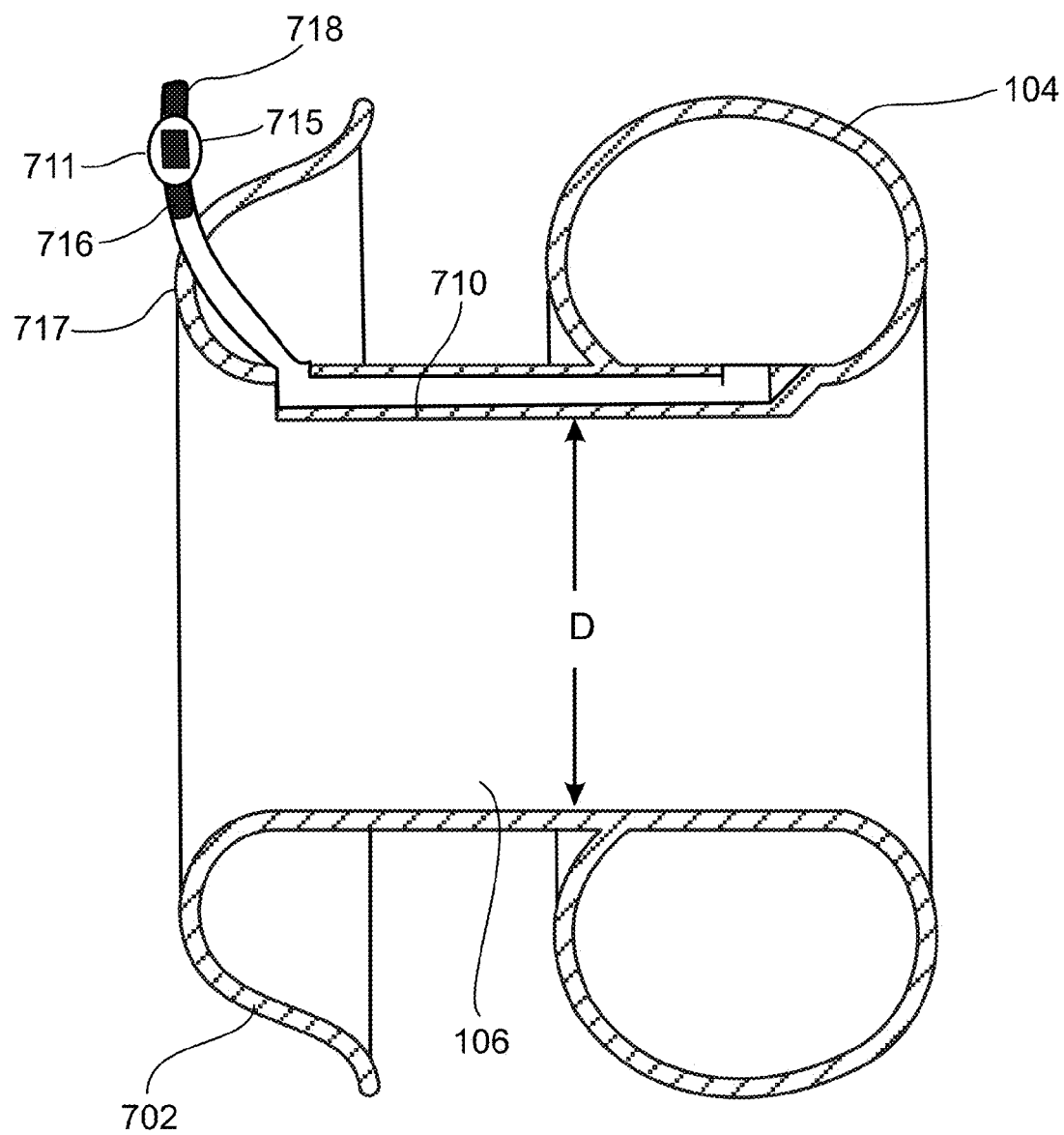
Figure 14:
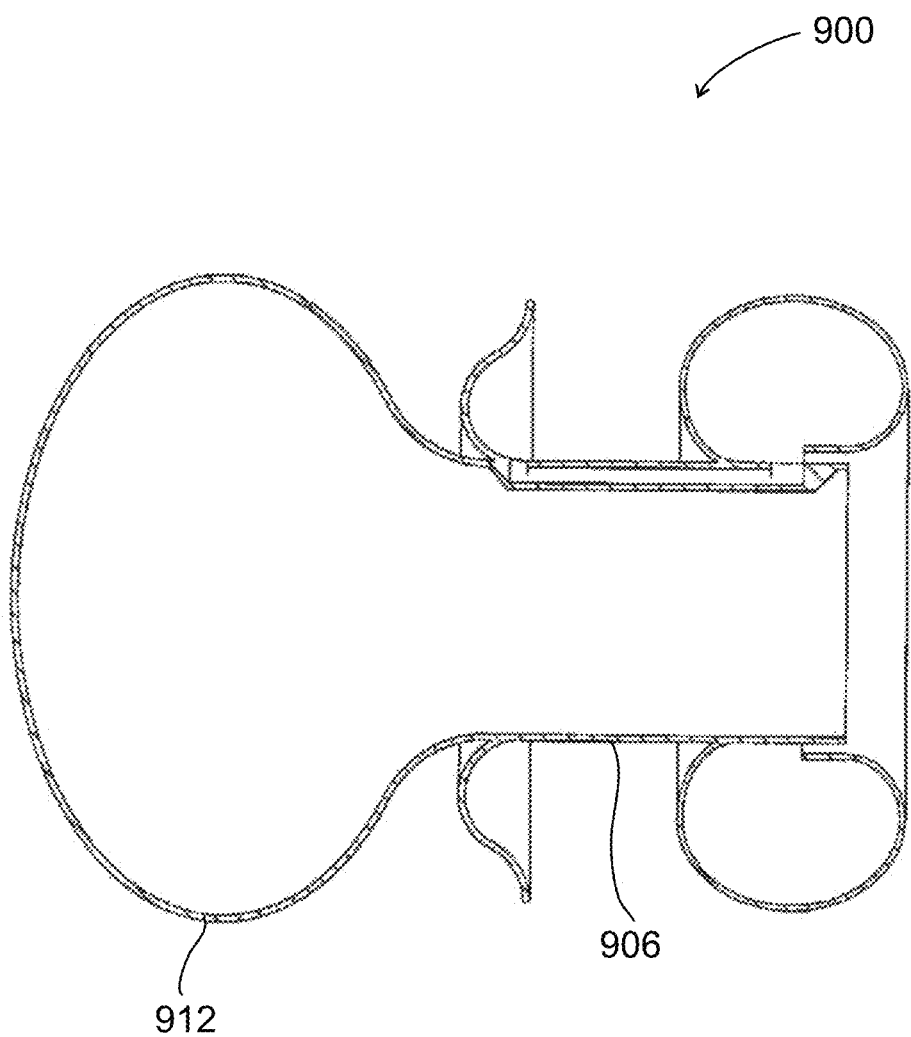
Figure 15A:
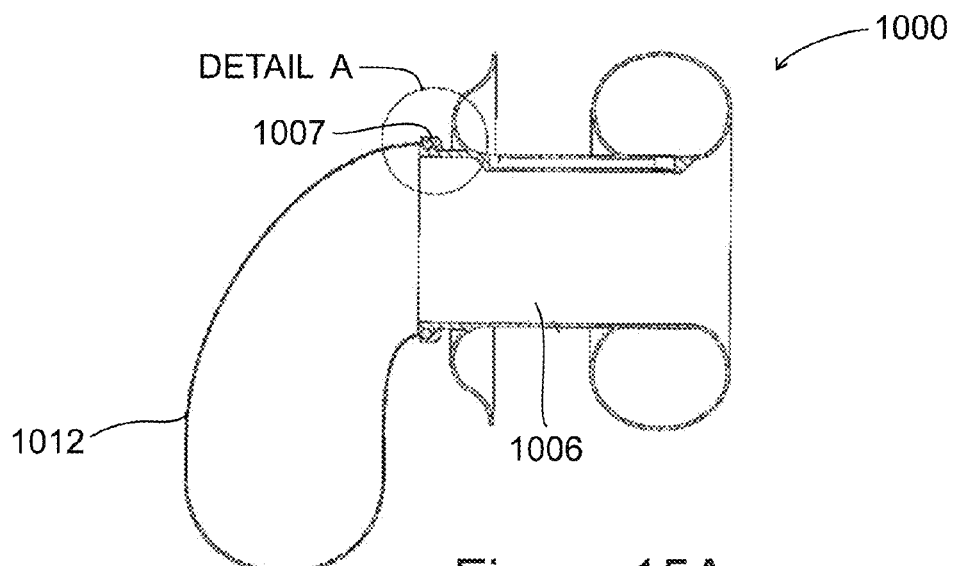
Figure 15B:
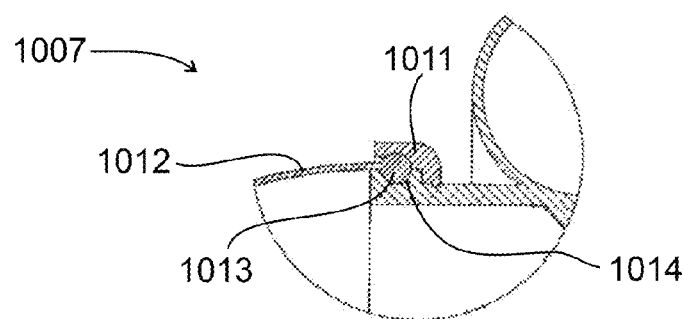
Figure 15C:
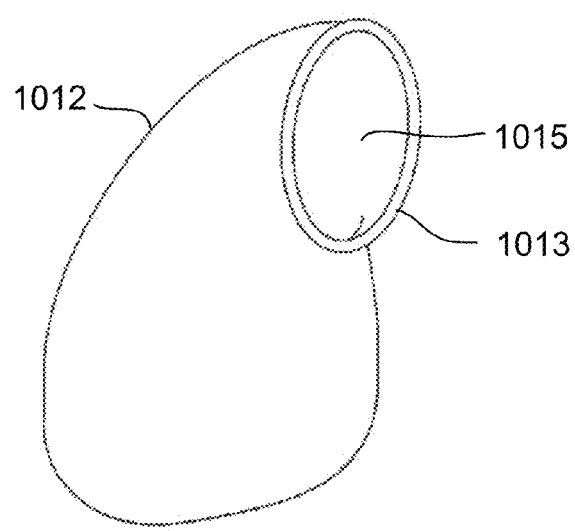
Figure 16A:
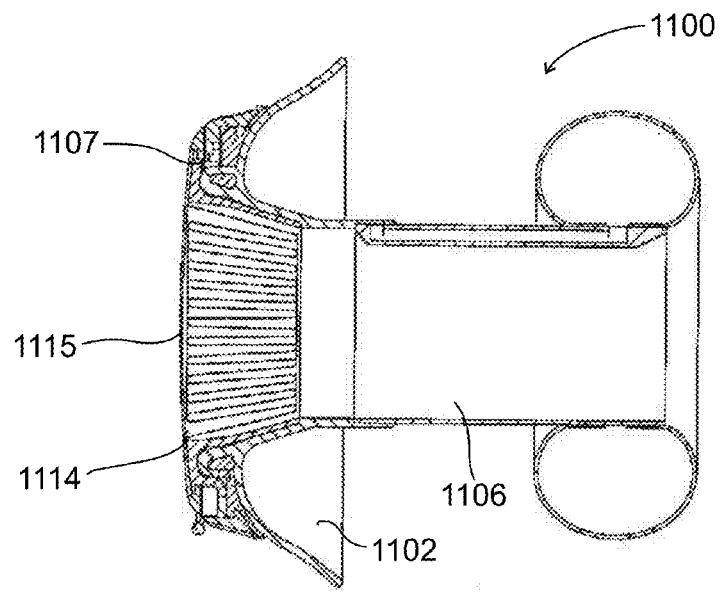
Figure 16B:
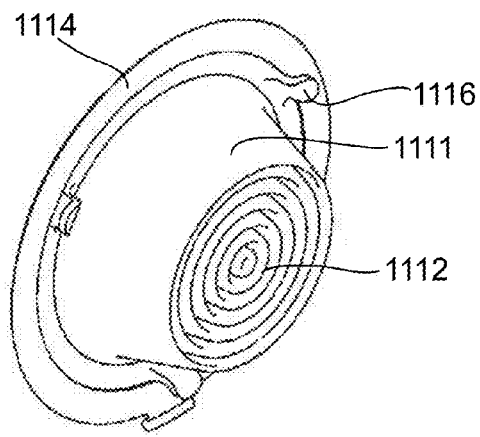
Figure 16C:
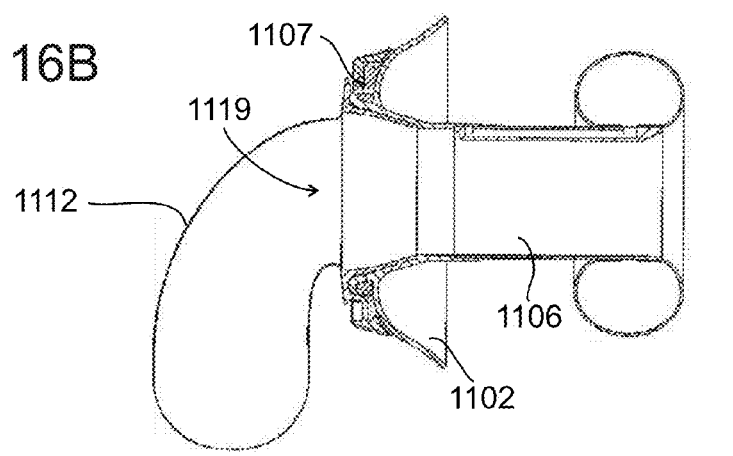
Figure 17A:
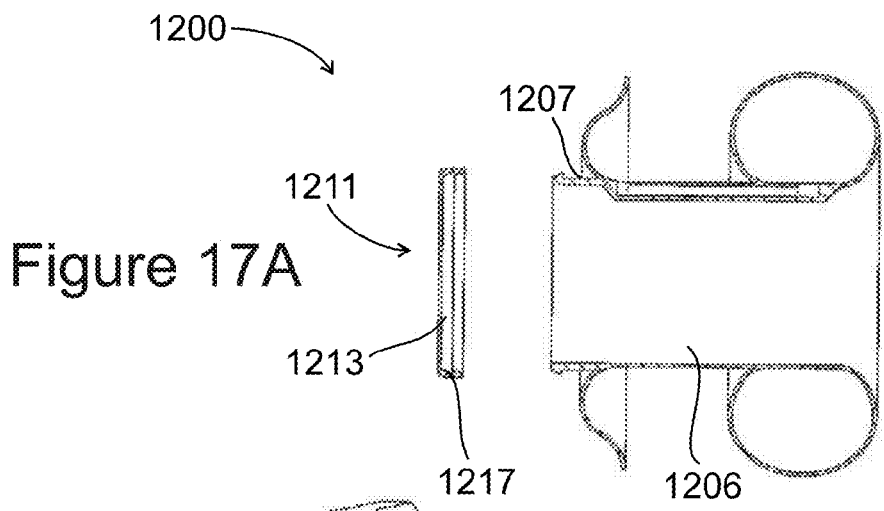
Figure 17B:
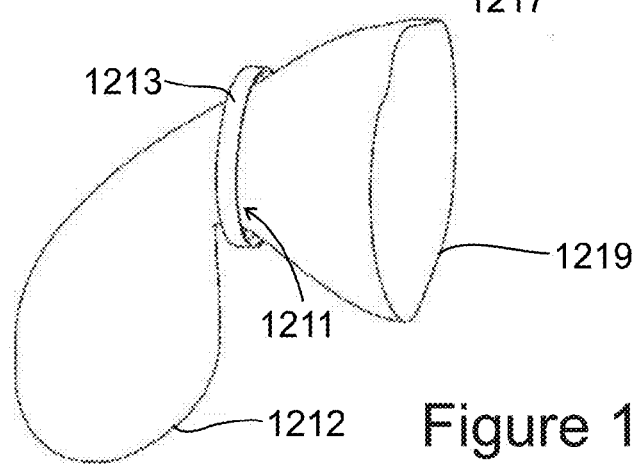
Figures 17C, 17D:
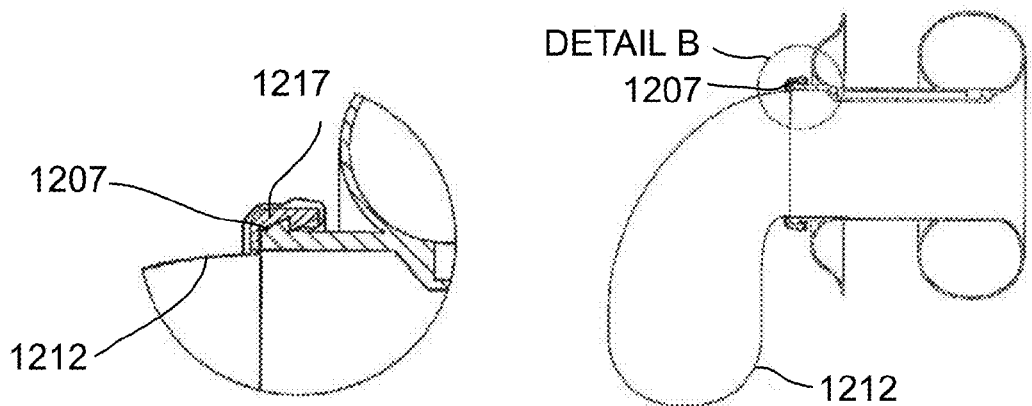
Figure 18:
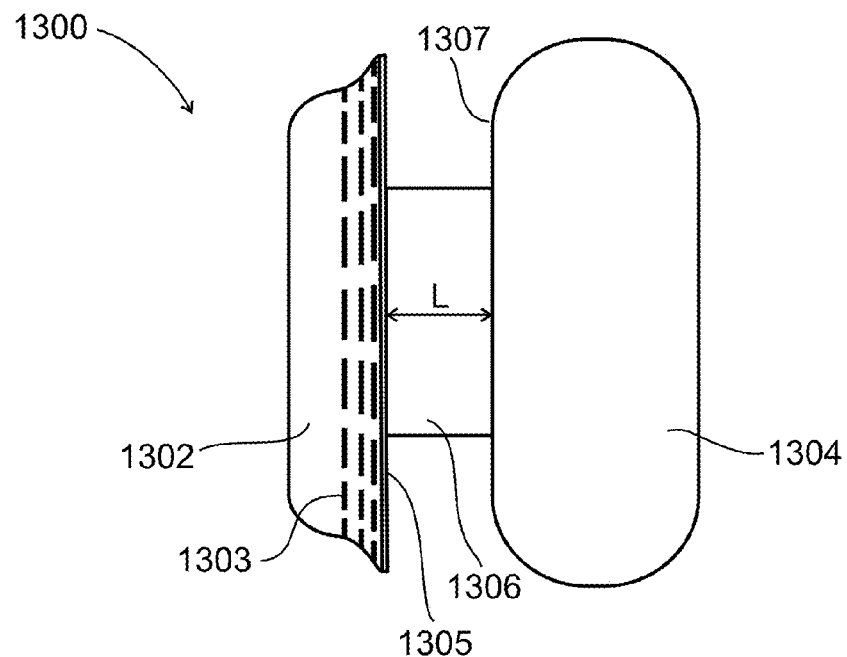
Figure 19:
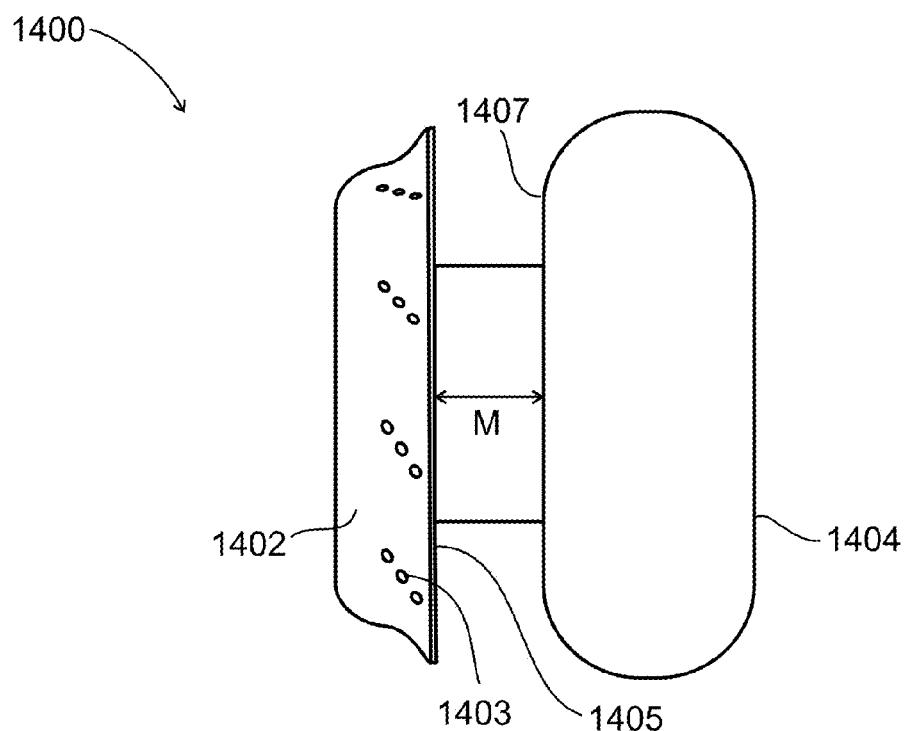
Figures 20A, 20B:
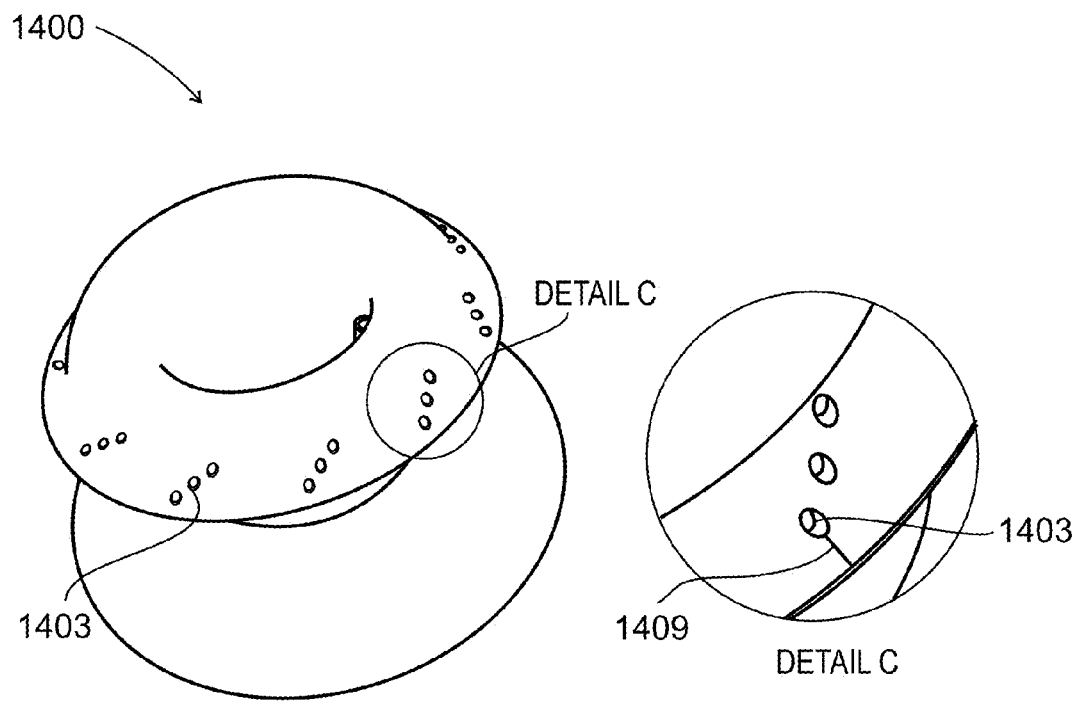
Figure 20C:
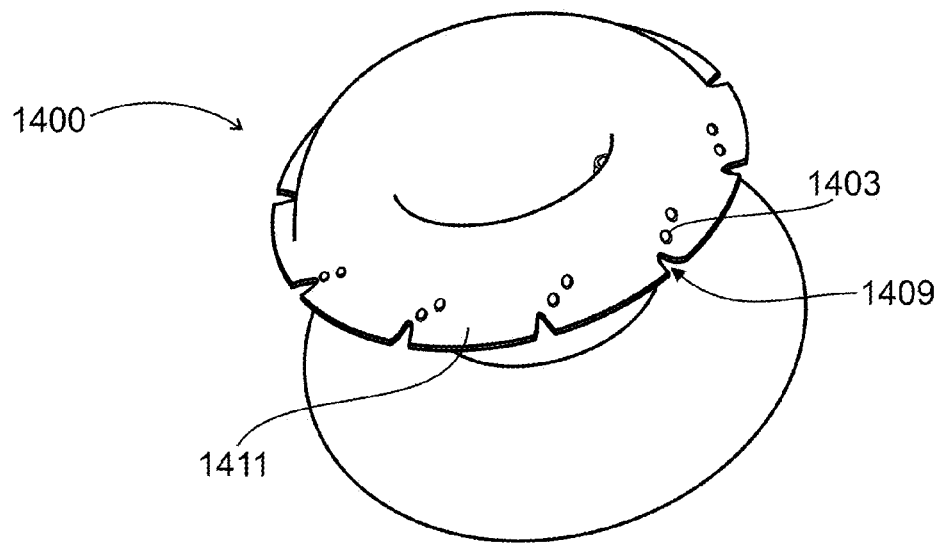
Figure 21:
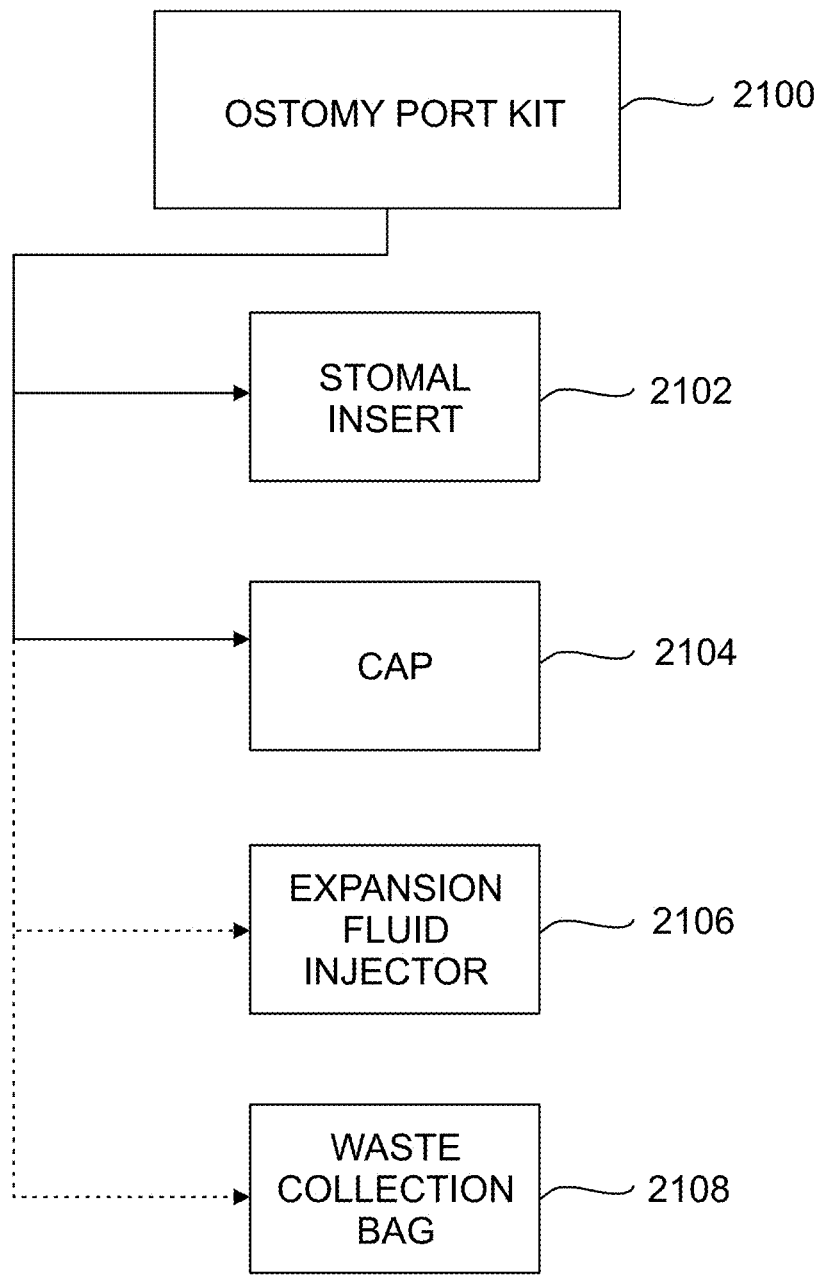
Figure 22:
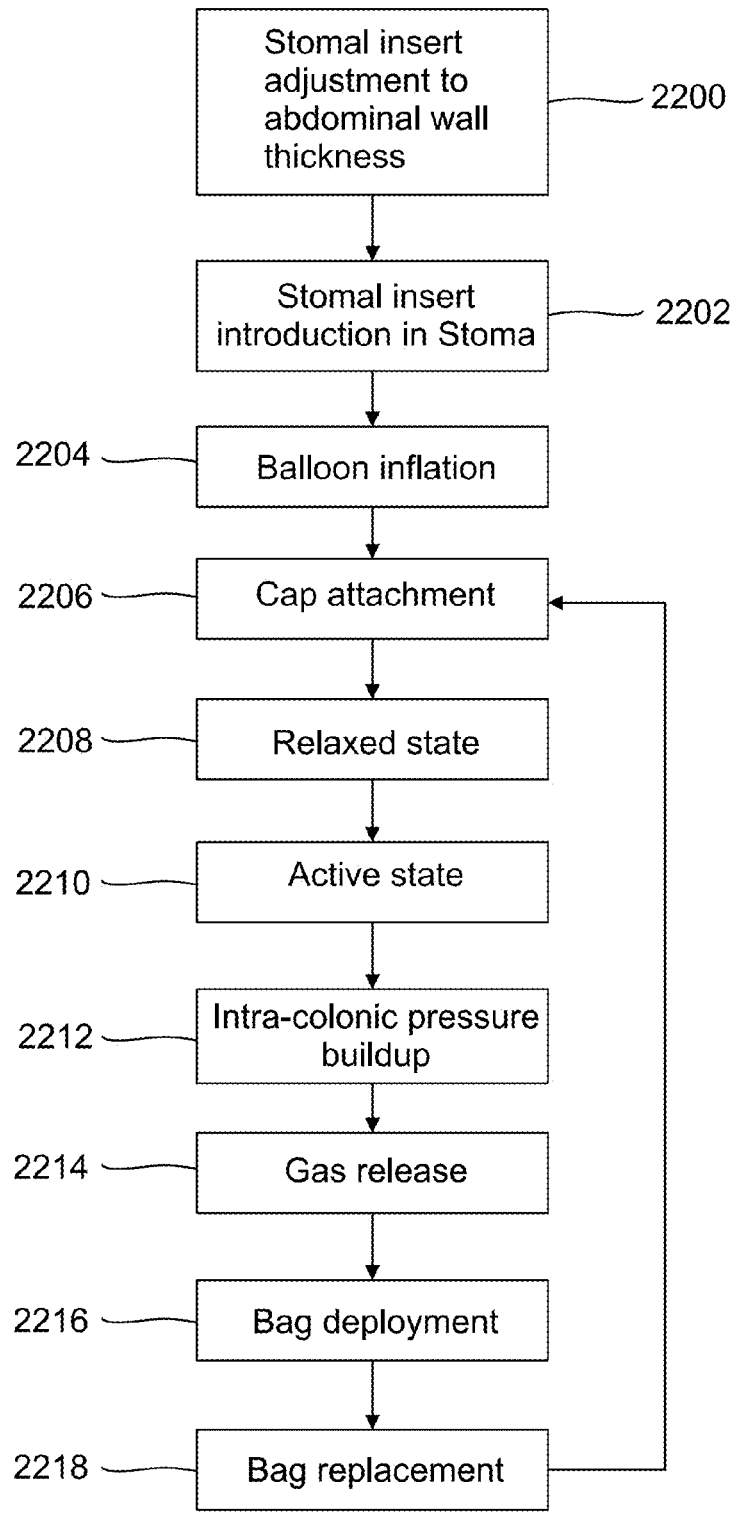
Figure 26:
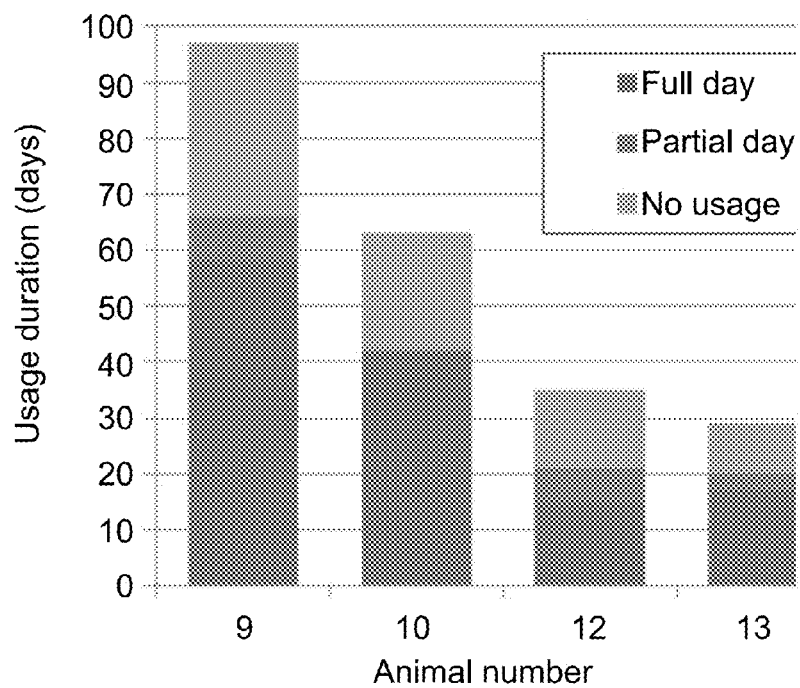
Figure 27:
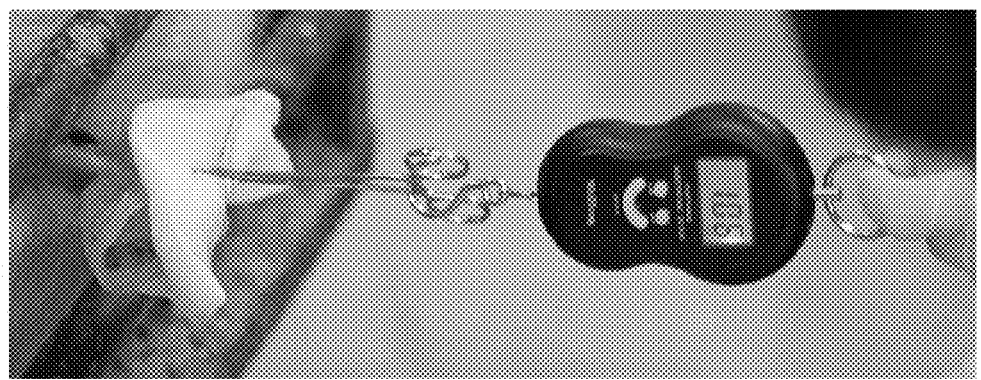
Figures 28A, 28B:
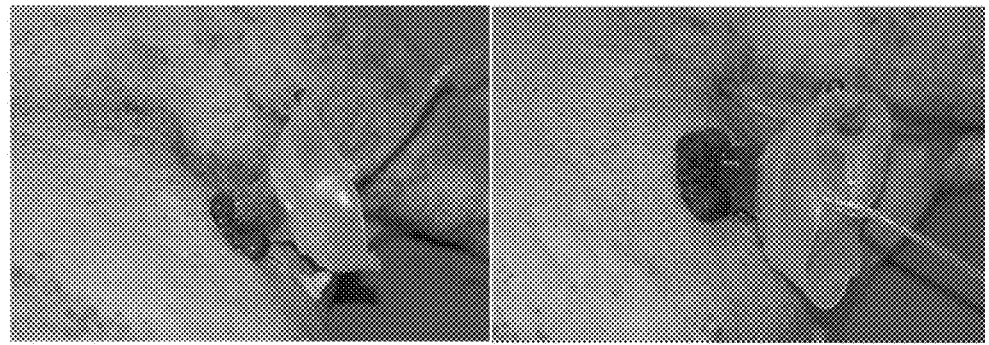
Figure 29:
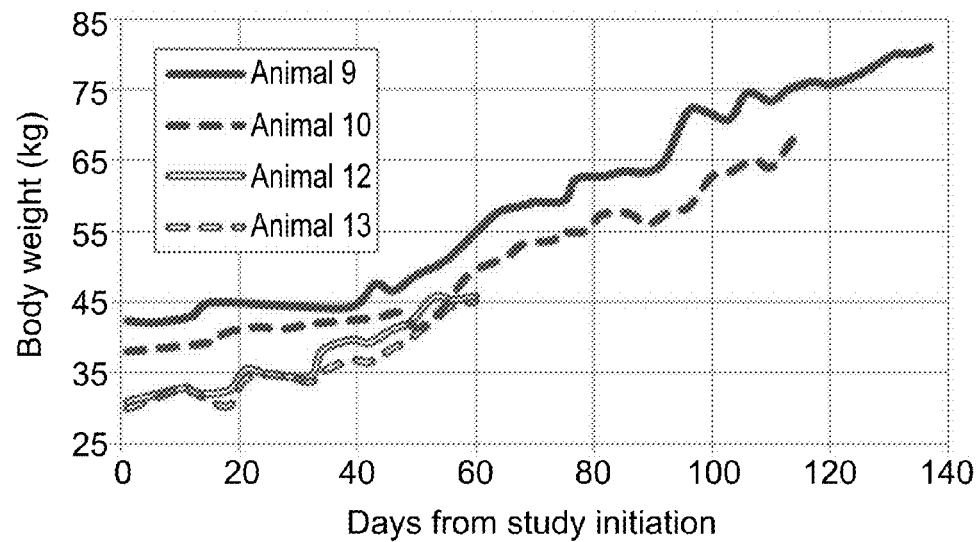
Figure 32A:
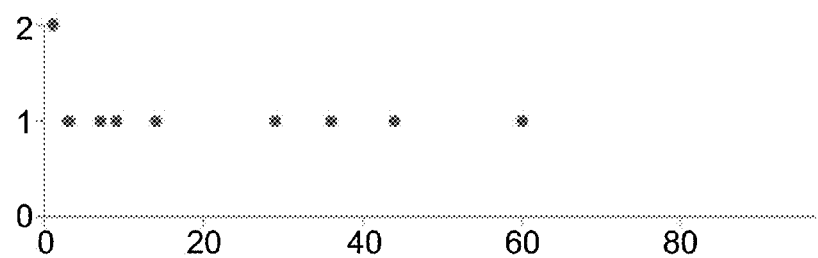
Figure 32B:
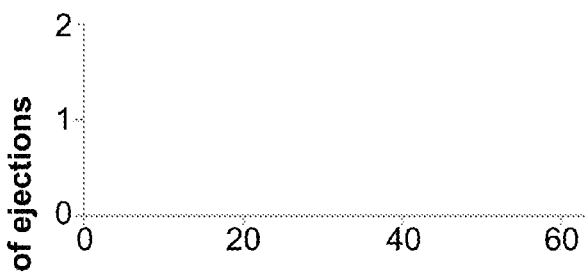
Figure 32C:
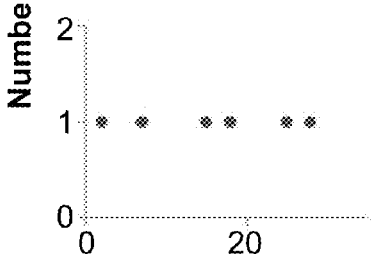
Figure 32D:
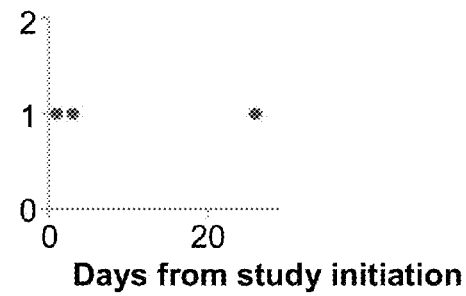
Figure 33:
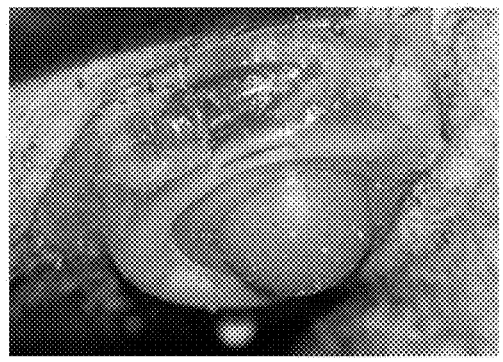
Figure 34:
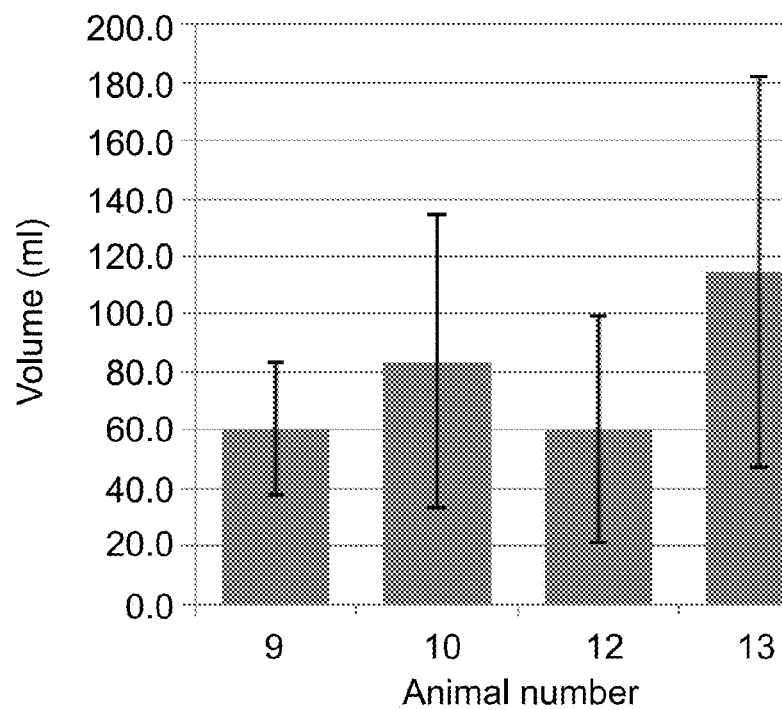

FIG. 1 schematically illustrates a stomal insert, according to an embodiment of the present invention;

FIG. 2A schematically illustrates the stomal insert inserted in a stoma with an intestinal portion fitted over the stomal insert and attached to an abdominal wall exterior; according to an embodiment of the present invention;

FIG. 2B schematically illustrates the stomal insert inserted in the stoma in an deformed state where the geometry of abdominal wall has undergone a variation due to a change in body posture or body movement, according to an embodiment of the present invention;

FIG. 2C schematically illustrates the stomal insert inserted in the stoma and pressing against the abdominal wall sealing the stoma, under the influence of intra-colonic pressure, according to some embodiments of the present invention;

FIGS. 3A and 3B schematically show a side view of the stomal insert and a cross-sectional view A-A of a crimped elastic tube section, respectively, according to an embodiment of the present invention;

FIG. 4A schematically illustrates a spring system model of the stomal insert, according to some embodiments of the present invention;

FIG. 4B is a graphical representation illustrating design goal values for a pressure exerted by a balloon in the stomal insert, optionally determined using the model of spring system, according to some embodiments of the present invention;

FIG. 5A schematically illustrates the interplay in the deformation of the balloon and the elastic tube in a first scenario wherein the elastic component of the pressure exerted by the balloon is due to a tensile force predominating over the intra-colonic pressure component, according to some embodiments of the present invention;

FIG. 5B schematically illustrates the interplay in the deformation of the balloon and the elastic tube in a second scenario wherein the intra-colonic pressure component of the pressure exerted by the balloon predominates over the elastic component, according to some embodiments of the present invention;

FIG. 6A schematically illustrates the interplay in the deformation of the elastic cover and the elastic tube in a first scenario wherein the user is in the relaxed state, according to some embodiments of the present invention;

FIG. 6B schematically illustrates the interplay in the deformation of the elastic cover and the elastic tube in a second scenario wherein user movement results in a variation in the abdominal geometry, according to some embodiments of the present invention;

FIG. 7A schematically illustrates the interplay in the deformation of the elastic cover, the balloon, and the elastic tube, in a first scenario wherein the user is in the relaxed state, according to some embodiments of the present invention;

FIG. 7B schematically illustrates the interplay in the deformation of the elastic cover, the balloon, and the elastic tube, in a second scenario wherein user movement results in variations in the abdominal geometry, according to some embodiments of the present invention;

FIG. 8 schematically illustrates a stomal insert including an elastic cover, an elastic tube, an inflation port, and an inflation lumen, according to some embodiments of the present invention;

FIG. 9 schematically illustrates a stomal insert including an elastic cover, an elastic tube, an inflation port, and an inflation lumen, according to some embodiments of the present invention;

FIGS. 10A and 10B schematically illustrate a stomal insert adapted to be inserted in stomas formed in abdominal walls varying in thickness from one user to another, according to some embodiments of the present invention;

FIGS. 11A-11C schematically illustrate different embodiments of stomal inserts similar to the stomal insert of FIG. 1 having different elastic stomal covers, respectively, according to some embodiments of the present invention;

FIG. 12A schematically illustrates a stomal insert including an elastic stomal cover, an inflatable balloon, an elastic tube, an inflation port, and an inflation lumen, all integrally formed as a single component suitable for one-time use, according to some embodiments of the present invention;

FIGS. 12B and 12C show alternative embodiments for a port including an integral pump, in accordance with exemplary embodiments of the invention;

FIG. 13 schematically illustrates a stomal insert with a removable cap for removing waste content, according to some embodiments of the present invention;

FIG. 14 schematically illustrates a stomal insert with a built-in collection bag for collecting waste content, according to some embodiments of the present invention;

FIGS. 15A-15C schematically illustrate a stomal insert including an attachment mechanism at a proximal end of an elastic tube, for attaching a collection bag, according to some embodiments of the present invention;

FIGS. 16A-16C schematically illustrate a stomal insert including an attachment mechanism at a proximal end of an elastic tube, for attaching a cap including a collection bag accommodated inside a shell, according to some embodiments of the present invention;

FIGS. 17A-17D schematically illustrate a stomal insert including an attachment mechanism at a proximal end of an elastic tube, for attaching a collection bag used in domestic applications, according to some embodiments of the present invention;

FIG. 18 schematically illustrates a stomal insert including an elastic stomal cover adjustable for use with users of variable abdominal wall thickness, according to some embodiments of the present invention;

FIGS. 19 and 20A-20C schematically illustrate a stomal insert including an elastic stomal cover adjustable for use with users of variable abdominal wall thickness, according to some embodiments of the present invention;

FIG. 21 schematically illustrates an Ostomy Port Kit, according to some embodiments of the present invention;

FIG. 22 is a flow chart showing operation of the stomal insert, according to some embodiments of the present invention;

FIG. 23 shows an exemplary Ostomy port used in a preclinical study, according to an embodiment of the present invention;

FIGS. 24A and 24B show a schematic view of the CapsuleCap™ with a cover, and with the cover removed, according to an embodiment of the present invention;

FIGS. 25A-25D show the steps of creating the ostomy in the preclinical study;

FIG. 26 graphically illustrates a distribution of device usage days during the preclinical study;

FIG. 27 shows a retaining test arrangement used during the preclinical study;

FIGS. 28A and 28B show the sealing test arrangement used during the preclinical study;

FIG. 29 graphically illustrates the variation in the body weight of the animals during the preclinical study;

FIGS. 30A and 30B show examples of the macro pathological evaluation conducted during the preclinical study;

FIGS. 31A and 31B show additional examples of the pathological evaluation;

FIGS. 32A-D graphically illustrate, in four sub-charts, the distribution of the unintended ejections of the ostomy port during the preclinical study;

FIG. 33 shows an example of the protruding cover of the cap due to fecal matter in the stomal insert, during the preclinical study;

FIG. 34 graphically represents an average volume of excrement discharged from the stoma upon removal of the device, during the preclinical study; and FIGS. 35A-35D show causes for device ejection during the preclinical study.

DESCRIPTION OF SPECIFIC EMBODIMENTS
OF THE INVENTION

The present invention, in some embodiments thereof, relates to the field of prosthetic implants, and more particularly, to an Ostomy port for use following Ostomy cases such as Colostomy, Ileostomy or Urostomy, or for fecal incontinence.

An aspect of some embodiments of the present invention relates to a flexible and elastic stomal insert. In some embodiments, the stomal insert is advantageously configured to substantially prevent leakage of waste content and associated odors through a stoma, independently of variations in a user's abdominal geometry. Optionally, the stomal insert substantially prevents leakage of waste content and associated odors independently of variations in an intra-colonic pressure in the user's intestinal portion, which may vary from 0-150 mmHg. Optionally, the stomal insert exerts a pressure on the intestinal portion equal to, or less than, the intra-colonic pressure when the intra-colonic pressure increases, substantially preventing compression-related injuries such as, for example, ischemia or necrosis. Geometric variations in the user's abdomen occur for any type of body movement, from minor movements associated with breathing up to major variations associated with activities such as, for example, practicing sports or bending over.

In an exemplary embodiment, the stomal insert is formed from three, elastic sections, an elastic stomal cover adapted to apply an axial force to an exterior of the user's abdomen for pressing the cover to the abdomen, an inflatable balloon adapted to exert an axial pressure to the visceral side of the abdomen pressing the balloon to the abdomen, and a pliable, axially elastic tensiled tube passing through the stoma and interconnecting the elastic cover with the balloon.

In some embodiments, the inflatable balloon is replaceable by any fixation element, elastic or non-elastic, or any combination thereof, suitable for axially pressing the intestinal portion against the abdominal wall while maintaining the sealing. Optionally, the elastic cover is replaceable by any cover, elastic or non-elastic, or any pressing against the external abdominal wall.

In an exemplary embodiment, the three sections form part of an elastic system which continuously maintains the seal between the insert and the intestinal portion, and prevents the insert from applying excessive pressure on body parts (e.g. abdominal wall, intestinal portion) with each component elastically deforming responsive to variations in the abdominal geometry and/or the intra-colonic pressure. Alternatively, the elastic system includes only one elastic component, the elastic tube. Alternatively, the elastic system includes only two elastic components, the balloon and the cover. Alternatively, the two elastic components are the balloon and the elastic tube.

According to some embodiments of the present invention, the cover and the balloon are pressed against the abdomen by a tensile (pulling) force exerted on each one of the components by the elastic tube when the intra-colonic pressure is substantially zero. Optionally, this attachment is independent of abdominal geometric variations. Optionally, the tensile force ranges from 20-400 grams, 80-350 grams, 100-300 grams, 130-270 grams, 170-230 grams, 190-210 grams. Optionally, this tensile force causes the balloon to exert a pressure on the abdominal wall in a range between 1 mmHg and 50 mmHg, inclusively, when the intra-colonic pressure is substantially zero. Optionally, the pressure exerted by the balloon is in a range between 3 mmHg and 40 mmHg, 7 mmHg and 25 mmHg, 12 mmHg and 18 mmHg. When the intra-colonic pressure is greater than zero, the increased intra-colonic pressure presses the balloon into the abdominal wall further securing the seal. The increase in the pressure exerted by the balloon on the abdominal wall is compensated by a decrease in the tensile force of the elastic tube as the balloon pushes the tube in a proximal direction away from the abdominal cavity. Optionally, the tensile force decreases to zero.

In some exemplary embodiments, the pressure exerted by the balloon against the abdominal wall is the same, or less than, the intra-colonic pressure. Optionally, a maximum pressure exerted by the balloon on the abdominal wall, due to the intra-colonic pressure, is in a range between 150 mmHg and 200 mm Hg. Optionally, the pressure exerted by the balloon on the abdomen when the intra-colonic pressure is greater than zero is substantially equal to, or less than, the intra-colonic pressure and is less than or equal to 200 mmHg, less than or equal to 150 mmHg, less than or equal to 100 mm Hg, less than or equal to 80 mmHg, less than or equal to 50 mm Hg, less than or equal to 40 mm Hg, less than or equal to 25 mmHg. The above pressure ranges for the balloon pressing the intestinal portion against the abdominal wall are for a relatively reduced period of time during which the intra-colonic pressure is greater than zero, and substantially prevents compression-related injuries to the intestinal portion while providing sealing.

In an exemplary embodiment, the stomal insert includes a cap which is attached to the cover for sealing a proximal opening to the elastic tube. Optionally, sealing the opening to the elastic tube allows for an intra-colonic pressure buildup in the stomal insert. Optionally, the elastic tube extends outwards from the stoma due to the intra-colonic pressure buildup inside the elastic tube when the proximal opening is sealed by the cap, possibly further pulling the balloon against the abdominal wall. Optionally, the elastic tube extends outwards from the stoma due to pressure exerted by waste content inside the elastic tube. Optionally, the cover separates from and ceases to press on the abdomen due to the elastic tube extending outwards from the stoma.

According to some embodiments of the present invention, the elastic tube is bendable for allowing relative motion between the cover on the external side of the abdomen and the balloon on the visceral side of the abdomen during variations in the abdominal geometry. Optionally, the mechanical movement of the stomal insert substantially minimally interferes with tissue movement. Optionally, tissue movement in the various layers of the abdominal wall due to the mechanical movement of the stomal insert may allow greater user comfort. Optionally, bending of the elastic tube may contribute to preventing inadvertent stomal insert extraction during increased intra-colonic pressure as the pressure acts off-axis relative to the elastic cover. Additionally, the elastic tube crimps when an external force is radially applied for reducing pressure on a stomal portion of the abdomen. Optionally, the external force is that applied by the abdominal wall on a stoma having an inserted tube ranging in diameter from 10 mm-30 mm. The crimping of the elastic tube increases the abdominal retention of the stomal insert as a greater tissue area in the stomal portion of the abdomen resists its withdrawal. Additionally, the elastic tube allows for peristaltic propelling of the waste contents.

According to some embodiments of the present invention, the inflatable balloon includes a toroidal shape. Alternatively, the balloon has a toroidal shape with a ring with a non-circular cross-section. Optionally, the cross-section of the ring is elliptical. Alternatively, the balloon is elliptically shaped. Optionally, the balloon is configured for use with varying abdominal wall thicknesses (each user has a different abdominal wall thickness) such that a partially inflated balloon is suitable for use with relatively thick abdominal walls while a fully inflated balloon is suitable for use with relatively thin abdominal walls. Optionally, the balloon is deformable and shifts in an axial direction away from the abdomen for reducing the pressure on the abdomen as the intra-colonic pressure increases and the balloon is pressed against the abdominal wall. Additionally, the balloon is inflated with an expansion fluid, which may be a compressible fluid such as air. Optionally, the expansion fluid is any other type of biocompatible fluid suitable for inflating the balloon. Alternatively, the balloon includes a biocompatible expansion fluid which heats up with body temperature and causes the balloon to expand.

According to some embodiments of the present invention, the stomal insert includes an inflation port for administering the expansion fluid to the balloon. Optionally, a needleless syringe type device containing the expansion fluid is connected to the inflation port. Additionally, the stomal insert includes an inflation lumen interconnecting the inflation port with the balloon through which the expansion fluid flows for inflating the balloon.

According to some embodiments of the present invention, the shape of the balloon forms a funnel-shape at the distal end of the stomal insert. Optionally, the funnel shape assists in guiding fecal matter into the elastic tube as it is propelled towards the stoma, opening the tube at the crimped section. Optionally, an internal surface of the elastic tube and the balloon opening are preferably as smooth as possible for providing substantially undisturbed flow of the waste content. Surface smoothness may be enhanced by methods known in the art, for example surface treatment to the tooling in which the components are fabricated, inserting additives to the raw material, or coating the material's surface with smoothening coating such as, for example, parylene.

According to some embodiments of the present invention, the elastic stomal cover is adapted to elastically press against the exterior of the abdomen and cover the stoma. Optionally, the elasticity is such that substantially any point on a circumference of the elastic cover may be displaced in the axial direction by up to 10 mm, 8 mm, 6 mm, 5 mm, or less. Responsively, the pressure variation exerted by the balloon is no more than the pressure that is normally exerted by the balloon when the intra-colonic pressure is zero, thereby maintaining the sealing. Optionally, the elastic cover is mushroom-shaped. Optionally, the elastic cover is adjustable in size for accommodating to variable abdominal wall thicknesses.

An aspect of some embodiments of the present invention relates to an integrally formed, single-component stomal insert. Optionally, the single-component stomal insert is readily and inexpensively produced, and is suitable for one-time use (remove and throw away). For example, the single-component stomal insert is removed and replaced once per day, twice per day, three times per day, once every two days, once every three days, or more. Optionally, the single-component stomal insert includes one or more of other components such as built-in collection bags, collection bag attachment mechanisms, removable cap attachment mechanisms, inflation ports, inflation lumens, and the like.

An aspect of some embodiments of the present invention relates to a method of pre-forming a balloon (formed in its inflated shape) for use with the stomal insert. An advantage of using a pre-formed balloon is that the balloon may be brought to its inflated shape by a relatively low inflation pressure, for example, between 10-100 mmHg. Optionally, the inflation pressure may range between 25-75 mmHg, 35-60 mmHg, 40-50 mmHg. Optionally, the low pressure keeps the balloon pliable and flexible. Optionally, the pliability and flexibility of the balloon allows for greater user comfort and substantially reducing tissue damage.

According to some embodiments of the present invention, the balloon may be produced with no parting line on its external surface. Optionally, the production includes using a regular mold with its cavity having a modified shape, such that upon demolding, the balloon is turned "inside-out" to obtain a desired geometry. The external surface of the demolded balloon becomes the internal surface after the balloon is turn inside-out so that the parting line is unexposed.

An aspect of some embodiments of the present invention relates to a method of producing the stomal insert wherein, the balloon and the elastic tube are separately fabricated and are attached together. Ins some embodiments, the balloon and the elastic tube are assembled into a seamless structure using welding, bonding, or other suitable technique known in the art for joining them together. Optionally, for joining the balloon and the elastic tube together, the elastic tube it is wrapped over a rigid mandrel and the balloon edges are elastically pressed against an elastic tube surface.

According to some embodiments of the present invention, the sections of the stomal insert include materials of durometer ranging from 1-50 Shore A. For example, the elastic tube may include material of durometer ranging from 1-50 Shore A, 5-50 Shore A, 10-40 Shore A, 20-30 Shore A. The inflatable balloon may include material of durometer ranging from 1-50 Shore A, 2-40 Shore A, 3-20 Shore A, 3-10 Shore A, 3-7 Shore A. The elastic cover may include material of durometer 1-50 Shore A, 5-50 Shore A, 10-40 Shore A, 20-40 Shore A. Optionally, the materials are non-abrasive and biocompatible, and may include, for example, silicone rubber, natural rubber, or other elastomeric and/or polymeric materials. Optionally, sections are of a thickness for substantially blocking odor transmissions. Optionally, the thickness is at least 0.50 mm. Optionally, the thickness is at least 0.60 mm, at least 0.70 mm, at least 0.80 mm, or more. Optionally, the sections may have a material thickness less than 0.50 mm, for example, less than 0.40 mm, less than 0.30 mm, less than 0.20 mm, or less. Optionally, the sections may include a dedicated coating adapted to reduce wall permeability for substantially blocking odor transmissions, for example parylene. Optionally, the single—component stomal insert includes sections with material thickness less than 0.50 mm. Optionally, the sections are seamless and have no parting lines, or include unexposed seams or parting lines, for preventing injury to bodily tissue due to abrasion with the seams and/or undesired concentrated mechanical stress along the seams/parting lines.

An aspect of some embodiments of the present invention relates to an active gas releasing mechanism for use with the stomal insert. Optionally, the active gas releasing system releases gas from inside the elastic tube while substantially preventing flow of waste content, including liquids, out of the elastic tube. Optionally, the passageway connects from an inside of the elastic tube to a valve which is opened by the user. Optionally, the passageway is part of a gas releasing mechanism attached to the cap so allowing the cap to be partially opened by the user for releasing the gas while the waste content remains contained inside the elastic tube. Optionally, operation of the active gas mechanism is automatic allowing gas to be released without user intervention in the operation. Alternatively, the stomal insert includes a passive gas filter mechanism or other gas filter mechanism known in the art.

An aspect of some embodiments of the present invention relates to a collection bag which attaches to the stomal cover for the collection of waste content. Optionally, the collection bag includes a gas filter mechanism. Optionally, the bag is accommodated, for example by furling or folding inside the proximal portion of the elastic tube and is deployed from inside the elastic tube by the user and/or by the pressure of the waste content. Alternatively, the bag is included in the cap and is accommodated in the proximal portion of the elastic tube when the cap is attached to the cover. Optionally, the collection bag is an ostomy pouch known in the art. Optionally, the collection bag is of an elastic material. Alternatively, the collection bag is of a similar material to that of the ostomy pouch. Alternatively, the collection bag is a domestic bag, for example, a sandwich bag or a food storage bag, and is attached to the stomal insert by an attachment mechanism on the proximal portion of the elastic tube which includes a snap-fit arrangement, or other suitable arrangement known in the art.

An aspect of some embodiments of the present invention relates to an Ostomy port kit for allowing a user to insert and remove the stomal insert at home. Optionally, a physician inserts and removes the stomal insert. Optionally, the Ostomy port kit includes the removable cap. Optionally, the kit includes an injector for administering the expansion fluid for inflating the balloon. Optionally, the kit includes one or more collection bags.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates a stomal insert 100 according to an embodiment of the present invention. Stomal insert 100 includes a stomal cover 102 for covering the stoma from an external side of an abdominal wall (from outside the body), a fixation element 104 inserted in an intestinal portion inside an abdominal cavity for fixating the stomal insert relative to the intestinal portion and for preventing its removal through the stoma, and an axially elastic tube 106 of diameter D interconnecting the cover and the fixation element. Optionally, the diameter D is in the range between 10-30 mm, for example, 15 mm, 20 mm, 25 mm. Optionally, stomal cover 102 is mushroom-shaped and may include an elastic material such as, for example, silicon, allowing the cover deformation flexibility. Optionally, fixation element 104 is a toroidal-shaped inflatable balloon. Optionally, stomal insert 100 includes an inflation port 108 through which an expansion fluid for inflating balloon 104 is administered, the expansion fluid flowing from the inflation port into the balloon through an inflation lumen 110. Deflating of balloon 104 is also done by drawing out the expansion fluid from the balloon through the inflation lumen 110 and out the inflation port 108. Optionally, inflation port 108 includes a Luer activated valve. Optionally, balloon 104 is self-inflatable and includes a biocompatible expansion fluid for inflating the balloon when inside the abdominal cavity. Optionally, balloon 104 is inflated by other methods known in the art not requiring use of inflation port 108 and/or inflation lumen 110.

Referring also to FIGS. 2A, 2B, and 2C, stomal insert 100 is an ostomy port and serves to conduct waste contents such as fecal matter from an intestinal portion 112 in an abdominal cavity 114 of a user out a stoma 116 in an abdominal wall 118. In some exemplary embodiments, stomal insert 100 is inserted through the stoma 116 into the intestinal portion 112, with an interior surface 122 of the intestinal portion sealingly fitted over balloon 104 and an external surface 124 of elastic tube 106, for substantially preventing leakage of waste contents and odor escape through stoma 116. The seal between interior surface 122 and external surface 124 is maintained regardless of variations in geometry of abdomen 118 and/or of intra-colonic pressure in intestinal portion 112. Optionally, the waste contents include urinary matter, intestinal portion 112 distally connected to a ureter in the user as a result of a urostomy.

In FIG. 2A, stomal insert 100 is shown inserted in stoma 116, intestinal portion 112 fitted over the stomal insert and attached to an abdominal wall exterior 126. Optionally, abdominal wall 118 is in a relaxed state and with an intra-colonic pressure of substantially 0 mmHg in intestinal portion 112. Optionally, in the relaxed state, a proximal opening 130 in stomal insert 100 is axially aligned with a distal opening 132. Balloon 104 is inflated viscerally to a muscular layer 120 of the abdominal wall 118 and exerts a pressure P on intestinal portion 112 pressing the intestinal portion against the muscular layer for providing the seal. Additionally, balloon 104 prevents inadvertent withdrawal of stomal insert 100 from stoma 116. Optionally, cover 102 covers stoma 116 and presses against a side of exterior abdominal wall 126 with a force F. Optionally, cover 102 prevents the stomal insert from being drawn into stoma 116. Elastic tube 106 applies a tensile force T on both cover 102 and balloon 104 pulling the cover against exterior abdominal wall 126 with the force F and the balloon against muscular layer 120 applying the pressure P. Optionally, an elastic tube section 128 inside stoma 116 is crimped by a radial pressure applied to the tube section by surrounding tissue in abdominal wall 118. An example of the crimping of elastic tube 106 is shown in FIGS. 3A and 3B which show a side view of stomal insert 100 and a cross-sectional view A-A of crimped elastic tube section 128, respectively, according to an embodiment of the present invention.

In FIG. 2B, stomal insert 100 is shown inserted in stoma 116 in an deformed state, the geometry of abdominal wall 118 optionally having undergone a variation due to a change in body posture or body movement. An abdominal fat layer 134 has moved relative to abdominal muscular layer 120, causing elastic cover 102 to move relative to balloon 104. Optionally, elastic tube 106 bends to accommodate the relative movement of fat layer 134, displacing proximal opening 130 relative to distal opening 132 so that they are no longer axially aligned. Optionally, elastic tube section 128 remains crimped under the pressure exerted by the surrounding tissue of abdominal wall 118.

In FIG. 2C, stomal insert 100 is shown inserted in stoma 116 pressing intestinal portion 112 against abdominal muscular layer 120 due to intra-colonic pressure, Pin, according to some embodiments of the present invention. Stomal insert includes a cap 114 attached to cover 102 for sealing the proximal end of elastic tube 106. Optionally cap 114 is removable or non-removable. Optionally, the pressure inside the elastic tube 107 is the intra-colonic pressure Pin. Optionally, as Pin increases and there is peristaltic contractions of intestinal portion 112, Pin increases above the atmospheric pressure Patm outside abdominal wall 118. Optionally, the larger Pin pushes stomal insert 100 in a proximal direction out of stoma 116, and is counteracted upon by abdominal muscular layer 120 pushing on the balloon. Optionally, intestinal portion 112 also counteracts stomal insert 100 being pushed in the proximal direction. A larger difference between Pin and Patm results in a better sealing as balloon 104 is pressed further into muscular layer 120.

In some exemplary embodiments, stomal insert 100 may be modeled by a spring system 200 having three springs 202, 204, and 206 as schematically shown in FIG. 4A. Optionally, cover 102 is elastic and may be represented by spring 202, inflatable balloon 104 by spring 204, elastic tube 106 by spring 206, exterior abdominal wall 126 by fixed support 208, and muscular layer by fixed support 210. Optionally, interplay exists between springs 202-206, each one deforming independently to allow spring system 200 to maintain a predetermined range of pressures applied on fixed supports 208 and 210. Optionally, using the model of spring system 200, an amount of deformation may be determined for elastic cover 102, inflatable balloon 104, and elastic tube 106, for allowing P to be maintained in the predetermined range between 1 mmHg and 50 mmHg in the relaxed state with intra-colonic pressure substantially zero, and less than 200 mmHg in an deformed state where there are variations in abdominal geometry and/or when the intra-colonic pressure is greater than zero.

FIG. 4B is a graphical representation illustrating design goal values for P optionally determined using the model of spring system 200, according to some embodiments of the present invention. Solid curve 402 represents the force F2 exerted on muscular layer 120 by balloon 104, round curve 404 represents a pressure component of P due to intra-colonic pressure, and square curve 406 the elastic component of P due to the tensile force T in elastic tube 106. Optionally, when the intra-colonic pressure is zero, sealing is substantially maintained due to the tensile force exerted by elastic tube 106 on balloon 104 and elastic cover 102. Optionally, in case of low non-zero intra-colonic pressure (on the order of few mmHg), two mechanisms are contributing to balloon 104 exerting pressure P against muscular layer 120, the tensile force from elastic tube 106 (elastic component) and the intra-colonic pressure in intestinal portion 112 (intra-colonic pressure component). As the intra-colonic pressure further increases, stomal insert 100 is pushed outwards. As a result, the intra-colonic pressure component of P increases, whereas F exerted on the exterior abdominal wall 126 by elastic cover 102 is relieved and the elastic component of P decreases.

In some embodiments, there is a level of intra-colonic pressure at which elastic cover 102 bulges out from exterior abdominal wall 126. The elastic component of P is zero, and sealing is maintained solely due to the intra-colonic pressure component of P. Any elevation in the intra-colonic pressure increases the pressure exerted by balloon 104 against muscular layer 120, and further secures the seal. Optionally, upon relief of the intra-colonic pressure the elastic nature of elastic cover 102, balloon 104, and elastic tube 106, return stomal insert 100 to its relaxed state.

In some embodiments, the elasticity of elastic cover 102, balloon 104, and elastic tube 106, maintains the seal between stomal insert 100 and intestinal portion 112 substantially throughout a whole range of intra-colonic pressures. Low intra-colonic pressure sealing is contributed to mainly by elasticity; the elastic component vanishing at higher pressure levels. Optionally, balloon 104 pressure on muscular layer 120 is maintained at a relatively low value, and a risk of compression-related tissue damage such as ischemia, necrosis, and the like is hence substantially reduced.

Reference is made to FIGS. 5A and 5B which schematically illustrate the interplay in the deformation of balloon 104 and elastic tube 106 in a first scenario wherein the elastic component of P due to the tensile force T predominates over the intra-colonic pressure component (intra-colonic pressure is zero or relatively small), and in a second scenario wherein the intra-colonic pressure component of P due to the intra-colonic pressure Pin predominates over the elastic component, respectively, according to some embodiments of the present invention. In FIG. 5A, stomal insert 100 is inserted through stoma 116 in abdominal wall 118. Optionally, elastic tube 106 applies the tensile force T to balloon 104 pulling the balloon and pressing it to abdominal wall 118. In FIG. 5B, the intra-colonic pressure pushes balloon 104 against abdominal wall 118. Optionally, balloon 104 partially deforms in an axial direction away from abdominal wall 118 for reducing the pressure P exerted on the abdominal wall. Optionally, elastic tube 106 is partially pushed out of stoma 116 in a proximal direction by the pressing of balloon 104 on abdominal wall 118 so that the tensile force T applied to the balloon is reduced to substantially zero. Optionally, only the intra-colonic pressure component of P acts on abdominal wall 118. Optionally, the elastic cover (not shown) bulges out from abdominal wall 118.

Reference is made to FIGS. 6A and 6B which schematically illustrate the interplay in the deformation of elastic cover 102 and elastic tube 106 in a first scenario wherein the user is in the relaxed state, and a second scenario wherein user movement results in a variation in the abdominal geometry, respectively, according to some embodiments of the present invention. In FIG. 6A, elastic tube 106 applies the tensile force T to elastic cover 102 for pressing the elastic cover against abdominal wall 118. Optionally, elastic cover 102 presses against abdominal wall 118 with force F=T. In FIG. 6B, the variation in the abdominal geometry results in elastic tube 106 being pulled in stoma 116 in a distal direction (into the abdominal cavity). Optionally, the tensile force T increases further pulling on elastic cover 102 which presses on abdominal wall 118 and partially deforms (for example, partially flattens) for reducing the pressure exerted on the abdominal wall.

Reference is made to FIGS. 7A and 7B which schematically illustrate the interplay in the deformation of elastic cover 102, balloon 104, and elastic tube 106, in a first scenario wherein the user is in the relaxed state, and a second scenario wherein user movement results in variations in the abdominal geometry, according to some embodiments of the present invention. In FIG. 7A, elastic tube 106 applies the tensile force T pressing elastic cover 102 and balloon 104 against abdominal wall 118. Optionally, elastic cover 102 and balloon 104 press against abdominal wall 118 with force F=T and P=T/A where A is a surface area of balloon 104 in contact with the abdominal wall, respectively. In FIG. 6B, the variations in the abdominal geometry optionally result in bending of elastic tube 106 so that the axial tensile force T acts on elastic cover 102 by deforming some portions of the cover more than others. Additionally, tensile force T acts on balloon 104 by optionally deforming along the axial direction some portions of the balloon more than others for maintaining the balloon pressing against abdominal wall 118 at the predetermined range of pressures.

FIG. 8 schematically illustrates a stomal insert 300 including elastic cover 102, elastic tube 106, inflation port 108 and inflation lumen 110, according to some embodiments of the present invention. Optionally, stomal insert 300 additionally includes balloon 304 functionally similar to balloon 104 in FIG. 1 but having a toroidal shape with a ring including a non-circular cross-section. Optionally, balloon 304 is assembled in stomal insert 300 such that the stomal insert or its components have no exposed seams or parting lines which may contribute to tissue damage.

FIG. 9 schematically illustrates a stomal insert 400 including elastic cover 102, elastic tube 106, inflation port 108 and inflation lumen 110, according to some embodiments of the present invention. Optionally, stomal insert 400 additionally includes balloon 404 functionally similar to balloon 104 in FIG. 1 but having a toroidal shape with a ring including a non-circular cross-section. Optionally, balloon 404 is assembled in stomal insert 400 such that the stomal insert or its components have no exposed seams or parting lines which may contribute to tissue damage.

FIGS. 10A and 10B illustrate a stomal insert 500 adapted to be inserted in stomas formed in abdominal walls varying in thickness from one user to another, according to some embodiments of the present invention. Optionally, stomal insert 500 includes elastic cover 102, elastic tube 106, and an inflatable balloon 504 functionally similar to balloon 104 and which may be partially inflated or fully inflated to adjust for varying degrees of abdominal wall thickness.

In FIG. 10A, stomal insert 500 is shown inserted through a stoma 516A formed in an abdominal wall 518A having a relatively thick fatty layer 534A and a relatively thick muscular layer 520A. Optionally, balloon 504 is partially inflated with an expansion fluid (not shown) and presses against the muscular layer 520A, elastic tube section 128 crimped substantially along a mid portion of elastic tube 106. Optionally, balloon 504 may press against muscular layer 520A using the intra-colonic pressure component of P, the elastic component, or a combination of both.

In FIG. 10B, stomal insert 500 is shown inserted through a stoma 516B formed in an abdominal wall 518B having a relatively thin fatty layer 534A and a relatively thin muscular layer 520A. Optionally, balloon 504 is fully inflated with the expansion fluid and presses against the muscular layer 520B, elastic tube section 128 crimped substantially along a substantially forward portion of elastic tube 106. Optionally, balloon 504 may press against muscular layer 520B using the pressure component of the force F2, the elastic component, or a combination of both.

FIGS. 11A-11C schematically illustrate different embodiments of stomal inserts 600A-600C similar to stomal insert 100 but having different elastic stomal covers 602A-602C, respectively, according to some embodiments of the present invention. Optionally, elastic covers 602A-602C are functionally similar to elastic cover 102 but are differently shaped. Optionally, in FIG. 11A, elastic cover 602A is circularly shaped having a circumferential rounded rim 605 for pressing against the abdominal wall and a deformable surface 607A connected to elastic tube 106. Optionally, in FIG. 11B, elastic cover 602B includes a circumferential edge 605B for pressing against the abdominal wall and a deformable surface 607B connecting to the elastic tube 106 and through a curved section 609B to the circumferential edge for providing a degree of resiliency in the elastic cover. Optionally, in FIG. 11C, elastic cover 602C is a flexible plate connecting to elastic tube 106, and includes springs 603C for pressing against the abdominal wall. Alternatively, plate 602C may be rigid or semi-rigid.

FIG. 12A schematically illustrates a stomal insert 700 including an elastic stomal cover 702, an inflatable balloon 704, and an elastic tube 706 all integrally formed as a single component suitable for one-time use, according to some embodiments of the present invention. Optionally, stomal insert 700 includes an inflation port 708 and an inflation lumen 710, Stomal insert 700, including elastic cover 702, balloon 704, elastic tube 706, inflation port 708, and inflation lumen 710, may be similar to that shown in FIG. 1 at 100 including 102, 104, 106, 108, and 110, optionally, with the difference that in some embodiments balloon 704 is formed with a loose end 705 attachable to the a distal exterior surface 707 of the elastic tube during assembly of the stomal insert. Optionally, a proximal end of elastic tube 706 is fitted with a non-removable cap 714 (or seal) so that stomal insert 700 is removed and disposed of when filled with waste content. In some embodiments, seal 714 is embodied as an expanding waste bag, for example, as described with respect to FIGS. 16A and 16B.

In an exemplary embodiment of the invention, an optional self contained pump 711 is provided. Such a pump 711 may also be provided with other port designs, for example, those that include a balloon or other inflatable elements.

In one example, pump 711 is an air pump. Optionally, pump 711 is located in line with inflation channel 710, optionally within it. In an alternative embodiment, pump 711 is mounted on or integral with stomal cover 702.

In an exemplary embodiment of the invention, the pump is an air pump which uses a foam or other expanding element 715 to expand and includes at least one one-way valve 716. In operation, when the pump is compressed, air in the foam is pushed through valve 716 (e.g., a one way flap valve) into lumen 710. Optionally, a second one way valve 718, for example, a flap valve, is provided to prevent air escape during such compression. When the pump is released, the foam or other expanding element elastically expands, drawing air in from the outside. Balloon deflation is optionally provided by pressing on the valves so they are not patent. In an exemplary embodiment of the invention, the flaps are integrally formed with the body of the port. Alternatively the pump is attached, optionally using adhesive.

Such valves may be provided also without the pump mechanism, for example, in other embodiments of the invention.

In an alternative embodiment, a liquid pump is provided. Optionally, a compressible reservoir 713 is provided filled with liquid or other fluid and which is fluidically connected to lumen 710, via a one way valve (e.g., 716). When reservoir 713 is compressed, fluid passes through the valve into lumen 710. Optionally, manipulating the valve allows the retention balloon to deflate.

Optionally, the reservoir is large enough to fill the entire balloon. In an alternative embodiment, the reservoir is only large enough for manipulating the balloon pressure, for example, having a volume of, for example, between 10% and 50% thereof. Optionally, lumen 710 can be used for filling the balloon and/or reservoir as described herein.

FIGS. 12B and 12C show alternative embodiments for a port including an integral pump 711, in accordance with exemplary embodiments of the invention.

In FIG. 12B, an extension 717 to lumen 710 is provided along and/or integrated with stomal cover 702, with pump 711 (e.g., using a foam element in a pump cavity and two one way valves), integral therewith in the cover. In use, the pump may be pinched between two fingers.

FIG. 12B also shows an optional deflation valve 719, which could also be located at other places along lumens 710 and/or 717 and/or attached using a separate or partially separate deflation lumen.

In FIG. 12C, extension lumen 717 may be a separate tube and pump 711 is provided at an end of the tube, with pump 711 optionally hanging separately from stomal cover 702. Optionally, the pump can be attached to cover 702, for example, using Velcro (e.g., a hook and loop connector) or a tack substance and/or placed between cover 702 and the body.

FIG. 13 schematically illustrates a stomal insert 800 with a removable cap 814 for removing waste content, according to some embodiments of the present invention. Stomal insert 800 includes an elastic tube 806 with a cap attachment mechanism 807 for securing cap 814 to the stomal insert. Stomal insert 800 is similar to stomal insert 100 shown in FIG. 1 except for removable cap 814 and cap attachment mechanism 807, which may be as known in the art. Removable cap 814, in some embodiments, has a tab 816 for easy removal of the cap. Optionally, attachment mechanism 807 is adapted to be fitted with a collection bag (not shown) into which waste content flows out of stomal insert 800 following removal of cap 814. Optionally, the collection bag is attached to attachment mechanism 807 following removal of cap 814. Optionally, stomal insert 800 is formed as a single component similar to stomal insert 700 shown in FIG. 12, excluding removable cap 814 which is separately produced from the stomal insert.

FIG. 14 schematically illustrates a stomal insert 900 with a built-in collection bag 912 for collecting waste content, according to some embodiments of the present invention. Stomal insert 900 includes an elastic tube 906 to which collection bag 912 is attached at a proximal end. Optionally, collection bag 912 is accommodated inside elastic tube 906. Optionally, collection bag 912 may have any shape suitable for collecting waste content while stomal insert 900 is in use by a user. Alternatively, collection bag 912 is attached to an attachment mechanism (not shown) on elastic tube 906. Stomal insert 900 including elastic tube 906 is similar to stomal insert 100 including elastic tube 101 shown in FIG. 1 except for the collection bag arrangement. Optionally, stomal insert 900 is formed as a single component similar to stomal insert 700 shown in FIG. 12 with the difference of collection bag 912.

FIGS. 15A-15C schematically illustrate a stomal insert 1000 including an attachment mechanism 1007 at a proximal end of elastic tube 1006, for attaching a collection bag 1012, according to some embodiments of the present invention. Optionally, collection bag 1012 includes an opening 1015 with an annular elastic rim 1013 adapted to be inserted in a circumferential recess 1014 in attachment mechanism 1007. Optionally, attachment mechanism 1007 includes a locking mechanism 1011 for locking annular elastic rim 1013 inside circumferential recess 1014, and is adapted to support a weight of collection bag 1012 including waste content. Optionally, annular elastic rim 1013 includes a latex material or other type of elastomeric material. Alternatively, annular elastic rim is non-elastic and is preformed of a circumference suitable for fitting in circumferential recess 1014 and locked in place by locking mechanism 1011. Optionally, collection bag 1012 includes an elastic material. Stomal insert 1000 including elastic tube 1006 is similar to stomal insert 100 including elastic tube 101 shown in FIG. 1 except for attachment mechanism 1007.

FIGS. 16A-16C schematically illustrate a stomal insert 1100 including an attachment mechanism 1107 at a proximal end of elastic tube 1106, for attaching a cap 1114 including a collection bag 1112 accommodated inside a shell 1111, according to some embodiments of the present invention. Cap 1114 is adapted to be attached to the proximal end of elastic tube 1106 such that collection bag 1112 is inside the elastic tube. Optionally, cap 1114 attaches to an attachment mechanism 1107 at a proximal end of elastic tube 1106, and optionally provides an air-tight seal of the elastic tube. Optionally, the air-tight seal allows for an increase in the intra-colonic pressure in elastic tube 1106. Optionally, attachment mechanism 1107 includes a "bayonet" locking arrangement for sealingly accommodating mating tabs 1116 on cap 1114. Alternatively, attachment mechanism 1107 and cap 1114 include other types of lock mating arrangements known in the art. Stomal insert 1100 including elastic tube 1106 is similar to stomal insert 100 including elastic tube 101 shown in FIG. 1 except for attachment mechanism 1107.

Cap 1114 includes a proximal opening 1119 onto which is fitted a removable cover 1115, the cover adapted to be removed by a user for allowing collection bag 1112 to be deployed through the opening for collecting waste content. Optionally, collection bag 1112 is deployed by the user and the waste content flows into the collection bag pushed by the intra-colonic pressure. Alternatively, collection bag 1112 is pushed out by pressure exerted by the waste content and/or the intra-colonic pressure. Optionally, removable cover 1115 is removed from cap 1114 by a pushing force exerted by collection bag 1112 due to pressure from the waste content and/or the intra-colonic pressure. Optionally, cap 1114 and/or removable cover 1115 is of a stretchable material which allows it to deform and protrude outwards due to pressure exerted by waste content and/or flatus inside elastic tube 1107. Optionally, the deformation of cap 1114 and/or cover 1115 serves to indicate to the user of a need to release gas or remove waste content.

FIGS. 17A-17D schematically illustrate a stomal insert 1200 including an attachment mechanism 1207 at a proximal end of elastic tube 1206, for attaching a collection bag 1212 used in domestic applications (for example, a sandwich bag, small garbage bags, and the like), according to some embodiments of the present invention. Optionally, attachment mechanism 1207 includes a snap-fitting arrangement for attaching a removable annular fastener 1213 having an opening 1211 through which a portion of collection bag is inserted. Optionally, annular fastener 1213 includes a latching element 1217 which snap-fits onto attachment mechanism 1207 and secures a rim portion 1219 of collection bag 1212 between the latching element and the attachment mechanism. Optionally, other fastening arrangements known in the art may be used for removable annular fastener 1213 and attachment mechanism 1207 for securing collection bag 1212 to stomal insert 1200. These may include twist-locking and securing rim portion 1219 by pressing on the rim portion in an axial direction parallel to that of elastic tube 1206, or using a spring mechanism in attachment mechanism 1207 so that the spring secures the rim portion while pressing against annular fastener 1213. Stomal insert 1200 including elastic tube 1206 is similar to stomal insert 100 including elastic tube 101 shown in FIG. 1 except for attachment mechanism 1207 and removable annular fastener 1213.

FIG. 18 schematically illustrates a stomal insert 1300 including an elastic stomal cover 1302 adjustable for use with users of variable abdominal wall thickness, according to some embodiments of the present invention. Optionally, stomal cover 1302 includes cutting marks 1303 circumferentially arranged on the stomal cover and adapted to be cut in a circumferential direction prior to introducing stomal insert 1300 into a stoma, for increasing a distance L between a distal edge 1305 of the stomal cover of and a proximal end 1307 of a balloon 1304. Optionally, L is in a range between 1 cm-15 cm, for example, 3 cm, 6 cm, 9 cm, 12 cm. Optionally, a length of elastic tube 1306 remains the same. Optionally, increasing distance L allows stomal insert 1300 to be accommodated in a thicker abdominal wall. Stomal insert 1300 including elastic cover 1302, balloon 1304, and elastic tube 1306, may be similar to that shown in FIG. 1 at 100, including 102, 104, and 106.

FIGS. 19 and 20A-20C schematically illustrate a stomal insert 1400 including an elastic stomal cover 1402 adjustable for use with users of variable abdominal wall thickness, according to some embodiments of the present invention. Optionally, elastic cover 1402 includes cutting marks 1403 circumferentially arranged along the stomal cover and adapted to be cut by radial cuts 1409 extending from a distal end 1405 of the stomal cover prior to introducing stomal insert 1400 in a stoma. Optionally, radial cuts 1409 separate elastic cover 1402 into sections 1411 capable of flexing in a proximal direction for increasing a distance M between distal edge 1405 and a proximal end 1407 of a balloon 1404. Optionally, a length of elastic stomal tube 1406 remains the same. Optionally, increasing distance M allows stomal insert 1400 to be accommodated in a thicker abdominal wall. Stomal insert 1400 including elastic cover 1402, balloon 1404, and elastic tube 1406, may be similar to that shown in FIG. 1 at 100, including 102, 104, and 106.

FIG. 21 schematically illustrates an Ostomy Port Kit 2100 for self-insertion in a stoma by a user having undergone an Ostomy, optionally for insertion by medical personnel or a user assistant. Ostomy Port Kit 2100 includes a stomal insert 2102 and an optional cap 2104, which may include any of the stomal inserts and removable/non-removable caps previously described herein. Optionally, Ostomy Port Kit 2100 includes an expansion fluid injector 2106 for attaching to an inflation port on stomal insert 2102. Optionally, Ostomy Port Kit 2100 includes at least one waste collection bag 2108, which may include any of the waste collection bags previously described herein, including its attachment accessories as applicable for attaching to stomal insert 2102.

FIG. 22 is a flow chart showing operation of stomal insert 100, according to some exemplary embodiments of the present invention.

At 2200, stomal insert 100 is adjusted to a size required by a user. Optionally, a length of elastic tube 106 is cut to a user's length at a manufacturing facility of stomal insert 100 and the stomal insert is manufactured by attaching cover 102 and balloon 104 to the cut elastic tube. Alternatively, cover 102 and balloon 104 are integrally formed with elastic tube 106 such that the length of elastic tube 106 is preadjusted to that required by the user. Additionally or alternatively, the user fits stomal insert 100 to the required size by trimming stomal cover 102

At 2202, the user inserts stomal insert 100 into stoma 116 in a distal direction from the external abdominal wall 126 into the abdominal cavity until cover 102 is pressed against the external abdominal wall. Optionally, a physician or other appropriate medical personnel performs the insertion.

At 2204, the user inflates the balloon by introducing an expansion fluid into inflation port 108. Optionally, inflation port 108 includes a Luer connector to which the user attached a needleless syringe with the expansion fluid. Optionally, balloon 104 is self-expanding and includes an expansion fluid. Optionally, the expansion fluid is heat activated by the internal body heat and expands accordingly. Optionally, the expansion fluid expands after a predetermined period of time. Optionally, the balloon expands to a predetermined size, which may be fully expanded, or partially expanded.

At 2206, the user optionally attaches a cap 114 to cover 102. Optionally, cap 114 includes a collection bag which is accommodated in a proximal section of elastic tube 106.

At 2208, the user is in the relaxed state, and proximal opening 130 and distal opening 132 in stomal insert 100 are substantially aligned. Optionally, elastic tube 106 includes a crimped portion 128 where surrounding tissue in the abdominal wall 118 exerts a radial force on the elastic tube. Optionally, elastic tube 106 applies the tensile force T to balloon 104 so that the balloon presses on muscular layer 120 with a pressure P ranging from 1 mmHg to 50 mmHg. Optionally, only the elastic component of P exerts the pressure of balloon 104 (the intra-colonic pressure component is substantially zero).

At 2210, the user is in the deformed state stomal insert 100 and abdominal fat layer 134 has moved relative to abdominal muscular layer 120, causing elastic cover 102 to move relative to balloon 104. Optionally, elastic tube 106 bends to accommodate the relative movement of fat layer 134, displacing proximal opening 130 relative to distal opening 132 so that they are no longer axially aligned. Optionally, elastic tube section 128 remains crimped under the pressure exerted by the surrounding tissue of abdominal wall 118. Optionally, elastic tube 106 applies the tensile force T to balloon 104 so that the balloon presses on muscular layer 120 with a pressure P ranging from 1 mmHg to 50 mmHg. Optionally, only the elastic component of P exerts the pressure of balloon 104 (the intra-colonic pressure component is substantially zero).

At 2212, the user experience intra-colonic pressure buildup, the pressure in intestinal portion 112 and elastic tube 106 optionally, building up to 150 mmHg. Optionally, balloon 104 presses intestinal section 112 against muscular layer 120 with a pressure P less than or equal to 150 mmHg maintaining the sealing. Optionally, the elastic component and the intra-colonic pressure components of P combine to exert the pressure of balloon 104. Optionally, the elastic component decreases to substantially zero and only the intra-colonic component influences the pressure exerted by balloon 104.

At 2214, the user optionally releases an active gas filtering mechanism for releasing flatus in elastic tube 106. Optionally, cap 114 protrudes outwardly as an indication of the gas in elastic tube 106. Optionally, the active gas mechanism is automatically activated by the increased intra-colonic pressure. Optionally, a passive gas filtering mechanism filters the flatus. At 2216, the user opens cap 114 and pulls out a collection bag from inside elastic tube 106. Optionally, the collection bag is pushed out of elastic tube 106 by the waste content in the elastic tube. Optionally, the collection bag is included in cap 114. Optionally, the collection bag is pulled out through an opening in cap 114 following removal of a cap cover so that the cap does not require prior removal. Optionally, the bag is a domestic collection bag.

At 2218, the user removes the collection bag with the waste content and replaces the bag accommodating it inside elastic tube 106. Optionally, the cap and the collection bag are both removed. Optionally, the user performs irrigation before replacing the bag. Return to 2206.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find calculated support in the following examples.

EXAMPLES

Reference is now made to the following examples, which together with the above descriptions illustrate some embodiments of the invention in a non limiting fashion.

Following is a report documenting a study to evaluate the safety and efficacy of an artificial colostomy sphincter in a pig model as part of a Preclinical study.

Introduction

A new device for the management of colostomy, the AOS-C1000™, has been introduced. In a series of ex-vivo tests, the AOS-C1000™ was activated in a fresh porcine colon and was shown to hermetically seal the colon against liquid water.

The ex-vivo model is inherently limited by the fact that it does not permit evaluation of the device's ability to seal the intestine in the dynamical and responsive environment that exists in the living body, neither does it sheds light on the ability of the device to be retained in the body. Furthermore, the ex-vivo model does not provide information about the safety of the device in the living body. In order to better evaluate the safety and efficacy of the AOS-C1000™, an in-vivo model was needed.

In a preliminary in-vivo study aimed at exploring the proper method to stabilize a colostomy in a pig model, it has been found that an end colostomy formed at the cecum with the remainder of the large intestine bypassed might be causing loss of body weight, presumably due to lack of nutrition absorption. On the other hand, formation of a rectal end colostomy might be causing stomal retraction and skin stricture. The most stable model which was demonstrated and therefore chosen for this study was a cecal ostomy with the large intestine maintained functional.

In the current study, the AOS-C1000™ device was used in four pigs with cecal colostomies in order to evaluate its safety and effectiveness. The device was inserted daily for 10 hours a day during a period that varied among the animals (one month in two animals, two months in one animal, and three months in the remaining animal).

Study Objectives

The purpose of this study was to evaluate the safety and efficacy of the AOS-C1000™ device under in-vivo conditions in a pig model. In particular, the following safety and effectiveness issues were covered by the study:

Safety Objectives

The effect of the device on the animal's general health (demonstrated by increasing body weight and lack of clinical complication during the study).

The effect of the device on the intestinal tissue and peristomal skin (demonstrated by visual and manual inspections and by histological evaluation).

The ability of the device to transfer fecal matter (demonstrated by visual inspection of fecal matter flow into the device).

The ability of the device to transfer fecal matter without causing or contributing to an intestinal blockage (demonstrated by clinical follow up and fecal matter volume measurement).

The effect of insertion and removal of the device on the device's performance and on the intestinal tissue (demonstrated by inspection of device performance and by histological evaluation).

Effectiveness Objectives

The functionality of the device's retention mechanism, in terms of the ability of the device to be maintained in place and the force required to pull it out (demonstrated by dedicated retention tests and by tracing unintended device ejections).

The ability of the device to hermetically seal the intestine (demonstrated by dedicated sealing tests and by visual inspection of fecal leakage).

Materials and Study Methods

Study Device

The AOS-C1000™ is a medical device that provides controllable bowel management and evacuation for people with colostomies. The device significantly improves the users' quality of life, and reduces related adverse events. It consists of two components: the Ostomy Port and the CapsuleCap™.

The Ostomy Port (FIG. 23) is a flexible silicone-based mushroom-shaped device, composed of a collapsible tube and an external cover. During installation, the tube is inserted through the stoma into the intestine, while the external cover extends from the abdominal skin outwards and covers the stoma. A retention balloon, located at the distal end of the tube, functions as a retention mechanism for device retention and sealing. The Ostomy Port also enables introduction of irrigation fluid or other substances into the intestine.

In order to provide the user with continence, the CapsuleCap™ (FIG. 24) is used to hermetically seal the proximal opening of the Ostomy Port. The CapsuleCap™ is a semi-rigid capsule-like housing, containing a densely furled disposable bag (FIG. 24, right) that is held by an aesthetic cover (FIG. 24, left). Upon need the user may remove the aesthetic cover and deploy the bag, allowing waste matter to be expelled from the body through the flexible tube and collected in the bag. When done, the CapsuleCap™ is easily disconnected from the Ostomy Port and replaced with a new one.

In the current study the functionality of the CapsuleCap™ was not evaluated. Instead, the Ostomy Port was sealed by means of a flexible silicone disc (Ecoflex 0030, Smooth-On Inc., PA, USA) 1-2 mm thick, that was bonded to the device's proximal opening using an RTV adhesive (Boss 315, Accumetric LLC, KY, USA).

Study Animals

Four female domestic pigs were used (see Table 1). Each animal has undergone an acclimation period of at least four days long. The animals were kept in the large animals study facility of Vetgenerics Research Ltd. (PreClinical Group) at Moshav Ben Shemen, Israel. Due to the closure of the study facility during study run, the animals were moved on Oct. 7, 2010 to the large animals study facility of Biotech Farm at Kibbutz Naan, Israel. The same staff familiar with the study design was kept. Feeding included commercial premix (#125, Dagan premix plant) at 1% of body weight and free watering, excluding the day of surgery during which the animals were fasted (yet receiving free watering). Body weight was recorded twice a week during the whole study.

TABLE 1

Summary data regarding the study animals.

| Animal no. | Source | Clinical condition on arrival | Overall study duration* | Initial body weight (kg) | Terminal body weight (kg) |
|---|---|---|---|---|---|
| 9 | Yaar Shivuk (Iblin, Israel) | Very good | 140 days | 42.4† | 79.6 |
| 10 | Yaar Shivuk (Iblin, Israel) | Very good | 113 days | 38.0 | 68.4 |
| 12 | Yaar Shivuk (Iblin, Israel) | Very good | 59 days | 31.0 | 45.8 |
| 13 | Yaar Shivuk (Iblin, Israel) | Very good | 59 days | 30.0 | 45.1 |

*From day of arrival to day of euthanasia
†Recorded four days post arrival

Creation of the Ostomy

Prior to the surgery the skin of each animal was shaved around the abdominal midline and around the planned location of the stoma. The animal was anesthetized (Ketamine 20 mg/kg+Xylazine 2 mg/kg I.M., then Valium 1 mg/kg I.M. Additional dose of 1-2 ml Ketamine+Valium 1:1 v/v was administrated I.M. upon need) and then connected to a ventilation unit, through which anesthetics (Isoflurane 1-5%) was constantly administrated. In order to avoid hypothermia, warmed containers of saline were attached to the animal's body, and warm saline was administrated on exposed inner organs upon need. Body temperature was monitored intermittently.

Figure 25A:
Figure 25B:
Figure 25C:
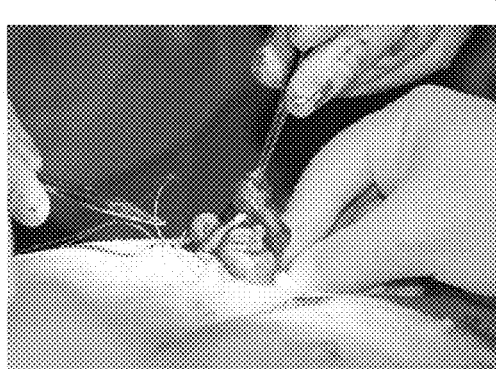
Figure 25D:
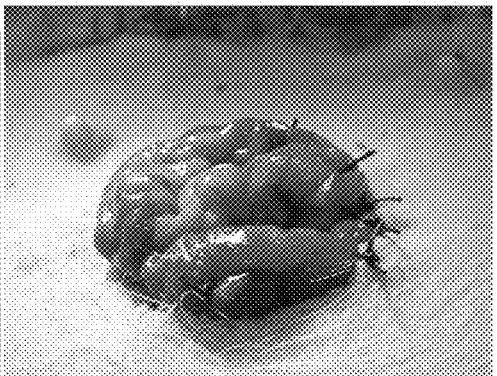

The operation was performed in the same manner and by using the same surgical tools and surgical practice as in human surgery. Operation was performed via midline incision. First the cecum was mobilized with preservation of the mesentery and its blood supply. A Ø22 mm circular piercing was made in the abdominal wall, using a dedicated device (similar to a standard biopsy punch) (FIG. 25a). The piercing was located a few centimeters aside the midline, such that the cecum was capable of being brought through the piercing to the skin without excessive tension. The subcutaneous layer was exposed at a circumferential strip around the abdominal piercing to ensure good attachment between the intestine and the skin (FIG. 25b). An end colostomy was then created using the cecum (FIGS. 25c-25d), while the large intestine was maintained intact. The abdominal incision was closed using subcutaneous stitching and surgical staples, and the stoma was covered with a standard bandage.

During the surgery the thickness of the abdominal wall at the stoma site was measured, and the length of the device was set accordingly to fit the particular animal's anatomy.

Study Routine

The days subsequent to the surgery were dedicated to healing and recovery, with antibiotics (Metronidazole 100 ml I.V.) and analgesics (Tramadol 2 ml I.V. or Optalgin 5-10 ml/100 kg I.V.) being administrated upon need. After the animals have recovered and regained weight, and no less than 14 days post surgery, routine insertion of the device was initiated.

The device was inserted daily (excluding weekends and holydays), and the retention balloon was inflated with 40 ml air. After 10 hours the balloon was deflated, the device was taken out, and the amount of fecal matter discharged from the stoma was recorded. In case of device unintended ejection during the 10 hours insertion period the device was re-inserted, however no more than two insertions were allowed in a single day. The device was also not re-inserted in situations where the ejected device was damaged by the animal and a functional device was not available. During the first week of the routine the proximal opening of the device was left open, in order to reduce pressure build-up behind the device and hence to have the intestine only partially loaded. In the remaining period a sealed device was used. The total duration of the device insertion routine varied among the study animals, as summarized in Table 2. Distribution between days in which the device was inserted for 10 hours, days in which the device was inserted for less than 10 hour, and days in which the device was not inserted at all, is depicted in FIG. 26.

Retaining and Sealing Tests

Functional tests intended for evaluating the device's ability to be retained inside the body and to hermetically seal the intestine were performed both at the beginning and at the end of the device insertion routine. The animals were anesthetized during the former instance of functional tests and awake during the latter.

The retaining test consisted of inserting the device into the stoma, inflating it with 40 ml air, and pulling it outwards (FIG. 27). The pulling force applied to the device was measured by means of an electronic force gauge (WeiHeng, China; weighing capacity 20 kg, accuracy 10 g). Pulling was stopped when approx. 1.5 kg tension was reached.

In the sealing test a dedicated device was used, that was basically the same as the regular device with its tube being longer than that of the regular device and with the addition of an inlet valve at the front end for insertion of fluid into the intestine. The device was inserted and inflated, and 500 ml tap water or saline were administered through the inlet valve into the intestine (FIG. 28a). Because of the redundancy in the length of the dedicated device's tube, the retention balloon was relaxed rather than tightened against the abdominal wall. With the device and intestine full of liquid, visual inspection was made seeking for leakage (FIG. 28b). Inspection was done in three conditions: relaxed, with a tension force of about 200 gr. applied to the device in order to tighten the retention balloon against the abdominal wall, and with the peristomal skin vigorously massaged.

In the first three sacrificed animals (no. 10, 12 and 13) the terminal retaining and sealing tests were performed a few minutes prior to the animal's sacrifice. In the remaining animal (no. 9), the retaining and sealing tests were performed four and eight days before the animal sacrifice, respectively.

Animals Sacrifice

At the end of the device insertion routine per study design the animals were sacrificed and the physiological condition of the stoma and the intestine were visually evaluated. Skin and intestine samples were then taken out for pathological evaluation. Samples were taken both from regions in contact with the device and from distant regions, the later serving as control samples.

Results

After recovering from the surgery, all animals were exhibiting active and vital behavior, and were constantly gaining weight (FIG. 29). The physiological condition of the stoma and the intestine was very good along the whole study, as evaluated both by finger examinations and visual inspections. One animal (#12) had a moderate stomal edema after the surgery, prior to first device insertion. The stomal swallowing has led to local invasion of a non-absorbable suture into the stomal tissue. This finding has well healed in a few days and had no apparent effect on the device functioning or on the condition of the stoma. Another animal (#9) has jumped out of its stall and a mild stomal bleeding was observed. Three days later a mild degree of stomal retraction was also observed. The retraction had no apparent effect on device functioning.

The peristomal skin intermittently exhibited a mild degree of redness and irritation in all animals, due to presence of irritative cecal excrement expelled from the stoma in periods where the device was not present. These findings were treated by local administration of antibiotic paste (Bactroban). No ischemia, ulceration, decubitus or other pressure-related adverse events could be detected in the skin or in the stoma.

Upon animals sacrifice, the intestine and peristomal skin were dissected and visually evaluated. All tissues exhibited normal and vital appearance. The mucosal layer of the intestine appeared intact and well perfused in all animals, with no signs of ischemia, necrosis or ulceration (FIG. 30).

Pathological evaluation of intestine and skin samples has found that the tissues were within normal limits with mild findings that were very similar in the functional samples (i.e. tissue samples that were in contact with the device) and the control samples. The main findings in the intestine samples were mild epithelial attenuation and minimal proprial edema and submucosal edema. No evidence of erosion, necrosis, ulceration or inflammation of the mucosa was observed (FIG. 31). Skin samples were essentially normal, with small amounts of debris and bacterial infiltration that were interpreted as related to feed or fecal material that were probably present in the area. No evidence of necrosis, ulceration, hyperplasia or fibrosis was found.

The device's flexibility enabled tight folding on itself such that the tube's cross sectional area was very low. As a result device routine insertion was very easy to execute. Device removal was easy to execute as well, requiring merely a mild pulling. No degradation in functionality could be observed in any of the devices used in the study along their life cycle. Average incidence of device unintended ejection was 0.13 ejections/animal/day. Distribution of unintended ejections over the device usage duration is depicted in FIG. 32.

The animals' large intestine was kept functional, and fecal matter was expelled both from the anus and from the stoma. In most of the study duration, where a sealed device was used, fecal matter was forced to be retained in the cecum while the device was present in the stoma. In case of intra-abdominal pressure elevation, fecal matter was clearly seen to fill the device's tube and to push the silicone sealing of the device outwards (FIG. 33). The volume of accumulated waste matter that was discharged from the stoma upon removal of the device is shown in FIG. 34.

Device's retaining tests were performed twice for each animal, one at the beginning of the device insertion routine and the other before the animal was sacrificed. The device was pulled using a gradually increasing force, up to a level of approx. 1.5 kg. In all tests the device was retained in the animal's body without being withdrawn. In one instance device retaining required inflating the device's retaining balloon with 45 ml air, whereas in the remaining tests inflation with 40 ml air was sufficient. The maximal pulling force applied to the device during the retention tests is summarized in Table 3.

A Sealing tests was performed next to each retaining test. With relaxed device and upon vigorously massaging the peristomal skin, very good sealing was observed in all but two of the tests, slight water dripping being observed in the later. Gentle pulling of the device (200 gr. tension) has resulted in perfect sealing in all of the tests. The sealing tests results are also summarized in Table 4.

Discussion and Conclusions

The AOS-C1000™ device was used in four pigs with a cecal ostomy along duration of one to three months. Study objectives were to evaluate safety and effectiveness of the device in an in-vivo porcine model. After recovering from the initial surgery all of the animals exhibited normal vitality and activity along the whole study duration. The physiological condition of the stoma, intestine and peristomal skin was constantly monitored, and was eventually evaluated by means of macro-pathological and pathological evaluations. All of the evaluated tissues were within normal limits, with mild findings that were very similar both in tissues in contact with the device and in control tissues. No other localized or systemic significant pathologies were observed.

Figure 35A:
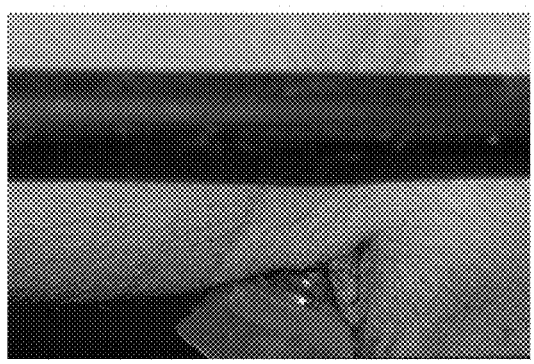
Figure 35B:
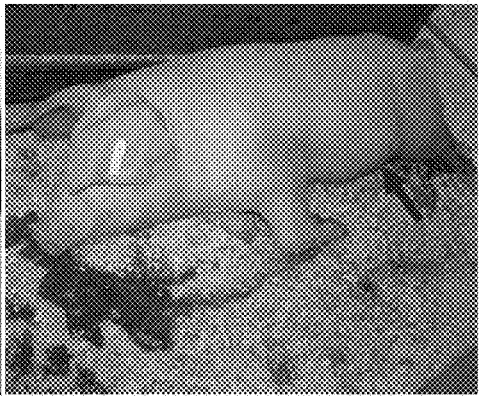
Figure 35C:
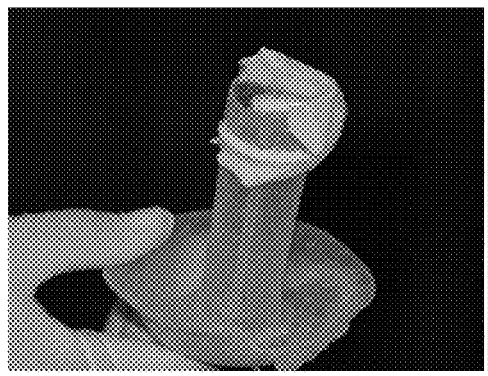
Figure 35D:
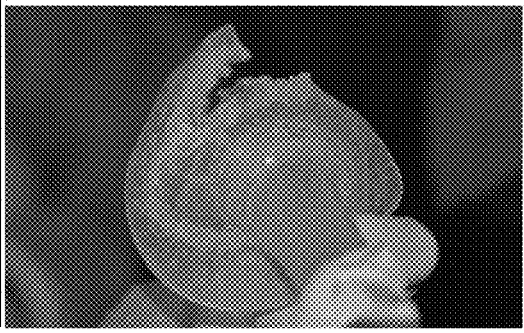

The device's retention mechanism was tested by pulling the device outwards with controlled force, the test being conducted at the beginning and at the end of the study in order to check for possible degradation in retention capa bility over time. In all of the retention tests the device has demonstrated retention ability against pulling force equal to or greater than 1.5 kg, which represents intra-colonic pressure of more than 200 mmHg. Occurrence of unintended device ejections was sporadic (FIG. 32). Part of the device ejections were due to the anatomical location of the stoma at the bottom side of the animal's abdomen (FIG. 35a) due to the animals frequently rubbing the device against the stall's floor while crouching (FIG. 35b). Device ejections also occurred due to efforts of the animals to reject the unfamiliar device, rejections that frequently concluded with destroyed devices (FIGS. 35c-35d).

TABLE 2

Planned and actual total durations of the device insertion routine

| Animal no. | Duration of device insertion routine (days) | |
|---|---|---|
| | Planned | Actual |
| 9 | 84 | 97 |
| 10 | 56 | 63 |
| 12 | 28 | 35 |
| 13 | 28 | 29 |

TABLE 3

Results of retaining test conducted at the beginning and at the end of the device insertion routine, in terms of pulling force (kg) required for device withdrawal. Inflation volume: 40 ml.

| Animal number | 9 | 10 | 12 | 13 |
|---|---|---|---|---|
| Beginning | >1.42 | >1.4 | >1.5 | >1.49* |
| End | >1.6 | >1.6 | >1.6 | >1.5 |

*Device inflated with 45 ml air.

TABLE 4

Results of sealing test conducted at the beginning ("Beg.") and at the end ("End") of the device insertion routine, in terms of leakage rate. Water or saline was injected behind the device, and leakage was visually inspected in three conditions: relaxed device (retention balloon not tightened against the abdominal wall), abdominal wall vigorously massaged (mimicking dynamics of living animal), and device under 200 gr. tension (retention balloon slightly tightened against the abdominal wall).

| Test condition | Animal #9 | | Animal #10 | | Animal #12 | | Animal #13 | |
|---|---|---|---|---|---|---|---|---|
| | Beg. | End | Beg. | End | Beg. | End | Beg. | End |
| Relaxed | None* | None | None | None | None | None | Slight | None |
| Massaged | None | None | None | None | None | None | Slight | None |
| Tension | None | None | None | None | None | None | None | None |

*Slight leakage was observed when the device was further pushed inwards into the abdominal cavity.

The device's ability to seal the intestine and thus prevent leakage of fecal matter was demonstrated in a series of sealing tests, in which liquid water or saline was filling the intestine behind the device. In almost all of the tests very good sealing was observed with relaxed device (i.e. device that is not tightened against the abdominal wall), even upon vigorous massaging of peristomal skin. No leakage was detected when slightly pulling the device outwards. It is to be noted that when used in appropriate length, the AOS-C100™ is designed so that such a slight force always tightens the retention balloon against the abdominal wall. Sealing ability can be further demonstrated by the fact that between 50 to 100 ml of fecal matter was regularly expelled from the stoma upon removal of the device (FIG. 34). This amount of excrement has naturally accumulated in the intestine behind the device during the period in which the device was inserted, and was prevented from being expelled by the device's sealing mechanism. The spontaneous discharge also confirms that no interruption in normal intestinal propelling was caused by the presence of the device. Fecal matter was shown to flow into the device's tube (FIG. 33), confirming the ability of the device to transfer excrements.

It may be concluded that study objectives have been fully met (see Table 5), with the device being safe to use, causing no physiological or clinical difficulties, and exhibiting good sealing and retention capabilities.

TABLE 5

Summary of the study objectives along with the relevant findings

| | Objectives | Findings |
|---|---|---|
| Safety | The effect of the device on the animal's general health | All animals were exhibiting active and vital behavior. All animals were constantly gaining weight. |
| | The effect of the device on the intestinal tissue and peristomal skin | No significant findings in the stoma, intestine and peristomal skin neither in routine manual and visual examination, nor in postmortem macro-pathological and pathological evaluations (FIGS. 8-9). |
| | The ability of the device to transfer fecal matter | Fecal matter demonstrated to fill the device's tube (FIG. 11). |
| | The ability of the device to transfer fecal matter without causing or contributing to an intestinal blockage | Neither intestinal blockage nor any other fecal propelling difficulties were observed. Fecal matter was regularly ejected from the stoma upon removal of the device. |
| | The effect of insertion and removal of the device on the device's performance and on the intestinal tissue. | No degradation in device performance or tissue condition observed. |
| Effectiveness | The functionality of the device's retention mechanism. | Device was repeatedly retained in the body upon pulling by 1.5 kg force. Low incidence of unintended device ejections. No degradation in device retention ability observed along study duration. |

TABLE 5-continued

Summary of the study objectives along with the relevant findings

| Objectives | Findings |
| --- | --- |
| The ability of the device to hermetically seal the intestine | Good sealing against liquid water exhibited in all sealing tests. No degradation in sealing ability observed at the end of the study relative to its beginning. No leakage of fecal matter observed with device in place, even upon elevation in intra-abdominal pressure (FIG. 11). |

REFERENCES

Botero-Anug A M. Histological evaluation report: Pig #9. Dec. 10, 2010. Data on file, Stimatix GI Ltd.

Botero-Anug A M. Histological evaluation report: Pig #10. Nov. 17, 2010. Data on file, Stimatix GI Ltd.

Botero-Anug A M. Histological evaluation report: Pigs #12, #13. Nov. 7, 2010. Data on file, Stimatix GI Ltd.

PreClinical Group. Evaluation of Stimatix GI artificial colostomy sphincter in a pig model: Preclinical study data summary. Dec. 12, 2010. Data on file, Stimatix GI Ltd.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the present invention. To the extent that section headings are used, they should not be construed as necessarily limiting.

What is claimed is:

1. An ostomy port for conducting waste content from a portion of intestine on a visceral side of an abdominal wall to an exterior of said abdominal wall, through a stoma of said intestine, comprising:
   a tube, axially elastic along a longitudinal extent, and sufficiently pliable for being radially and reversibly collapsible upon constriction within said portion of intestine;
   an elastic fixation element attached to a visceral-side opening of said tube, and insertable into said visceral-side intestinal portion to anchor said port; and
   an elastic stoma cover, attached to an exterior-side opening of said tube, widening therefrom, and extending back over an exterior-side region of the ostomy port for contacting a surface of the exterior abdominal wall distanced from the external-side tissue of the stoma, forming a ring-shaped covering region sized to externally surround the external-side tissue of the stoma;
   said tube being of a length to extend longitudinally from a proximal side connected with said stoma cover along said length of intestine extending distally from said stoma and cross said abdominal wall such that said tube reaches said visceral side of said abdominal wall;
   the stoma cover being deformable such that any point on a circumference of the stoma cover may be displaced in the axial direction by up to a predetermined maximum level;
   wherein the tube is adapted to bend for accommodating relative motion between the stoma cover and the fixation element due to displacement by changes in tissue position while inserted across said abdominal wall.

2. The ostomy port according to claim 1 characterized by the pressure applied by said fixation element due to said tensile force decreasing to less than 10 mmHg when colonic pressure is equal to or greater than approximately 10 mmHg.

3. The ostomy port according to claim 1 wherein said tube includes a material of durometer ranging from 5 to 50 shore A.

4. The ostomy port according to claim 1 wherein said tube comprises a material of durometer ranging from 20-30 shore A.

5. The ostomy port according to claim 1 wherein said fixation element includes a material of a durometer ranging from 5 to 50 Shore A.

6. The ostomy port according to claim 1 wherein said fixation element is a balloon and wherein said balloon includes a seamless exterior surface.

7. The ostomy port according to claim 1 wherein said fixation element deforms in an axial direction when pressed against the abdominal wall.

8. The ostomy port according to claim 7 wherein pressure applied by said fixation element on the abdominal wall ranges from 1 to 200 mmHg.

9. The ostomy port according to claim 1 wherein said cover includes an elastic material of a durometer ranging from 5 to 50 Shore A.

10. The ostomy port according to claim 1 wherein said cover is deformable by 5 mm in an axial direction.

11. The ostomy port according to claim 1 wherein said cover is substantially mushroom-shaped.

12. The ostomy port according to claim 1 wherein said cover includes a shape which is adjustable to variations in abdominal wall thickness.

13. The ostomy port according to claim 1, further comprising a gas filtering mechanism.

14. The ostomy port according to claim 1, further comprising an active gas release mechanism for release of flatus.

15. The ostomy port according to claim 14 wherein the active gas release mechanism includes a valve.

16. The ostomy porting according to claim 1 wherein said tube, said cover, and said fixation element are integrally formed in said ostomy port.

17. The ostomy port according to claim 16 further comprising an integral waste collection bag.

18. The ostomy port according to claim 1 comprising a deformable cap for providing a visual indication of an intra-colonic pressure of approximately 100 mmHg or greater.

19. The ostomy port according to claim 1 wherein said fixation element deforms in an axial direction when pressed against the abdominal wall.

20. The ostomy port according to claim 1, further comprising:
   a cap for sealing said exterior-side opening;
   wherein said cap includes a shell for accommodating a waste content collection bag.

21. The ostomy port according to claim 20 wherein said waste content collection bag is deployable from said shell upon sensing of an intra-colonic pressure of approximately 100 mmHg or greater.

22. The ostomy port according to claim 20 wherein said waste collection bag is deployed through a removable cover.

23. The ostomy port according to claim 20 wherein said tube includes an attachment mechanism for attaching said waste content collection bag.

24. The ostomy port according to claim 23 wherein said attachment mechanism includes a snap-and-fit arrangement for securing said waste content collection bag to said tube.

25. The ostomy port according to claim 1, wherein said predetermined maximum level is 10 mm.

26. The ostomy port according to claim 1 wherein said tube includes an attachment mechanism for attaching a waste content collection bag.

27. The ostomy port according to claim 26 wherein said attachment mechanism includes a snap-and-fit arrangement for securing said waste content collection bag to said tube.

28. The ostomy port according to claim 1, wherein a portion of said cover is invertable to expose the external-side tissue of the stoma.

29. The ostomy port according to claim 1, wherein said fixation element deforms non-uniformly, upon said relative movement including a non-axial component, such that pressing against the visceral-side intestinal portion is maintained below said predetermined maximum level.

30. The ostomy port according to claim 1, wherein said stoma cover deforms non-uniformly, upon said relative movement including a non-axial component, such that pressing against the exterior abdominal wall is maintained below said predetermined maximum level.

31. The ostomy port according to claim 1, wherein the tube is adapted to allow peristaltic propelling of waste content.

* * * * *

UNITED STATES PATENT AND TRADEMARK OFFICE
CERTIFICATE OF CORRECTION

PATENT NO. : 9,987,160 B2
APPLICATION NO. : 14/499289
DATED : June 5, 2018
INVENTOR(S) : David Hanuka et al.

Page 1 of 1

It is certified that error appears in the above-identified patent and that said Letters Patent is hereby corrected as shown below:

In the Claims

Column 32, Line 51, replace "ostomy porting" with --ostomy port--.

Column 34, Line 3, replace "invertable" with --invertible--.

Signed and Sealed this
Fifth Day of March, 2019

Andrei Iancu
*Director of the United States Patent and Trademark Office*